US010540786B2

(12) United States Patent
Lynn et al.

(10) Patent No.: US 10,540,786 B2
(45) Date of Patent: Jan. 21, 2020

(54) GRAPHICALLY PRESENTING FEATURES OF RISE OR FALL PERTURBATIONS OF SEQUENTIAL VALUES OF FIVE OR MORE CLINICAL TESTS

(71) Applicant: Lawrence A. Lynn, Columbus, OH (US)

(72) Inventors: Lawrence A. Lynn, Columbus, OH (US); Eric N. Lynn, Villa Ridge, MO (US)

(73) Assignee: Lawrence A. Lynn, Columbus, OH (US)

( * ) Notice: Subject to any disclaimer, the term of this patent is extended or adjusted under 35 U.S.C. 154(b) by 648 days.

(21) Appl. No.: 14/194,474

(22) Filed: Feb. 28, 2014

(65) Prior Publication Data

US 2014/0241603 A1   Aug. 28, 2014

Related U.S. Application Data

(60) Provisional application No. 61/770,971, filed on Feb. 28, 2013, provisional application No. 61/770,919, filed on Feb. 28, 2013.

(51) Int. Cl.
| | |
|---|---|
| *G06T 11/00* | (2006.01) |
| *G16H 10/60* | (2018.01) |
| *G16H 50/70* | (2018.01) |
| *G16H 50/20* | (2018.01) |
| *G01N 33/48* | (2006.01) |
| *G06T 11/20* | (2006.01) |
| *A61B 5/00* | (2006.01) |
| *A61B 5/145* | (2006.01) |

(52) U.S. Cl.
CPC ............. *G06T 11/00* (2013.01); *G01N 33/48* (2013.01); *G06T 11/206* (2013.01); *G16H 10/60* (2018.01); *G16H 50/20* (2018.01); *G16H 50/70* (2018.01); *A61B 5/14546* (2013.01); *A61B 5/7282* (2013.01)

(58) Field of Classification Search
None
See application file for complete search history.

(56) References Cited

U.S. PATENT DOCUMENTS

| | | |
|---|---|---|
| 4,630,614 A | 12/1986 | Atlas |
| 5,398,682 A | 3/1995 | Lynn |
| 5,520,176 A | 5/1996 | Cohen |
| 5,639,617 A | 6/1997 | Bohuon |
| 5,769,082 A | 6/1998 | Perel |
| 5,804,370 A | 9/1998 | Romaschin et al. |
| 5,840,019 A | 11/1998 | Wirebaugh |
| 5,942,986 A | 8/1999 | Shabot et al. |
| 6,120,441 A | 9/2000 | Griebel |
| 6,148,814 A | 11/2000 | Clemmer et al. |
| 6,159,683 A | 12/2000 | Romaschin et al. |
| 6,342,039 B1 | 1/2002 | Lynn et al. |
| 6,583,794 B1 | 6/2003 | Wattenberg |
| 6,609,016 B1 | 8/2003 | Lynn |
| 6,683,609 B1 | 1/2004 | Baron, Sr. et al. |
| 6,748,252 B2 | 6/2004 | Lynn et al. |
| 6,752,150 B1 | 6/2004 | Remmers et al. |
| 6,760,608 B2 | 7/2004 | Lynn |
| 6,804,656 B1 | 10/2004 | Rosenfield et al. |
| 6,816,266 B2 | 11/2004 | Varshneya et al. |
| 7,081,095 B2 | 7/2006 | Lynn et al. |
| 7,252,637 B2 | 8/2007 | Ebner et al. |
| 7,398,115 B2 | 7/2008 | Lynn |
| 7,428,520 B2 | 9/2008 | Armstrong et al. |
| 7,465,555 B2 | 12/2008 | Anderson et al. |
| 7,632,685 B2 | 12/2009 | Ivey et al. |
| 7,645,573 B2 | 1/2010 | Ivey et al. |
| 7,645,613 B2 | 1/2010 | Ivey et al. |
| 7,659,075 B2 | 2/2010 | Bergmann |
| 7,664,601 B2 | 2/2010 | Daly, Jr. |
| 7,668,579 B2 | 2/2010 | Lynn |
| 7,706,852 B2 | 4/2010 | Baker, Jr. |
| 7,723,492 B2 | 5/2010 | Bergmann et al. |
| 7,758,503 B2 | 7/2010 | Lynn et al. |
| 7,767,395 B2 | 8/2010 | Garrett et al. |
| 7,792,642 B1 | 9/2010 | Neilley et al. |
| 7,970,725 B2 | 6/2011 | Armstrong et al. |
| 8,152,732 B2 | 4/2012 | Lynn et al. |
| 8,187,201 B2 | 5/2012 | Lynn |
| 8,241,213 B2 | 8/2012 | Lynn et al. |
| 8,274,360 B2 | 9/2012 | Sampath et al. |
| 8,275,553 B2 | 9/2012 | Ochs et al. |
| 8,365,730 B2 | 2/2013 | Baker, Jr. et al. |
| 8,398,555 B2 | 3/2013 | Ochs et al. |
| 8,414,488 B2 | 4/2013 | Colman et al. |
| 8,428,966 B2 | 5/2013 | Green, III et al. |
| 8,438,041 B2 | 5/2013 | Green, III et al. |
| 8,439,835 B1 | 9/2013 | McKinley et al. |
| 8,527,449 B2 | 9/2013 | Gajic et al. |

(Continued)

FOREIGN PATENT DOCUMENTS

| | | |
|---|---|---|
| EP | 1529487 A1 | 7/2003 |
| JP | 05-266002 | 10/1993 |

(Continued)

OTHER PUBLICATIONS

Tatevossian, "Transcutaneous oxygen and CO2 as early warning of tissue hypoxia and hemodynamic shock in critically ill emergency patients," Critical care medicine, vol. 28(7), p. 2248-2253, 2000.*

(Continued)

*Primary Examiner* — G Steven Vanni
(74) *Attorney, Agent, or Firm* — Vorys, Sater, Seymour and Pease LLP; Rex W. Miller, II

(57) ABSTRACT

A patient monitoring system detects perturbations and detects or determines features of the perturbations and generates image cells responsive to the perturbations, organelles within the cells responsive to the features, and clinical regions responsive to the cells, and visualizations responsive to the clinical regions. The system also generates time-lapsable motion images comprising the cells which change over time in response to changes in the features or the detection of new perturbations. The system may convert the features into quanta defined at least in part by the clinical condition and may generate image components, such as pixels or groups of pixels, responsive to the quanta. Motion images may be generated from the image components.

15 Claims, 22 Drawing Sheets

(56) References Cited

U.S. PATENT DOCUMENTS

| | | |
|---|---|---|
| 8,663,107 B2 | 3/2014 | Kiani |
| 8,666,467 B2 | 5/2014 | Lynn et al. |
| 8,728,001 B2 | 7/2014 | Lynn |
| 8,781,753 B2 | 7/2014 | Ochs et al. |
| 2001/0018557 A1 | 8/2001 | Lynn et al. |
| 2002/0026941 A1 | 3/2002 | Biondi et al. |
| 2002/0030682 A1 | 3/2002 | Eberlein |
| 2002/0099273 A1 | 7/2002 | Bocionek et al. |
| 2002/0165462 A1 | 11/2002 | Westbrook et al. |
| 2002/0173707 A1 | 11/2002 | Lynn et al. |
| 2002/0190863 A1 | 12/2002 | Lynn |
| 2003/0101076 A1 | 5/2003 | Zaleski |
| 2003/0158466 A1 | 8/2003 | Lynn et al. |
| 2003/0181815 A1 | 9/2003 | Ebner et al. |
| 2003/0194752 A1 | 10/2003 | Anderson et al. |
| 2003/0228625 A1 | 12/2003 | Toh et al. |
| 2004/0039295 A1 | 2/2004 | Olbrich et al. |
| 2004/0048264 A1 | 3/2004 | Stoughton et al. |
| 2004/0078219 A1 | 4/2004 | Kaylor et al. |
| 2004/0078228 A1 | 4/2004 | Fitzgerald et al. |
| 2004/0096917 A1 | 5/2004 | Ivey et al. |
| 2004/0097460 A1 | 5/2004 | Ivey et al. |
| 2004/0106142 A1 | 6/2004 | Ivey et al. |
| 2004/0111014 A1 | 6/2004 | Hickle |
| 2004/0128163 A1 | 7/2004 | Goodman et al. |
| 2004/0157242 A1 | 8/2004 | Ivey et al. |
| 2004/0183683 A1 | 9/2004 | Funahashi |
| 2004/0249299 A1 | 12/2004 | Cobb |
| 2005/0001728 A1 | 1/2005 | Appelt et al. |
| 2005/0062609 A9 | 3/2005 | Lynn |
| 2005/0065556 A1 | 3/2005 | Reghabi et al. |
| 2005/0098178 A1 | 5/2005 | Banner et al. |
| 2005/0109340 A1 | 5/2005 | Tehrani |
| 2005/0125256 A1 | 6/2005 | Schoenberg et al. |
| 2005/0164238 A1 | 7/2005 | Valkirs et al. |
| 2005/0181354 A1 | 8/2005 | Estep, III |
| 2005/0182333 A1 | 8/2005 | Nagata et al. |
| 2005/0240091 A1 | 10/2005 | Lynn |
| 2006/0149144 A1 | 7/2006 | Lynn et al. |
| 2006/0155176 A1 | 7/2006 | Ebner et al. |
| 2006/0155206 A1 | 7/2006 | Lynn |
| 2006/0155207 A1 | 7/2006 | Lynn et al. |
| 2006/0157647 A1 | 7/2006 | Siuzdak et al. |
| 2006/0161071 A1 | 7/2006 | Lynn et al. |
| 2006/0189880 A1 | 8/2006 | Lynn et al. |
| 2006/0195041 A1 | 8/2006 | Lynn et al. |
| 2006/0195149 A1 | 8/2006 | Hopper et al. |
| 2006/0200012 A1 | 9/2006 | Mansour et al. |
| 2006/0235324 A1 | 10/2006 | Lynn |
| 2006/0235726 A1 | 10/2006 | Paraison et al. |
| 2006/0253300 A1 | 11/2006 | Somberg et al. |
| 2006/0271408 A1 | 11/2006 | Rosenfeld et al. |
| 2006/0276695 A9 | 12/2006 | Lynn et al. |
| 2007/0093701 A1 | 4/2007 | Myers et al. |
| 2007/0093721 A1 | 4/2007 | Lynn et al. |
| 2007/0129647 A1 | 6/2007 | Lynn |
| 2007/0149860 A1 | 6/2007 | Lynn et al. |
| 2007/0184512 A1 | 8/2007 | Ivey et al. |
| 2007/0191688 A1 | 8/2007 | Lynn |
| 2007/0191697 A1 | 8/2007 | Lynn et al. |
| 2007/0255322 A1 | 11/2007 | Gerber et al. |
| 2007/0282212 A1 | 12/2007 | Sierra et al. |
| 2008/0050829 A1 | 2/2008 | Ivey et al. |
| 2008/0051764 A1 | 2/2008 | Dent et al. |
| 2008/0091088 A1 | 4/2008 | Kiani |
| 2008/0114576 A1 | 5/2008 | Jackson et al. |
| 2008/0138832 A1 | 6/2008 | Ivey et al. |
| 2008/0195322 A1 | 8/2008 | Altschuler et al. |
| 2008/0200775 A1 | 8/2008 | Lynn |
| 2008/0200819 A1 | 8/2008 | Lynn et al. |
| 2008/0208012 A1 | 8/2008 | Ali |
| 2008/0208618 A1 | 8/2008 | Schoenberg et al. |
| 2008/0235049 A1 | 9/2008 | Morita et al. |
| 2008/0235057 A1 | 9/2008 | Weidenhaupt et al. |
| 2008/0275349 A1 | 11/2008 | Halperin et al. |
| 2008/0286763 A1 | 11/2008 | Russwurm et al. |
| 2008/0287756 A1 | 11/2008 | Lynn |
| 2008/0305464 A1 | 12/2008 | Lynn |
| 2009/0069704 A1 | 3/2009 | MacAdam et al. |
| 2009/0082641 A1 | 3/2009 | Giftakis et al. |
| 2009/0083072 A1 | 3/2009 | Osawa et al. |
| 2009/0143694 A1 | 6/2009 | Krauss et al. |
| 2009/0171169 A1 | 7/2009 | Nagata |
| 2009/0186774 A1 | 7/2009 | Turner et al. |
| 2009/0187082 A1 | 7/2009 | Cuddihy et al. |
| 2009/0281838 A1 | 11/2009 | Lynn et al. |
| 2009/0281839 A1 | 11/2009 | Lynn et al. |
| 2009/0299154 A1 | 12/2009 | Segman |
| 2009/0318775 A1 | 12/2009 | Michelson et al. |
| 2010/0066540 A1 | 3/2010 | Theobald et al. |
| 2010/0070888 A1 | 3/2010 | Watabe et al. |
| 2010/0079292 A1 | 4/2010 | Lynn |
| 2010/0094648 A1 | 4/2010 | Seward |
| 2010/0160171 A1 | 6/2010 | Freishtat |
| 2010/0174161 A1 | 7/2010 | Lynn |
| 2010/0234705 A1 | 9/2010 | Lynn |
| 2010/0261977 A1 | 10/2010 | Seely |
| 2011/0009722 A1 | 1/2011 | Amundson et al. |
| 2011/0009760 A1 | 1/2011 | Zhang et al. |
| 2011/0015501 A1 | 1/2011 | Lynn et al. |
| 2011/0130671 A1 | 1/2011 | MacQuarrie et al. |
| 2011/0105350 A1 | 5/2011 | Garrett et al. |
| 2011/0118569 A1 | 5/2011 | Shi et al. |
| 2011/0208018 A1 | 8/2011 | Kiani |
| 2011/0208539 A1 | 8/2011 | Lynn |
| 2012/0053425 A1 | 3/2012 | Michelson et al. |
| 2012/0145152 A1 | 6/2012 | Lain et al. |
| 2012/0165623 A1 | 6/2012 | Lynn et al. |
| 2012/0172247 A1 | 7/2012 | Narimatsu et al. |
| 2012/0197094 A1 | 8/2012 | Zhang et al. |
| 2012/0220845 A1 | 8/2012 | Campbell |
| 2012/0232359 A1 | 9/2012 | Al-Ali et al. |
| 2012/0302845 A1 | 11/2012 | Lynn et al. |
| 2012/0328594 A1 | 12/2012 | McKenna et al. |
| 2012/0330118 A1 | 12/2012 | Lynn et al. |
| 2013/0052671 A1 | 2/2013 | Grueb et al. |
| 2013/0060110 A1 | 3/2013 | Lynn et al. |
| 2013/0073311 A1 | 3/2013 | Lynn et al. |
| 2013/0124221 A1 | 5/2013 | Lynn |
| 2013/0131993 A1 | 5/2013 | Lynn et al. |
| 2013/0158375 A1 | 6/2013 | Lynn |
| 2013/0209068 A1 | 8/2013 | Lynn |
| 2013/0218600 A1 | 8/2013 | Lynn et al. |
| 2013/0268291 A1 | 10/2013 | Lynn et al. |
| 2013/0290011 A1 | 10/2013 | Lynn et al. |
| 2013/0338459 A1 | 12/2013 | Lynn |
| 2014/0152673 A1 | 6/2014 | Lynn et al. |
| 2014/0163897 A1 | 6/2014 | Lynn et al. |
| 2014/0176538 A1 | 6/2014 | Lynn et al. |
| 2014/0176558 A1 | 6/2014 | Lynn et al. |
| 2014/0180722 A1 | 6/2014 | Lynn et al. |

FOREIGN PATENT DOCUMENTS

| | | |
|---|---|---|
| JP | 2002336207 A | 11/2002 |
| JP | 2007058565 A | 3/2007 |
| JP | 4435681 B2 | 3/2010 |
| KR | 102002006420 6 | 8/2002 |
| WO | WO 2004/056301 A2 | 7/2004 |
| WO | WO 2005/056087 A1 | 6/2005 |
| WO | 2009137682 A1 | 11/2009 |
| WO | 2010065262 A1 | 6/2010 |
| WO | WO 2010/108018 A3 | 9/2010 |
| WO | 2013/074708 A1 | 5/2013 |

OTHER PUBLICATIONS

Campbell, Beverly, Arterial Waveforms: Monitoring Changes in Configuration, Hemodynamics, Heart & Lung, May/Jun. 1997, vol. 26, No. 3, pp. 204-214.

(56) References Cited

OTHER PUBLICATIONS

Herasevich et al., Designing and testing computer based screening engine for severe sepsis/septic shock, AMIA 2008 Symposium Proceedings, p. 864.

Herasevich et al., Enrollment into a time sensitive clinical study in the critical care setting: results from computerized septic shock sniffer implementation, J Am Med Inform Assoc. 2011, vol. 18, pp. 639-644.

Simon et al., Heat maps as a tool for large, in hospital database visualization for rapid hypothesis generation, Multidisciplinary Epidemiology and Translational Research in Intensive Care, Mayo Clinic, p. 1961.

Author Unknown, Wheel figure retrieved from the following website: http://www.getatomiq.com/content/images/faq/wheel.png, 1 page, viewed on Aug. 3, 2012.

Non-Final Office Action for U.S. Appl. No. 13/677,295, dated Apr. 8, 2015, 15 pages.

Non-Final Office Action for U.S. Appl. No. 13/844,381, dated Apr. 9, 2015, 21 pages.

Non-Final Office Action for U.S. Appl. No. 13/844,212, dated Apr. 9, 2015, 21 pages.

Non-Final Office Action for U.S. Appl. No. 13/844,404, dated Apr. 9, 2015, 18 pages.

Non-Final Office Action for U.S. Appl. No. 13/843,481, dated Apr. 9, 2015, 19 pages.

Final Office Action for U.S. Appl. No. 12/437,385, dated May 14, 2015, 31 pages.

Non-Final Office Action for U.S. Appl. No. 12/777,171, dated Mar. 5, 2015, 12 pages.

Non-Final Office Action for U.S. Appl. No. 14/193,757, dated May 8, 2015, 15 pages.

Non-Final Office Action for U.S. Appl. No. 14/193,829, dated May 22, 2015, 17 pages.

Non-Final Office Action for U.S. Appl. No. 14/193,376, dated May 29, 2015, 24 pages.

Fawcett, Tom, ROC Graphs: Notes and Practical Considerations for Data Mining Researchers, Hewlett-Packard Company, 2003, 28 pages.

Guven et al., Diagnostic Value of Procalcitonin Levels as an Early Indicator of Sepsis, Am JEmerg Med, 2002m pp. 202-206, vol. 20.

Haumptman et al., Evaluation of the Sensitivity and Specificity of Diagnostic Criteria for Sepsis in Dogs, Veterinary Surgery, 1997, pp. 393-379, vol. 26.

International Search Report for International (PCT) Patent Application No. PCT/US2012/065124, dated Jul. 23, 2015, 6 pages.

Rao, Singiresu, Engineering Optimization Theory: Advantages of Random Search Methods, 2009, pp. 314-317.

Abelson, Harold et al., Structure and Interpretation of Computer Programs, MIT Press, 2nd Edition, 1996, p. 99-107, 113-126.

Abraham, E., et al., Sequential Cardiorespiratory Patterns in Septic Shock, Crit Care Med., Oct. 1983, pp. 799-803, vol. 11, No. 10.

Agronsky, Dominik, et al., Diagnosing Community-Acquired Pneumonia with a Bayesian Network, AMIA, Inc., 1998, pp. 632-636.

Alattar, M. A.et al., Opiod-associated central sleep apnea: a case series, 2009, pp. 201-206.

Apostolopoulou, Eleni et al, Infection Probability Score, Apache II and Karnofsky scoring systems as predictors of bloodstream infection onset in hematology-oncology patients, BMC Infectious Diseases, 2010, vol. 10, No. 135, 8 pages.

Augusto, Juan Carlos, Temporal Reasoning for Decision Support in Medicine, Artificial Intelligence in Medicine, 2005, vol. 33, pp. 1-24.

Bland, RD et al., Probability of Survival as a Prognostic and Severity of Illness Score in Critically Ill Surgical Patients, Crit Care Med., Feb. 1985, pp. 91-95, vol. 13, No. 2 (Abstract).

Bossink, Alko et al., Prediction of Mortality in Febrile Medical Patients, Chest, Jun. 1998, vol. 113, No. 6, pp. 1533-1541.

Brabrand, Mikkel et al., Risk scoring systems for adults admitted to the emergency department: a systematic review, Scandinavian Journal of Trauma, Resuscitation & Emergency Medicine, Retrieved from <http://www.sjtrem.com/content/18/1/8>, 2010, pp. 1-8.

Burykin, Anton et al., Toward optimal display of physiologic status in critical care: I. Recreating bedside displays from archived physiologic data, Journal of Critical Care, 2010 (Article in Press), 9 pages.

Cavallazzi, MD, Rodrigo, Is the Band Count Useful in the Diagnosis of Infection? An Accuracy Study in Critically Ill Patients, Journal of Intensive Care Medicine, 2010, 5 pages.

Charbonnier et al., "A trend-based alarm system to improve patient monitoring in intensive care units." Control Engineering Practice, Pergamon Press, Oxford, GB, May 12, 2007, pp. 1039-1050, vol. 15, No. 9.

Crowe, Colleen A.et al., Comparison of severity of illness scoring systems in the prediction of hospital mortality in severe sepsis and septic shock, Journal of Emergencies, Trauma, and Shock, Oct.-Dec. 2010, pp. 342-347, Oak Lawn, IL, USA.

Diep, Binh Anet al., Polymorphonuclear leukocytes mediate *Staphylococcus aureus* Panton-Valentine leukocidin-induced lung inflammation and injury, PNAS, Mar. 2010, pp. 5587-5592, vol. 107 No. 12.

Dojat, Michel et al., Scenario recognition for temporal reasoning in medical domains, Artificial Intelligence in Medicine, 1998, pp. 139-155, Elsevier Science B.V., Cedex, France.

Finlay, Heather et al., Designing and Testing a Computer-Based Screening System for Transfusion-Related Acute Lung Injury, Am J Clin Pathol, 2005, vol. 124, pp. 601-609.

Fry, Donald et al., The Changing Face of *Staphylococcus aureus*: A Continuing Surgical Challenge, Surgical Infections, 2011, vol. 12, No. 3, pp. 191-203.

Ghanem-Zoubi, Nesrin O. et al., Assessment of disease-severity scoring systems for patients with sepsis in general internal medicine departments, Critical Care, Retrieved from <http://ccforum.com/content/15/2/R95>, 2011, pp. 1-7.

Herasevich, Vitaly et al., Designing and testing computer based screening engine for severe sepsis/septic shock, AMIA Annu Symp Proc. Nov. 2008 (Abstract).

Herasevich, Vitaly et al., Enrollment into a time sensitive clinical study in the critical care setting: results from computerized septic shock sniffer implementation, J Am Med Inform Assoc, 2011, vol. 18, pp. 639-644.

Herasevich, Vitaly et al., Limiting ventilator-induced lung injury through individual electronic medical record surveillance, Crit Care Med, 2011, vol. 39, No. 1, pp. 34-39.

Herasevich, Vitaly et al., Validation of an electronic surveillance system for acute lung injury, Intensive Care Med., Jun. 2009, vol. 35, No. 6, pp. 118-1023.

International Preliminary Report on Patentability Including Written Opinion for International (PCT) Patent Application No. PCT/US2009/043150, dated Nov. 9, 2010 9 pages.

International Preliminary Report on Patentability including Written Opinion for International (PCT) Patent Application No. PCT/US2009/064312, dated May 31, 2011 10 pages.

International Search Report for International (PCT) Patent Application No. PCT/US2009/043150, dated Aug. 4, 2009 3 pages.

International Search Report for International (PCT) Patent Application No. PCT/US2009/064312, dated Feb. 26, 2010 4 pages.

International Search Report for International (PCT) Patent Application No. PCT/US2009/065124, dated Mar. 25, 2013, 10 pages.

International Search Report for International (PCT) Patent Application No. PCT/US2012/065129, dated Mar. 20, 2013, 12 pages.

International Search Report for International (PCT) Patent Application No. PCT/US2014/019577, dated May 28, 2014 (English) 11 pages.

International Search Report for International (PCT) Patent Application No. PCT/US2014/019587, dated Jun. 17, 2014 (English) 10 pages.

International Search Report for International (PCT) Patent Application No. PCT/US2014/019625, dated Jun. 17, 2014 (English) 18 pages.

(56) References Cited

OTHER PUBLICATIONS

International Search Report for International (PCT) Patent Application No. PCT/US2014/019637, dated Jun. 18, 2014 (English) 11 pages.
International Search Report for International (PCT) Patent Application No. PCT/US2014/019572, dated Jun. 26, 2014 (English) 9 pages.
International Search Report for International (PCT) Patent Application No. PCT/US2014/019556, dated Jun. 27, 2014 (English) 14 pages.
International Search Report for International (PCT) Patent Application No. PCT/US2014/019530, dated Jun. 27, 2014 (English) 11 pages.
International Search Report for International (PCT) Patent Application No. PCT/US2014/019442, dated Jul. 7, 2014 (English) 11 pages.
International Search Report for International (PCT) Patent Application No. PCT/US2014/019582, dated Aug. 28, 2014 (English) 12 pages.
Kellett, J. et al., The Simple Clinical Score predicts mortality for 30 day admission to an acute medical unit, QJ Med, 2006, vol. 99, pp. 771-781.
Kreisel, Kristen et al., USA300 Methicillin-resistant *Staphylococcus aureus* bacteremia and the risk of severe sepsis: is USA300 Methicillin-resistant *Staphylococcus aureus* associated with more severe infections?, Diagnostic Microbiology and Infectious Disease, 2011, vol. 70, pp. 285-290.
Lappin, Emma et al., Gram-Positive Toxic Shock Syndromes, The Lancet, May 2009, vol. 9, pp. 281-290.
Levy, Mitchell M. et al., 2001 SCCM/ESICM/ACCP/ATS/SIS International Sepsis Definitions Conference, Critical Care Medicine, 2003, pp. 1250-1256, vol. 31 No. 4.
Lu, K, et al., A Mathematical Program to Predict Survival and to Support Initial Therapeutic Decisions for Trauma Patients With Long-Bone and Pelvic Fractures, Injury, Mar. 2007, pp. 318-328.
Lynn, Lawrence A. et al., Patterns of unexpected in-hospital deaths: a root cause analysis, Retrieved from <http://www.passjournal.com/content/5/1/3>, Patient Safety in Surgery, Feb. 11, 2011, pp. 1-24, vol. 5, No. 3, BioMed Central.
Mackenzie, I.M.J., The Haemodynamics of Human Septic Shock, Anaesthesia, 2001, vol. 56, pp. 130-144.
MacLean, Lloyd et al., Patterns of Septic Shock in Man—A Detailed Study of 56 Patients, Annals of Surgery, Oct. 1967, vol. 166, No. 4, pp. 543-558.
Marik, Paul et al., The definition of septic shock: implications for treatment, Critical Care and Resuscitation, Mar. 2007, vol. 9, No. 1, Mar. 2007, pp. 101-103.
Marik, Paul, Surviving sepsis: going beyond the guidelines, Annals of Intensive Care, Jun. 7, 2011, 1:17, 6 pages.
Members of the American College of Chest Physicians/Society of Critical Care Medicine Consensus Conference Committee, Definitions for sepsis and organ failure and guidelines for the use of innovative therapies in sepsis, Critical Care Medicine, 1992, pp. 864-874, vol. 20 No. 6.
Nguyen, H. Bryant et al., Severe Sepsis and Septic Shock: Review of Literature and Emergency Department Management Guidelines, Annals of Emergency Medicine, Jul. 2006, pp. 28-54, vol. 48 No. 1.
Opal, Steven, The Uncertain Value of the Definition for SIRS, Editorial downloaded from www.journal.publications.chestnet.org/ on Nov. 19, 2013, pp. 1442-1443.
Patel, M.S.et al., Does the use of a "track and trigger" warning system reduce mortality in trauma patients?, Injury, May 25, 2011, doi:10.1016/j.injury.2011.05.030, pp. 1-5, Elsevier Ltd., United Kingdom.
Peres Bota, Daliana et al., Infection Probability Score (IPS): A method to help asses the probability of infection in critically ill patients, Crit Care Med, 2003, vol. 31, No. 11, pp. 2579-2584.
Rangel-Frausto MD, M. Sigfrido, The Natural History of the Systemic Inflammatory Response Syndrome (SIRS), JAMA, Jan. 11, 1995, vol. 273, No. 2, pp. 117-123.
Rivers, Emanuel et al., Early Goal-Directed Therapy in the Treatment of Severe Sepsis and Septic Shock, The New England Journal of Medicine, Nov. 8, 2001, vol. 345, No. 19, pp. 1368-1377.
Sawyer, Amber M. et al., Implementation of a real-time computerized sepsis alert in nonintensive care unit patients*, Critical Care Medicine, 2011, pp. 469-473, vol. 39, No. 3.
Seigel, Todd et al., Inadequacy of Temperature and White Blood Cell Count in Predicting Bacteremia in Patients with Suspected Infection, The Journal of Emergency Medicine, 2010, pp. 1-6.
Shoemaker, WC et al., Hemodynamic and Oxygen Transport Monitoring to Titrate Therapy in Septic Shock, New Horiz., Feb. 1993, pp. 145-159, vol. 1, No. 1 (Abstract).
Shoemaker, WC et al., Invasive and Noninvasive Haemodynamic Monitoring of Acutely Ill Sepsis and Septic Shock Patients in the Emergency Department, Eur J Emerg Med, Sep. 2000, pp. 169-175, vol. 7, No. 3.
Shoemaker, WC et al., Pathophysiology of Adult Respiratory Distress Syndrome After Sepsis and Surgical Operations, Crit Care Med., Mar. 1985, pp. 166-172, vol. 13, No. 3 (Abstract).
Shoemaker, WC et al., Role of Oxygen Debt in the Development of Organ Failure Sepsis, and Death in High-Risk Surgical Patients, Chest, Jul. 1992, pp. 208-215, vol. 102, No. 1.
Shoemaker, WC et al., Sequence of Physiologic Patterns in Surgical Septic Shock, Crit Care Med, Dec. 1993, pp. 1876-1889, vol. 21, No. 12.
Shoemaker, WC et al., Use of Sequential Physiologic Measurements for Evaluation and Therapy of Uncomplicated Septic Shock, Surgery, Gynecology & Obstetrics, Aug. 1970, pp. 245-254.
Shoemaker, WC, Cardiorespiratory Patterns in Complicated and Uncomplicated Septic Shock: Physiologic Alterations and Their Therapeutic Implications, Ann. Surg., Jul. 1971, pp. 119-125, vol. 174, No. 1.
Shoemaker, WC, Circulatory Mechanisms of Shock and Their Mediators, Crit Care Med., Aug. 1987, pp. 787-794, vol. 15, No. 8 (Abstract).
Shoemaker, WC, Temporal Hemodynamic and Oxygen Transport Patterns in Medical Patients, Chest, Nov. 1993, pp. 1529-1536, vol. 104, No. 5.
Shoemaker, WC, Temporal Physiologic Patterns of Shock and Circulatory Dysfunction Based on Early Descriptions by Invasive and Noninvasive Monitoring, New Horiz., May 1996, pp. 300-318, vol. 4, No. 2 (Abstract).
Shoemaker, William et al., Role of Physiologic Monitoring in the Intensive Care Unit, Surgery Annual, 1970, pp. 61-81.
Shoemaker, William, Pathophysiologic Basis of Therapy for Shock and Trauma Syndromes: Use of Sequential Cardiorespiratory Measurements to Describe Natural Histories and Evaluate Possible Mechanisms, Seminars in Drug Treatment, Winter 1973, vol. 3, No. 3, pp. 211-229.
Shoemaker, William, Physiologic Mechanisms in Clinical Shock, Adv Exp Med Biol, Oct. 23, 1971, pp. 57-75.
Shoemaker, William, Sequential Hemodynamic Patterns in Various Causes of Shock, Surgery, Gynecology & Obstetrics, Mar. 1971, pp. 411-423.
Simmons, Daniel et al., Hyperventilation and Respiratory Alkalosis as Signs of Gram-Negative Bacteremia, JAMA, Dec. 31, 1960, vol. 174, No. 18, pp. 2196-2199.
Simmons, Richard, The Role of Central Nervous System in Septic Shock, Annals of Surgery, Feb. 1968, vol. 167, No. 2, pp. 158-167.
Stacey et al., Temporal abstraction in intelligent data analysis: A survey, Artificial intelligence in medicine, Jan. 31, 2007, vol. 39, pp. 1-24.
Subbe, C. P. et al., Validation of a modified Early Warning Score in medical admissions, Original Papers, Q J Med, May 17, 2001 and in revised form Jul. 9, 2001, pp. 521-526, vol. 94, Association of Physicians.
Sun, Dong et al., The Natural History of the Systemic Inflammatory Response Syndrome and the Evaluation of SIRS Criteria as a Predictor of Severity in Patients Hospitalized through Emergency Services, 1999, vol. 48, No. 1; pp. 28-37.

(56) References Cited

OTHER PUBLICATIONS

Tufte, Edward R., The Visual Display of Quantitative Information (Graphics Press, 1983), pp. 17, 21, 153.
U.S. Appl. No. 11/431,686, Amendment and Response to NF Office Action, filed Jun. 21, 2011.
U.S. Appl. No. 11/431,686, Final Office Action, dated Oct. 12, 2011.
U.S. Appl. No. 11/431,686, Office Action (Restriction Requirement), dated Sep. 30, 2010.
U.S. Appl. No. 11/431,686, Response to Restriction Requirement, filed Oct. 29, 2010.
U.S. Appl. No. 12/437,385, Request for Continued Examination and Preliminary Amendment, filed Feb. 7, 2012.
U.S. Appl. No. 12/437,417, Amendment and Response to NF Office Action, dated Nov. 5, 2012.
U.S. Appl. No. 12/437,417, Amendment and Response to NF Office Action, dated Sep. 6, 2011, 13 pages.
U.S. Appl. No. 11/431,686, U.S. Appl. No. 11/431,686, NF Office Action, dated Jan. 21, 2011.
U.S. Appl. No. 12/437,385, Amendment and Response to NF Office Action, dated Jan. 15, 2013.
U.S. Appl. No. 12/437,385, Amendment and Response to NF Office Action, dated Sep. 6, 2011.
U.S. Appl. No. 12/437,385, Final Office Action, dated Nov. 25, 2011.
U.S. Appl. No. 12/437,385, NF Office Action, dated Apr. 5, 2011.
U.S. Appl. No. 12/437,385, NF Office Action, dated Aug. 17, 2012.
U.S. Appl. No. 12/437,417, Final Office Action, dated Feb. 14, 2013.
U.S. Appl. No. 12/437,417, NF Office Action, dated Aug. 3, 2012.
U.S. Appl. No. 12/437,417, NF Office Action, dated Mar. 4, 2011.
U.S. Appl. No. 12/437,417, NF Office Action, dated Nov. 29, 2011.
U.S. Appl. No. 12/437,417, Request for Continued Examination and Preliminary Amendment, filed Feb. 29, 2012.
U.S. Appl. No. 12/629,407, Amendment and Response to NF Office Action dated Sep. 25, 2012, filed Feb. 21, 2013.
U.S. Appl. No. 12/629,407, NF Office Action, dated Aug. 16, 2012.
U.S. Appl. No. 12/629,407, NF Office Action, dated Sep. 25, 2012.
U.S. Appl. No. 12/629,407, Response to Requirement for Restriction, filed Sep. 14, 2012.
Velmahos, George et al., Endpoints of Resuscitation of Critically Injured Patients: Normal or Supranormal?, Annals of Surgery, 2000, pp. 409-418, vol. 232, No. 3.
Wile, Michael J. et al., Manual Differential Cell Counts Help Predict Bacterial Infection, A Multivariate Analysis, Hematopathology, 2001, pp. 644-649, vol. 115, Am J Clin Pathol.
PCT—International Preliminary Report on Patentability, for PCT application No. PCT/US2014/019530; dated Sep. 1, 2015; 8 Pages.
PCT—International Preliminary Report on Patentability, for PCT application No. PCT/US2014/019556; dated Sep. 1, 2015; 9 Pages.
PCT—International Preliminary Report on Patentability, for PCT application No. PCT/US2014/019572; dated Sep. 1, 2015; 6 Pages.
PCT—International Preliminary Report on Patentability, for PCT application No. PCT/US2014/019577; dated Sep. 1, 2015; 8 Pages.
PCT—International Preliminary Report on Patentability, for PCT application No. PCT/US2014/019637; dated Sep. 1, 2015; 8 Pages.
PCT—International Preliminary Report on Patentability, for PCT application No. PCT/US2014/019442; dated Sep. 1, 2015; 6 Pages.
PCT—International Preliminary Report on Patentability, for PCT application No. PCT/US2014/019582; dated Sep. 1, 2015; 7 Pages.
PCT—International Preliminary Report on Patentability, for PCT application No. PCT/US2014/019587; dated Sep. 1, 2015; 6 Pages.
PCT—International Preliminary Report on Patentability, for PCT application No. PCT/US2014/019625; dated Sep. 1, 2015; 15 Pages.
Non-Final Office Action issued in U.S. Appl. No. 12/629,407, dated Oct. 2, 2015, 19 Pages.
Final Office Action issued in U.S. Appl. No. 13/843,481, dated Dec. 21, 2015, 26 pages.
Final Office Action issued in U.S. Appl. No. 13/844,381, dated Dec. 17, 2015, 25 pages.
Final Office Action issued in U.S. Appl. No. 13/844,212, dated Dec. 17, 2015, 24 pages.
Final Office Action issued in U.S. Appl. No. 13/844,404, dated Dec. 17, 2015, 27 pages.
Final Office Action issued in U.S. Appl. No. 13/677,295, dated Dec. 11, 2015, 20 pages.
Final Office Action issued in U.S. Appl. No. 14/193,376, dated Jan. 15, 2016, 26 pages.
Final Office Action issued in U.S. Appl. No. 14/193,829, dated Dec. 23, 2015, 22 pages.
Final Office Action issued in U.S. Appl. No. 14/193,757, dated Jan. 22, 2016, 30 pages.
European Search Report, for 12850333.1-1901/2780884 PCT/US2012065129, dated Jan. 14, 2016, 6 pages.
"Computed Tomography of the Chest: A Teaching File." M. Elon Gale & Joel B. Karlinsky. Year Book Medical Publishers, Inc. 1988. Chapter 1, pp. 1-4.
Richard J. Allen and Timothy C. Elston; "From Physics to Pharmacology?"; Department of Pharmacology, University of North Carolina at Chapel Hill, Chapel Hill, NC, US; Reports on Progress on Physics; Institute of Physics Publishing; vol. 74, No. 1; Dec. 3, 2010; pp. 1-19; stacks.iop.arg/RoPP174/016601.
Sergey M. Zuev, et al.; "Sepsis Progression and Outcome: A Dynamical Model"; Theoretical Biology and Medical Modelling, Biomed Central, Ltd.; London, GB; vol. 3, No. 1; Feb. 15, 2006; pp. 1-15; http://tbiomed.com/content/3/1/8.

\* cited by examiner

GRAPHICALLY PRESENTING FEATURES OF RISE OR FALL PERTURBATIONS OF SEQUENTIAL VALUES OF FIVE OR MORE CLINICAL TESTS

This application claims the benefit of U.S. Provisional Application Ser. No. 61/770,919 filed Feb. 28, 2013, the contents of which are hereby incorporated by reference, and U.S. Provisional Application Ser. No. 61/770,971 filed Feb. 28, 2013, the contents of which are hereby incorporated by reference. This application is also related to U.S. Patent Application Ser. No. 14/193,376, filed Feb. 28, 2014,titled "Time Lapsable Motion Image Responsive to Features of Pathophysiologic Perturbations," the entire contents of which are hereby incorporated by reference.

BACKGROUND

Human pathophysiology is highly complex and it is very difficult for physicians and nurses to timely detect many adverse clinical conditions in the many settings. U.S. Pat. Nos. 8,241,213, 8,152,732, 7,758,503, 7,398,115 and 7,081,095, as well as U.S. patent application Ser. Nos. 12/437,417, 12/437,385, 12/629,407 13/677,291, and 13/677,288 (the entire contents of each of these patents and patent applications are incorporated by reference as if completely disclosed herein) disclose processor methods, time series matrix analysis and objectification, processing systems, patient monitors for timely detection, identification, quantification, tracking, and generation of dynamic displays of sepsis and other conditions. These patents and patent applications provide additional background for the embodiments described herein.

Diagnostic systems and their limitations are discussed in U.S. Patent Application Ser. No. 61/770,919 filed Feb. 28, 2013, entitled "Patient storm Tracker and Visualization Processor," (the entire contents of each of these applications are incorporated by reference as if completely disclosed herein). This application also provides background for the embodiments described herein. Some embodiments described herein relate to systems and methods for analyzing complex datasets of medical records. FIG. 1 shows a conventional medical repository system 100 with associated cognitive support 102. In this figure a central repository 104 (such as Microsoft Health Vault or a hospital system's server or data repository) may store massive amounts of clinical data, for example, in database fields. Hospitals access the databases for clinical management of the patient 106. In many cases, patients may also observe their own data using secure portals.

Physicians and patients often find it difficult to deal with the complexity of the data available from these portals and especially to identify causation of complex or subtle perturbations. A major portion of the complexity of medical data is derived from the highly interrelated dynamic patterns of perturbations of the compartmentalized densities of human biologic particles. The dynamic complexity of the relational patterns of cascading biologic particle perturbations provides a major barrier to timely care.

BRIEF DESCRIPTION OF THE DRAWINGS

Various embodiments will be described hereinafter with reference to the accompanying drawings. These embodiments are illustrated and described by example only, and are not intended to limit the scope of the disclosure. In the drawings, similar elements may have similar reference numerals.

DETAILED DESCRIPTION OF EMBODIMENTS

Figure 1:
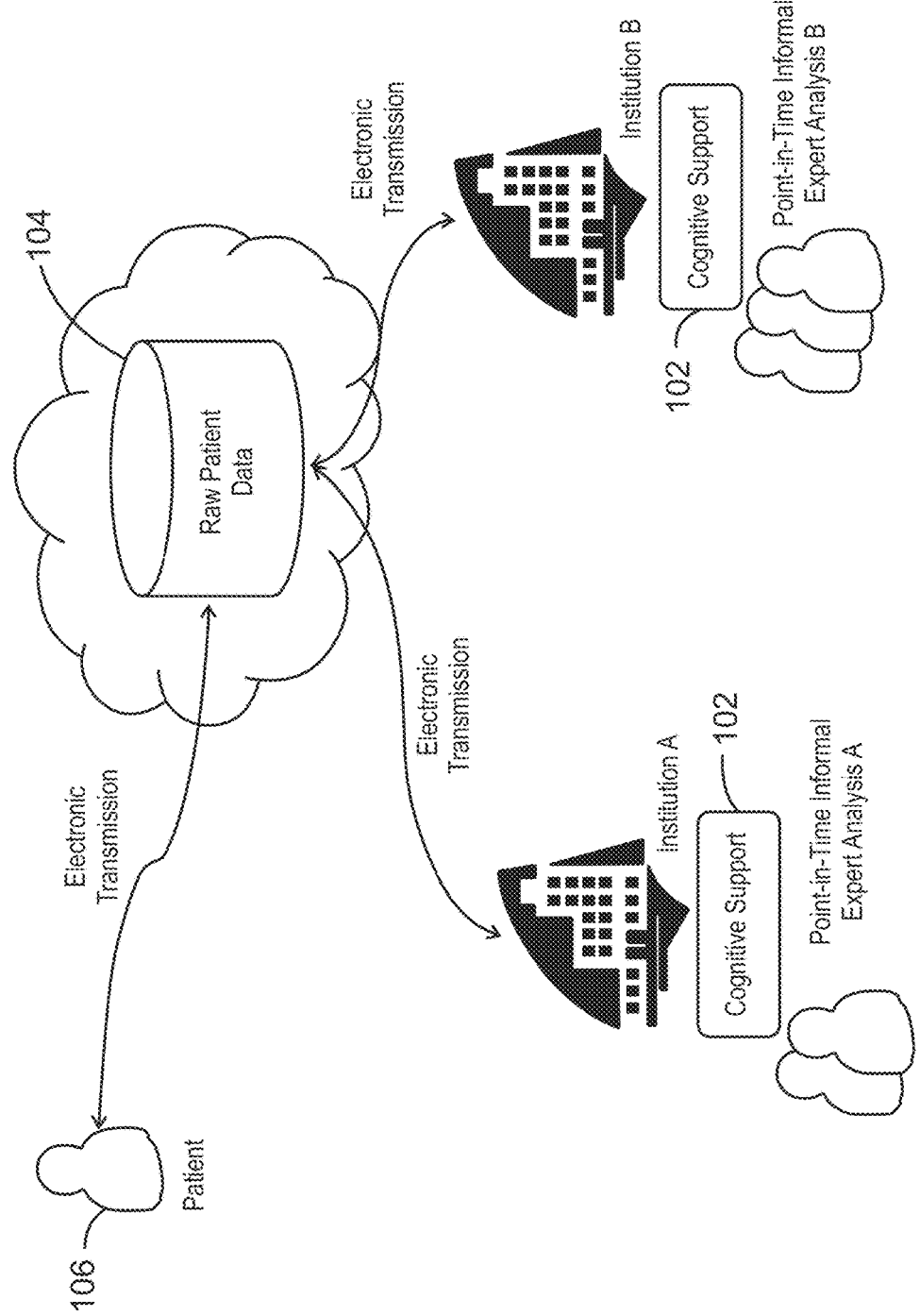
FIG. 1 depicts a conventional medical repository system with associated cognitive support.
Figure 2:
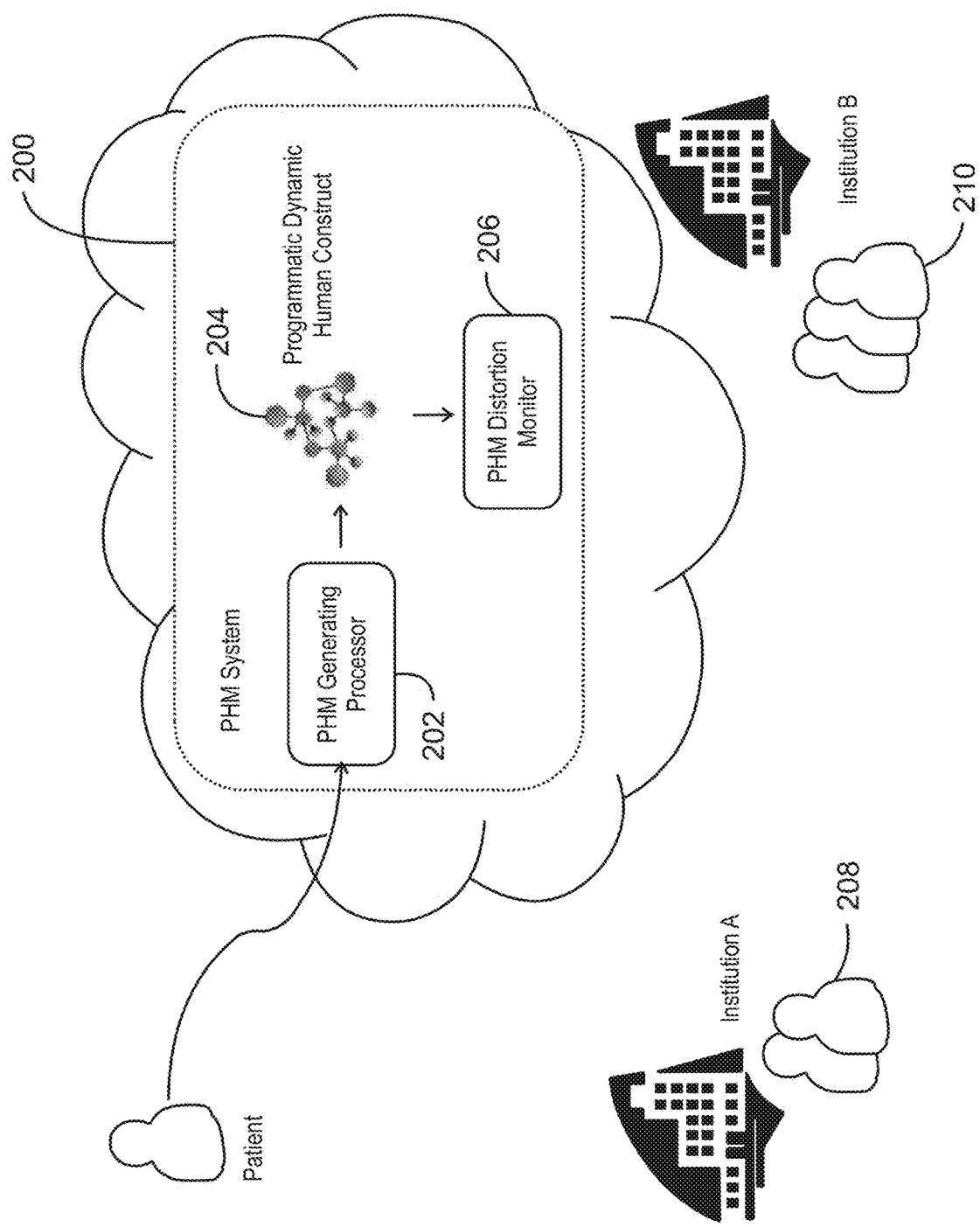
FIG. 2 depicts the PHM processor, some primary components, with input from patient data and access from multiple institutions.
Figure 3:
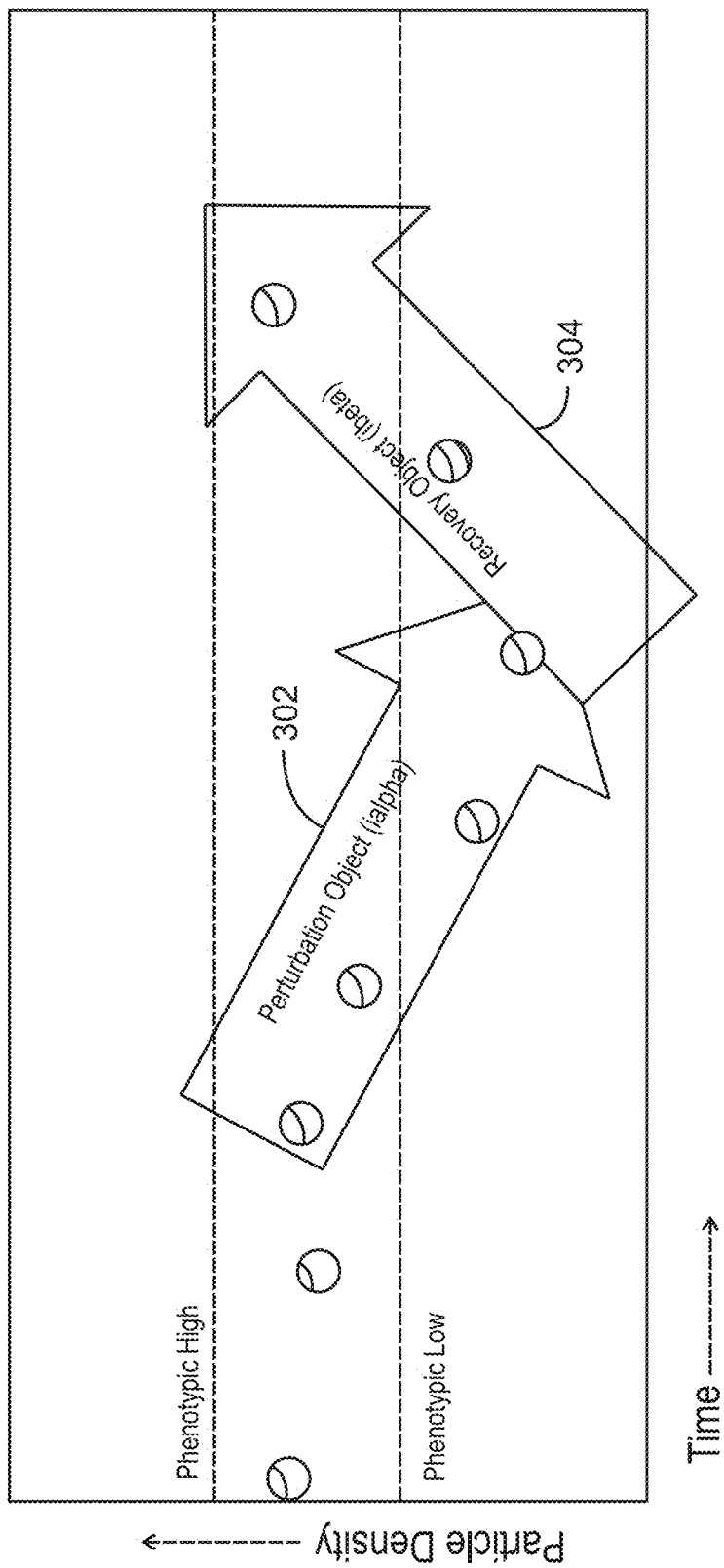
FIG. 3 depicts ialpha and ibeta events in a perturbation-recovery binary as accessed in i-space.
Figure 4:
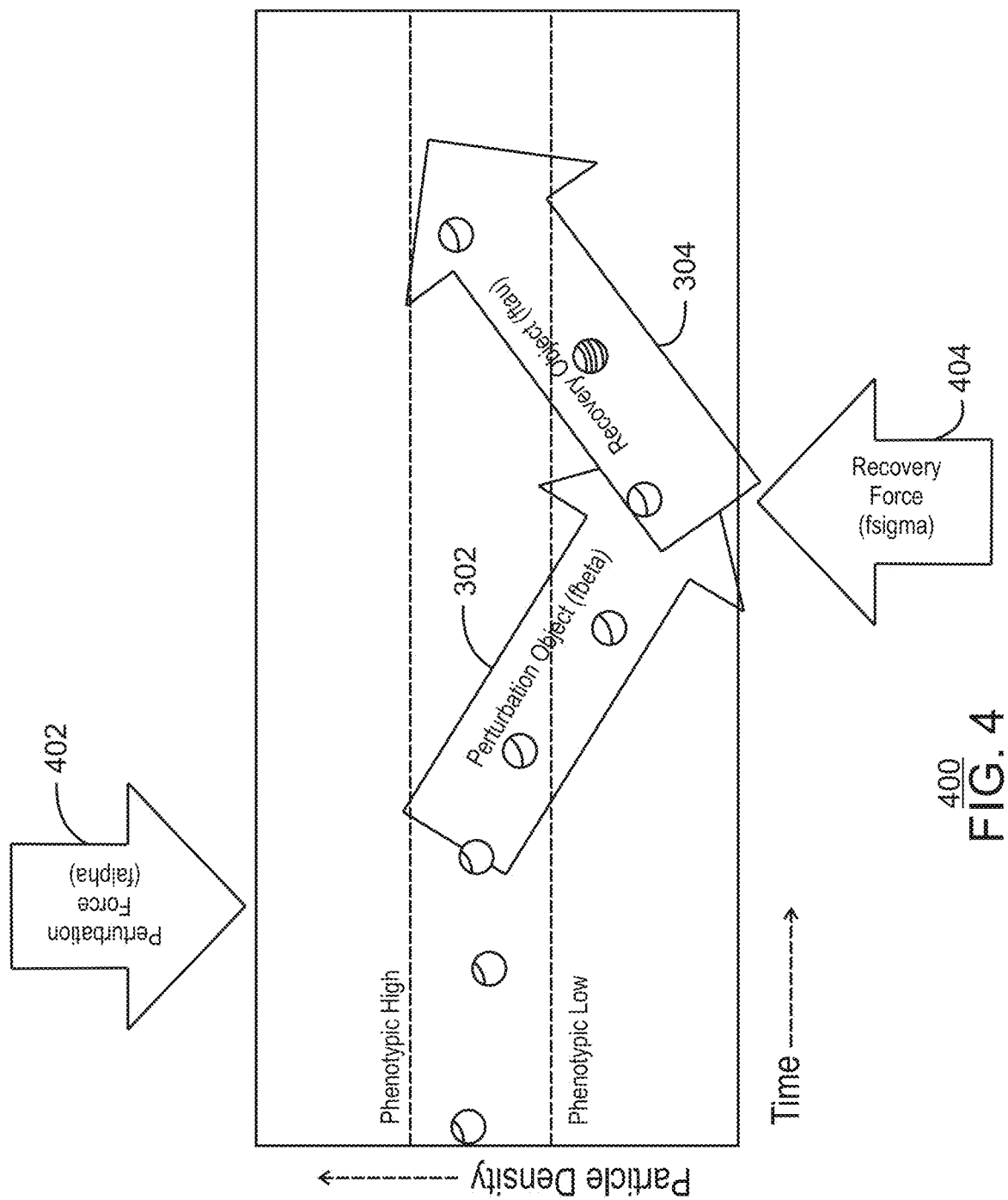
FIG. 4 depicts the same perturbation-recovery binary as in FIG. 3 as seen within f-space with perturbation and recovery forces depicted.

An embodiment described herein comprises a PHM system 200 of FIG. 2 that includes a processor (also referred to herein as the PHM generating processor 202 of FIG. 2) programmed to generate an image of causation of adverse conditions comprising a dynamic multi-dimensional parallel time construct (also referred to herein as a programmatic dynamic human construct 204 of FIG. 2) of a human or patient 206 from medical data which may be a causation construct which is comprised of perturbations and at least one force which caused or induced the perturbations. The dynamic human construct 204 exists in parallel with the human and provides a limited companion parallel instance of the biologic human. In one embodiments, the processor 202 can be programmed to analyze the parallel human construct 204 for dynamic distortions indicative of, for example, disease, drug reactions, age related declines in function, or other clinical failures. As constructed by the processor 202, one embodiment of the parallel human construct 204 is comprised of a highly organized and compartmentalized time matrix. The time matrix may be comprised of grouped, bonded, linked, related, encapsulated, or otherwise connected events and forces which may be converted to objects. In an embodiment, four fundamental events and forces which are used to build the time matrix are; perturbations 302 of FIG. 3 (such as particle density perturbations), perturbation forces 402 of FIG. 4 which induced the perturbations, recoveries 304 of FIG. 3 (such as particle density perturbations), and recovery forces 404 of FIG. 4 which induced the recoveries. In one embodiment, when linked these form a "force quaternary" (which is shown in FIG. 3). A force quaternary may be a fundamental repeating structural component of distortions along at least one portion of the PHM. According to some embodiments, this type of distortion of the biologic matrix is called a "polyquaternary distortion". A polyquaternary distortion 400 may, as shown in FIG. 4, be modeled as a growing molecule which develops upon the occurrence of a force sufficient to induce a perturbation 302 in the PHM and initially occurs in the region of the PHM which initially receives the force. If the perturbation force 402 is strong it may induce perturbation force cascade which projects through the particle densities of the PHM and expanding outwardly in the PHM to involve a progressively greater number of particle densities and a progressively greater number of systems. This comprises a causation construct or a causation cascade as the forces which induce or cause the perturbations define, with the perturbations, the construct which may be for example a causation time matrix. In cascading conditions such as sepsis, the perturbation force cascade may project along and within the PHM as a cone. The perturbation force 402 which induced the cone is called an apical perturbation force and is one of the causation forces of the cascade. There may be more than one force which comprises the apical force. The apical force (which may be endogenous or exogenous) may have been induced or more exogenous trigger forces.

In one embodiment, stasis, as well as perturbation 302 and recovery objects 304 are identified, related, aggregated and stored. Stasis objects represent and quantify the maintenance of particle densities within phenotypic ranges. Stasis object provide a positive representation of equilibrium within the system. Further stasis objects can provide quantification of the equilibrium. In one embodiment, stasis is quantified simply by referring to sections of the time series in which there are no perturbation or recovery events. In this approach a matrix in stasis is free of perturbation and it is the distortions which are defined by the force quaternaries. In another embodiment, stasis objects are defined by the normal forces which maintain the stasis object in its normal state, which may be a variable state, such as a cycling state. In this embodiment, a perturbation may be a physiologic perturbation or pathologic perturbation and recovery may be physiologic or pathologic. In this approach, recovery may be physiologic recovery from a physiologic perturbation, physiologic recovery from a pathologic perturbation, or a pathologic recovery from a pathologic perturbation. With this approach the entire matrix may be defined by quaternaries to the extent that the forces are known or reasonably assumable based on the dynamic motion image of the matrix.

In one embodiment, stasis objects are used as building blocks which may represent, at a higher level, physiologic perturbation and/or physiologic recovery. For example, rises, falls and reciprocations in chest wall pressure may be stored in terms of stasis objects if within phenotypic ranges. However, in the context of other objects these objects may represent or participate in relational objects that indicate either pathologic or physiologic perturbation or recovery. In this way, stasis objects provide the encapsulation of state, and change in state, which can be interpreted within the wider context of the entire matrix.

In one embodiment a recovery or perturbation may also be defined as exogenous, endogenous, or mixed depending on the force which induced it. For example, an exogenous recovery can be so designated when the recovery is actually derived from outside force (such as the administration of platelets causing a recovery of platelet density. In this example the recovery force (for example infusion of 6 units of platelets over 30 minutes), is an exogenous force and the platelet rise (recovery) responsive to the platelet infusion is an exogenous recovery. A grouping of recoveries which comprise recoveries associated with a polyquaternary distortion may be combined to generate a cascade of recoveries and recovery forces. If this group is endogenous, this group or cascade may be rendered as a motion image in a visualization as for example a motion image of a recovering storm which provides a different visual designation then the perturbation and perturbation force portion of the storm and a different visual designation then exogenous recoveries and exogenous recovery forces. In this way grouping or cascades of recoveries which are exogenous or single recoveries which are exogenous, may be identified in the matrix visualization with a different color or other marking so that they are not confused with endogenous recoveries by the healthcare worker. In the matrix visualizations, each of the above different types of perturbation and distortion and each different type of recovery may be designated by different colors or by other designations.

In one embodiment the processor 202 detects and analyzes perturbations to detect the presence of a distortion of the PHM. Upon identification of one or more perturbations, the processor 202 seeks to solve the quaternary, diquaternary and/or polyquaternary which comprise the distortion. The occurrence of a high and sustained force (as, for example induced by a biologic invasion by multiplying bacteria) induces at least one expanding polyquaternary. Since different types of distortion of the PHM, as for example caused by different disease types, produce different polyquaternaries, the processor 202 solves the polyquaternary by building it, as by the identification and insertion of a progressive number of its components into a diagnostic construct of the matrix distortion which optimally includes detection of the apical force or forces and any exogenous triggering force or forces.

Perturbations may comprise, for example, the perturbation of particle densities, perturbation of phenotypic energy states (as, for example, implied by temperature), the introduction of foreign organisms, the perturbation, reduction and/or elimination of health enhancing organisms, the perturbation of standard motions (including variations such as pulsations and oscillations), the damage to structural integrity, the perturbation of structural and/or functional capacity, the perturbation of the mental state of the patient to name a few. The presence of abnormally high or low diagnostic values (such as low or high particle density values) may also comprise and/or be considered indicative of the occurrence of a perturbation and may be substituted for a perturbation in the matrix groupings of perturbation force, perturbation, recovery force, and recovery.

According to some embodiments, the state of health or disease of any human may be definable as a function of the distortions along his or her PHM. Although many types of perturbations and forces may occur, a portion of the PHM is comprised of the densities of biologic particles. Distortions comprised of dynamic perturbations and recoveries of those densities, and the dynamic forces acting on those densities represent some of the dangerous and diagnostic distortions of the PHM. The detailed approach to identification of particle density perturbations, forces, quaternaries, and polyquaternaries along the PHM provided herein provides examples for application to other types of perturbations, forces, quaternaries, and polyquaternaries.

According to one aspect of some embodiments, (as shown in FIG. 2) the parallel instance (which may be include distortions comprised of solved and unsolved quaternaries) is monitored by a processor 202 for health and disease along with the biologic instance. The parallel instance may exist in the cloud, on a server, or another repository. As the parallel instance ages and new data are added the instance grows incorporating the new data in such a way that the past instance at any time may be accessed and/or fully reconstructed.

The parallel human construct 204 comprises a global integrated matrix called a "Parallel Human Time Matrix" (PHM). The matrix is constructed by a "PHM generating processor" and may be maintained in memory or persisted to storage as needed. The PHM is "grown" and "aged" over time over the life time of the human from which the construct is generated.

Since particle densities and patterns of particle densities in the PHM are forcefully maintained by density normalization forces a density change suggests either the loss of that normalization force(s), and/or the introduction of a new force that has overwhelmed the normalization force. Either condition comprises the equivalent of the introduction of an unbalanced density modifying force into the PHM which moves the particle density in the PHM to a new higher or lower value which generally will extend outside the phenotypic range producing a distortion of the PHM.

The PHM may integrate genetic code, and a sequenced human genome or a single gene may be positioned at the beginning of the matrix (for example as steps functions) when available. Genes or specific genetic codes or mutations, can be converted to objects and processed by the processor 202 as relational objects along the matrix and compared with particle densities, perturbations, distortions, and recoveries to identify relationships across populations between genetic information and the objects of the matrix. The PHM may further integrate particle densities, exogenous forces, endogenous forces, perturbations, and recoveries, as well as structural relationships, such as anatomic relationships. The PHM matrix may be an objectified time series matrix or another matrix construct. The PHM is monitored by a "PHM monitoring processor" (also referred to herein as a PHM distortion monitor 206). The PHM monitoring processor 206 may be the same general processor as the PHM generating processor 202 and when combined they are called collectively a "PHM processor" or "processor" or PHM system 200.

The PHM monitor 206 comprises a processing system and method which analyzes the complex and voluminous medical data sets which comprise a PHM. The analysis comprises detection, identification, quantification, and tracking of cascading perturbations, the forces inducing the cascading perturbations, as well as triggering events (such as a surgical procedure) which may have induced the forces. The processor also searches for the "apical force" 700 of FIG. 7 which comprises a force sufficient to generate a severe distortion of the PHM (for example by inducing a force cascade (which may be a force polyquaternary cascade) within the PHM. The apical force 700 or forces (for example invasion of the human by bacteria) generally precedes the force cascade (and is positioned in the matrix at the apex of the force cascade). The apical force 700 is often a diagnosis such as "group A streptococcal bacteremia". In one embodiment, the apical force 700 is a relative concept specific to a perspective selected by the viewer. For example, a user may be interested in the apical force 700 within a clinical space.

The analysis further comprises detection, identification, quantification, and tracking of cascading recoveries, and the forces inducing cascading recoveries. The PHM monitor analyzes the data from the PHM to generate outputs which may comprise dynamic motion images of force cascades over time. The PHM monitor may generate images which present the relational complexities of the force cascades along the PHM in dynamic formats which are readily understood, such as a color radar weather-map format.

A PHM may be comprised of any suitable amount of the medical data and/or related medical expense data available for a given patient from the onset of data collection (before or at the time of birth) and forward. The entire matrix back to its point of origin may be constructed and analyzed by the PHM monitor for distortions and the PHM may be viewable in relation to time as a time-lapsed motion image through the use of a PHM visualization processor which generates motion images of the PHM in a range of dynamic formats including, for example a color weather radar format as for example described in the co-filed application, "Patient storm Tracker and Visualization Processor".

Each individual, or the individual's parents or guardian, may possess their own PHM as well as the PHMs of their children or of individuals under their guardianship. This will give each individual, parent, or guardian, much more control over their healthcare. Individuals may store their own updatable PHMs, either partially or as a whole, on memory storage device such as flash memory card which may, for example, be integrated with their driver's license or another storage device such as a hard drive, or a secure access cloud site. The PHM generator may be programmed to automatically update a PHM on a storage device when the device is connected with the PHM generator.

The individual PHM of each patient in a healthcare system may be stored in the cloud where each may be updated when new data is available. The healthcare system may deploy one or more PHM monitors to monitor each of the PHMs in the cloud whether the client is in the hospital or not. An individual may choose to have the raw data (which is preferably stored as part of the PHM), the PHM itself, and/or the output of the PHM monitor reviewed by an expert physician on a periodic basis and to update the PHM or correct the configuration with her or his expert input.

The time-lapsed representations of a personal PHM may be animated in a range of alternative formats and viewed on a device such as a smart phone, iPad, Galaxy tablet, or Surface tablet to name a few. At least one animation is preferably readily understandable by individuals without medical training. Individuals may view their own PHMs or those of their children from the storage site using a PHM visualizer. PHMs may be updated while a patient is in the hospital or emergency room as by secure smart phone, password protected Wi-Fi or other secure transmission, so that the individual, parents, or other approved family members are updated in a manner wherein they may readily seek alternative PHM review, an alternative PHM monitor, or expert who may be remote for the hospital.

According to one aspect of some embodiments, although the PHM may function as a comprehensive medical data repository for each individual, it is actually a dynamic, growing, and highly portable, parallel representation of the dynamic state of health and/or disease of the represented individual within the limitations of the available data Like the individual, the PHM may be continuously or periodically updated and monitored to determine the PHM's state of "health".

In one embodiment, the PHM processor 200 monitors the parallel patient construct (the PHM). Both the healthcare workers and the PHM may monitor the actual biologic patient, asking questions, applying tests, and physical evaluations, updating the PHM and the healthcare worker. In addition, both the PHM processor 200 and the healthcare workers from Institution A 208 and Institution B 210, among others, monitor each other to optimize quantity, timeliness, and efficiency of care. The PHM, upon identifying a distortion comprised of abnormal physical findings, test result, and/or historical finding, the PHM may identify linkages and images which comprise primers of the image of the distortion and upon the detection of one or more primers, generate one or more questions for the patient, or ask the healthcare worker to examine a physical portion of the patient, the answers and/or results to which may help improve the image in the PHM. At the discretion of the healthcare worker or when the worker is not available, the PHM may ask the patient directly in text or voice or the PHM may offer the questions to the healthcare worker so that he or she may ask them. In this way the PHM processor 200 uses dynamic image primers of specific distortions (or the lack thereof) to focus or expand the medical history and physical as well as clinical testing.

Figure 5:
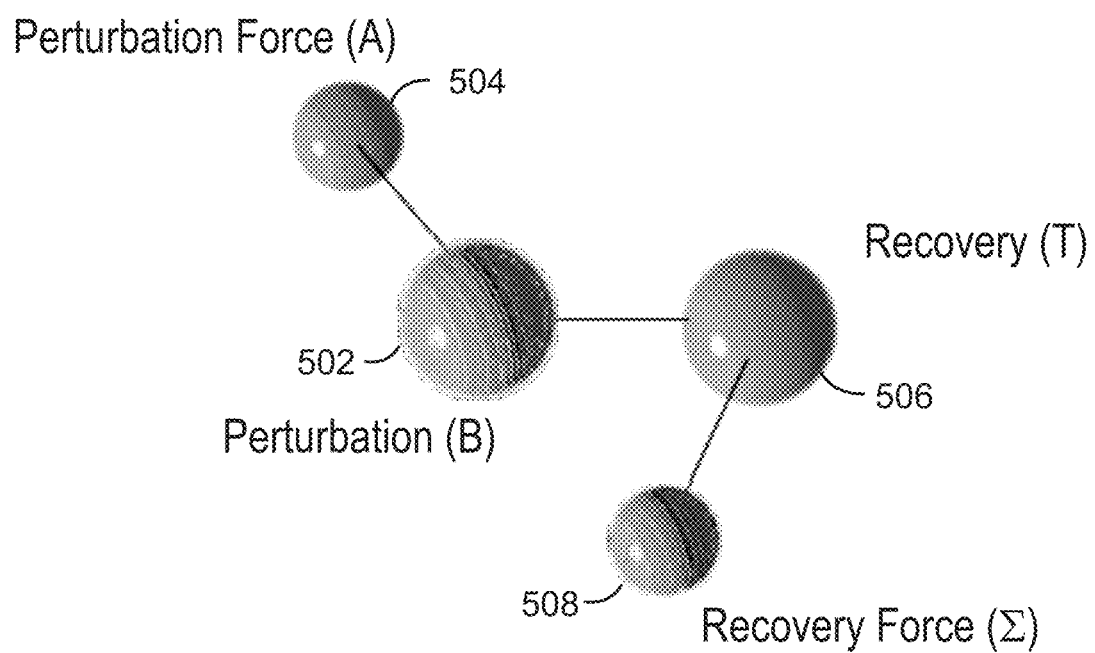
FIG. 5 depicts a single quaternary.

FIGS. 4 and 5 shows examples of basic "building blocks" comprised of perturbations and matched recovery, with matching forces, which define the fundamental building components (which may be objects) of the PHM. In one embodiment as shown in FIG. 5, the PHM processor 200 detects and link a set of at least 4 components of a distortion quaternary comprising, a perturbation 502, the matching perturbation force 504 (which is capable of inducing, and may have induced that specific perturbation), a recovery 506 (from the perturbation or in response to the perturbation), and the matching recovery force 508 (which is capable of inducing and may have induced the recovery). In one embodiment of the PHM, all of these components are converted objects that are linked in the timed sequence of their occurrence with the distortion itself being comprised of a solved or unsolved quaternary or polyquaternary. In one embodiment, each distortion is comprised of only one quaternary or polyquaternary and when two quaternary or polyquaternary are present they are either linked (and this link has not been detected) or there are two distortions. The processor 200 seeks a common link for (or a link between) the apical forces (or another force or perturbation) of each polyquaternary or seeks common exogenous trigger force for each.

Figure 6:
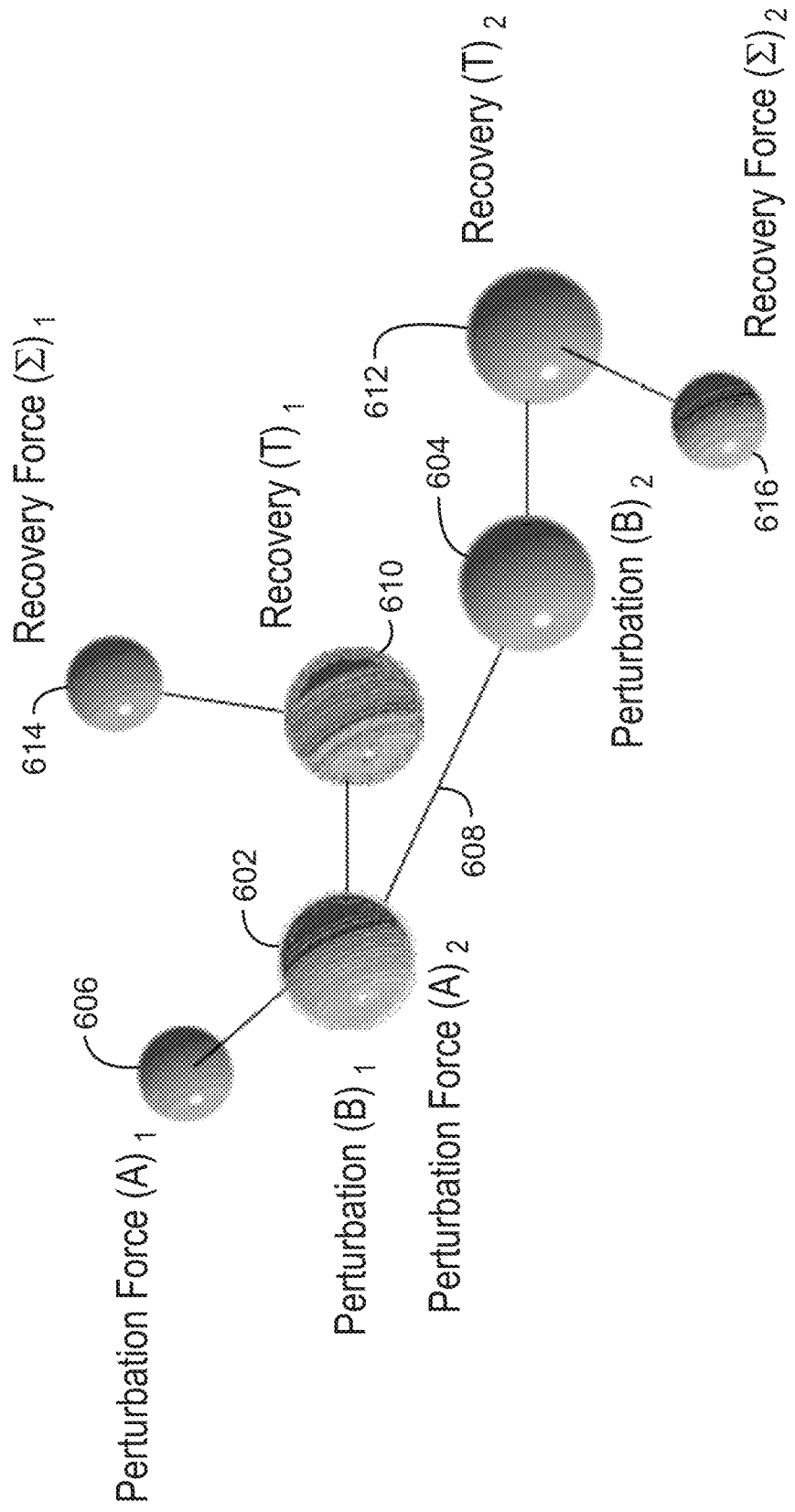
FIG. 6 depicts two linked quaternaries wherein the perturbation of the first quaternary is the perturbation force of the second quaternary.

The PHM generator may use combinations of each of these objects and particular the combination of all four of these objects to build or "grow" the distortion by linking additional groups of these objects as shown in FIG. 6. As shown in FIG. 6, the perturbation of one grouping may be the perturbation force of a second grouping as these are detected and linked the processor 200 generates a force cascade of perturbations and forces which mirrors those operative in the patient. As will be discussed there will be gaps in the distortion but one goal is to build the image sufficiently to detect the primary cause of the distortion such as a "force-cascade precipitating force", which is generally an apical force 700 (designated as such as it generally exists (or existed) near the origin (the apex) of the expanding force cascade which comprises the distortion as shown in FIG. 7.

Figure 7:
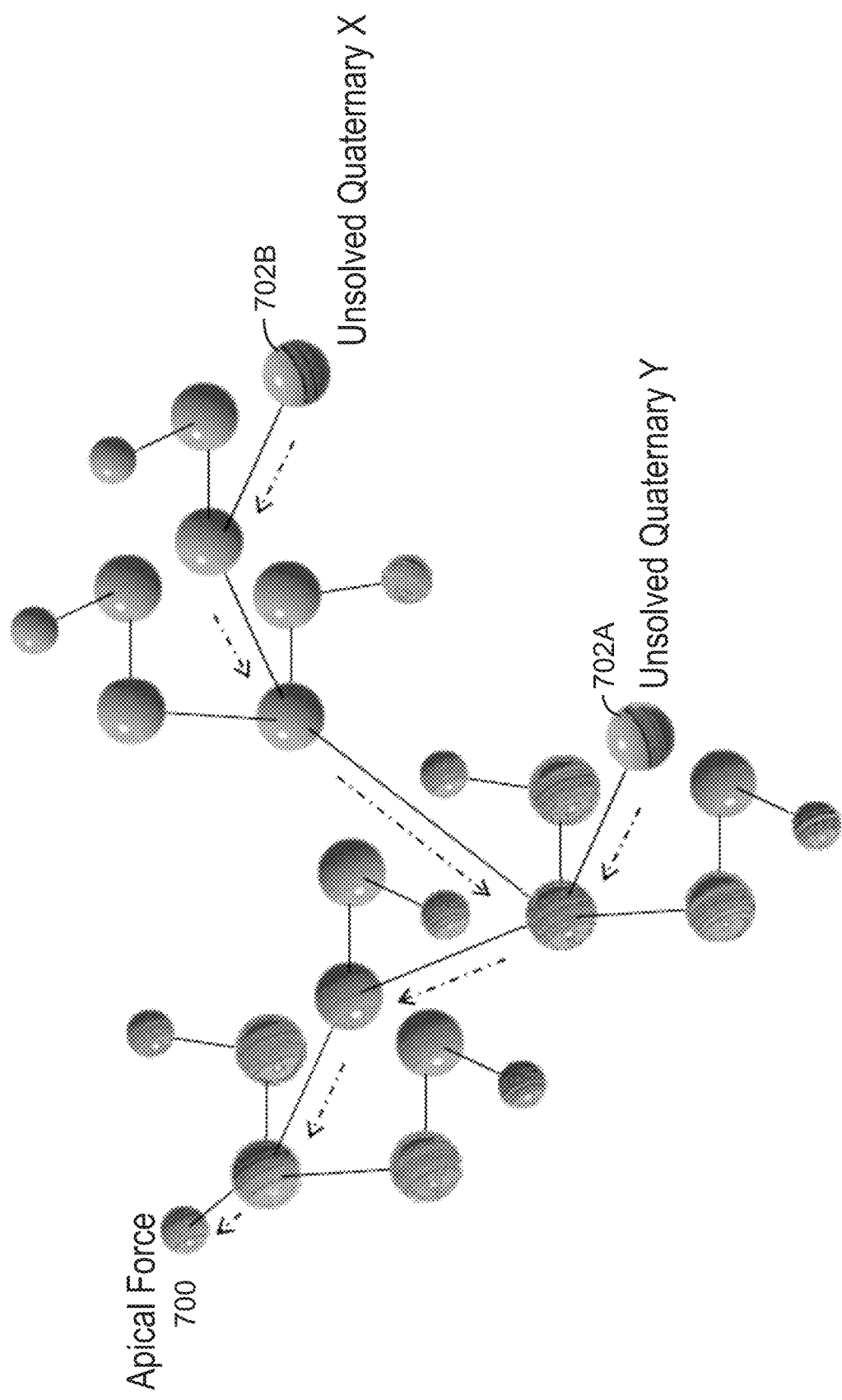
FIG. 7 depicts a polyquaternary distortion with many linked quaternaries including 2 unsolved quaternaries and a single identified apical force comprising an image of causation.

FIGS. 6 and 7 show linked polyquaternaries. The example illustrated in FIG. 6 includes perturbation B1 602, perturbation B2 604, perturbation force A1 606, perturbation force A2 608, recovery T1 610, recovery T2 612, recovery force Signal 614, and recovery force Sigma2 616. However, typically, during early distortions in the PHM due to an unknown but dangerous process, only perturbations are initially evident along the distortion and the polyquaternary 600, which will in the future, when solved, identify, quantify, and define the distortion is incomplete. In an example, it is typical of in early sepsis before the diagnosis is made by the clinician or processor 200 for the distortion of the PHM to comprise only perturbations although many of these will be compensatory perturbations which mitigate movement of critical densities away from normal values. In other words, in early sepsis the FIGS. 6 and 7 would be comprised almost entirely of perturbations.

One of the purposes of the PHM processor 200 is to solve the polyquaternary as soon as reasonably possible since upon the solution of the polyquaternary the processor 200 may be able to render a diagnosis, quantify the condition, project a "near worst case" path of at least part of the distortion, and provide direction for treatment or treatment modification. In many cases the processor 200 may solve the polyquaternary with only perturbations, inserting the forces, and especially the apical force when the processor 200 has solved the polyquaternary and determined its identity. The completed distortion is generated when the polyquaternary has been solved although there may be missing forces and particularly recovery forces if the polyquaternary has not yet extinguished along the PHM. Many of the cascading forces may be completed by the processor 200 when the apical perturbation force is solved and the diagnosis made. The time pattern of the recovery force may be used by the processor 200 to characterize the recovery patterns of the polyquaternary distortion.

Along the polyquaternary, relational timing of the apical perturbation force, treatment potential triggers, treatment, identification and the durations, including of the expansion and contraction portions of the polyquaternary are all defined to determine quality of care. The polyquaternary is displayed, for example in relation to time, to illustrate the timing relationships.

The PHM monitor is programmed to detect dynamic distortions in the PHM, and generate processing decisions. Collectively a unified PHM processor 200 may perform all of these tasks. The PHM processor 200 may link two of the four objects such as a perturbation objects and the matching perturbation force object, or the recovery and the matching recovery force, or the perturbation and the matching recovery from or in response to the perturbation, or the perturbation force and the recovery force which induced the recovery from the perturbation induced by the perturbation force, or the perturbation force and the recovery from the perturbation, or the perturbation and the recovery force which induced the recovery from the perturbation, as well as three or all four combined components as decision points (such as the ordering of additional testing), or decision components, and also to link to other events or combined components.

In one embodiment, (as shown in FIG. 5) the PHM processor 200 links the quaternary and then uses the quaternary as a "primer" to build a polyquaternary. However, as noted, the processor 200 may only have one or more of the perturbation objects available to use as the primer. The PHM processor 200 may be programmed to, upon detection of the primer, complete the image by linking available data or to order additional testing to complete the image.

The PHM processor 200 may combine a perturbation object with a perturbation force object to generate a "perturbation force binary" object. The PHM processor 200 also may combine a recovery object with a matching recovery force object to generate a "recovery force binary" object. These two binaries may be combined by the PHM processor 200 to generate the "perturbation-recovery force quaternary" of FIG. 4. These force binary objects and force quaternaries may be linked to other binaries and quaternaries to build highly complex, time dimensioned images. The PHM processor 200 may then construct very large and highly complex force cascades, such as sepsis force cascades of; triggering exogenous perturbation forces, (such as a surgical procedure), endogenous perturbation forces, perturbations, and exogenous recovery forces (such as an antibiotic or surgical intervention), and endogenous recovery forces, using basic binaries, the quaternaries, and/or individual events or forces. The PHM processor 200 may also create and use trinaries, or other basic building objects which combine multiple objects. The PHM processor 200 may then generate motion images of the force cascades of objects comprised of perturbations, recoveries, forces, binaries, quaternaries, diquaternaries and polyquaternaries, which may comprise a distortion or set of distortions of the PHM.

The processor 200 may be programmed to provide processing systems and methods, which analyze dynamic pathophysiologic force cascades of perturbation of the densities of biologic particles and recoveries of the densities of biologic particles (and particularly force cascades of perturbation and recoveries of densities of biologic particles induced by sepsis), along with associated individual, relational and force cascades of the forces inducing the perturbation and the forces inducing the recoveries of the densities, and for presenting the force cascades of the perturbation and recoveries as well as the perturbation forces and recovery forces in a motion picture responsive to or indicative of force cascades of perturbation, which may be linked to force cascades of perturbation inducing forces, which may be linked to force cascades of recoveries, and which may be linked to force cascades of recovery inducing forces.

The processor 200 may be programmed to identify those perturbations or recoveries for which the processor 200 does not identify the perturbation inducing force and/or the recovery inducing force. In one embodiment the processor 200 is programmed to identify those force cascades of perturbation and/or recoveries for which the processor 200 does not identify the force cascades of perturbation inducing forces and/or force cascades of recovery inducing forces.

The processor 200 may be programmed to identify those perturbation inducing forces and/or the recovery inducing forces for which the processor 200 does not identify the perturbation and/or the recovery which the forces are expected to induce. The processor 200 may be programmed to identify those force cascades of perturbation inducing forces and/or force cascades of recovery inducing forces for which the processor 200 does not identify the force cascades of perturbation and/or the force cascades recovery which the forces are expected to induce.

The processor 200 may be programmed to analyze (which comprises for example, detection, identification, quantification, and/or tracking) the individual perturbations and/or force cascades of the individual perturbations and to analyze the individual perturbation inducing forces which induced the individual perturbations and to link and/or link in a output or display, the individual perturbations which are induced by the force and the force cascades which are induced by the force or induced by a force cascade of forces.

The processor 200 may be programmed to analyze and link individual perturbation inducing forces, to individual perturbations, and to individual recovery inducing forces and to individual recoveries. The processor 200 may be programmed to link the individual recoveries to the individual perturbations which are reversed or corrected by the individual recoveries, and to analyze at least one force cascade of perturbations and at least one force cascades of perturbation forces and at least one force cascade of recoveries and at least one force cascade of recovery forces.

The processor 200 may be programmed to generate a linkage chain or a temporal cluster of linkages and to link a perturbation and/or a force cascade of perturbations to a perturbation inducing force or a force cascade of perturbation inducing forces, and further to link a recovery and/or a force cascade of recoveries, which reverses or corrects the perturbation and/or force cascades of perturbations, to the force or cascades of forces inducing the recovery and/or force cascades of recoveries, link the perturbation and/or force cascades of perturbations to the recovery and or force cascades of recoveries, link the perturbation inducing force and or force cascades of perturbation inducing forces, to the recovery inducing force and/or force cascades of recovery inducing forces. The processor 200 may be further programmed to link other events, such as for example exogenous actions and/or genetic information to at least a portion of the linked chain or spatial and/or temporal cluster of linkages.

The processor 200 may be programmed to analyze a sepsis force cascade, its onset (which may comprise the onset of early inflammatory augmentation), its evolution, its expansion, its peak, and its recovery in relation to endogenous forces, such as perturbations in biologic particle densities or organ dysfunction, as well as exogenous forces (such as exogenous actions) such as surgery, central line placement, initiation of intravenous nutrition, antibiotics, to name a few. The processor 200 may be programmed to link the force cascades to other factors or objects such as the healthcare worker, hospital location, cost of care, to name a few.

SUMMARY

In one embodiment the PHM is comprised of the following components:

A first objectified time series sub matrix (called a "phenotypic sub matrix") comprised of the objectified phenotypic densities of biologic particles during health;

a second objectified time series sub matrix (called a "perturbation sub matrix") comprised of objectified perturbations of densities of biologic particles;

a third objectified time series sub matrix (called a "perturbation force sub matrix") comprised of the objectified forces inducing the perturbations of the second sub matrix;

a fourth objectified time series sub matrix (called a "recovery sub matrix") comprised of the objectified recoveries of the biologic particle densities from the perturbations of the second sub matrix;

a fifth objectified time series sub matrix, (called a "recovery force sub matrix") comprised of the objectified forces inducing the recoveries of the fourth sub matrix;

and a sixth objectified time series sub matrix (called a "chronically distorted sub matrix") which contains objectified densities of biologic particles which, after being perturbed, have remained persistently different from their phenotypic densities.

Each of these matrices may have a companion objectified expense matrix for incorporation into the PHM. Additional objectified time series matrices, for example comprised of the forces (which may be genetic code) inducing the densities of biologic particles of the phenotypic matrix and/or stabilizing the particle densities of the phenotypic matrix may also be provided. Any or all of these sub matrices may be analyzed or viewed separately or as components of a unifying PHM.

Historical information and subjective symptoms may be included as step functions in the PHM. In an alternative embodiment, historical information is entered as externally supplied events. In an example, an input of a historical symptom of diarrhea "lasting for a week about one month ago" could result in this symptom being added to the PHM at the time subjectively specified. The patient could enter this information with the PHM being built as the patient answers the questions about medical history and symptoms. Subjective times may be given a range, which may be a fuzzy range, in the PHM. In an example, the object diarrhea as subjectively specified above is marked with a range of time rather than a specific time. During an analysis of the PHM subjective times are defined by their ranges. The PHM processor 200 may be programmed with additional supplemental questions to provide greater clarification and specificity to a positive answer (like the presence of diarrhea). Annotations may also be embedded in historical objects, for example a narrative of the history of the chief complaint may be embedded as a digital, read only, or other file in the PHM with linkage to the time to which the history references and the time it was acquired. In an example if a patient indicates that he or she developed diarrhea on a particular date, the onset of diarrhea may be inserted into the matrix at the time specified but with a subjective flag indicating that the data is subjective and may not be highly reliable. The subjective history of the chief compliant and the medical history may be incorporated by the processor 200 into the matrix building a matrix which includes a timed medical history at the times wherein the historical events actually occurred (as subjectively or objectively determined). In this manner the PHM processor 200 projects the PHM back in time, filling in gaps along the historical matrix with subjective symptoms, diagnosis, and physical findings. In one embodiment subjective physical findings are incorporated into the matrix at the time they are discovered and/or they placed at a time along the matrix when they were discovered if the physical findings were present in the past. Subjective physical findings may be recovered as step functions in the matrix. If they are quantifiable a numerical scale suitable for subjective granularity may be included (for example 0-5 for normal, marginal, mild, moderate, severe, profound).

While portions of this historical narrative (called "hot" portions) may become timed structural objects of the PHM (from which force, perturbation, and recovery analysis as described herein may be performed), the narrative itself may be stored in the PHM with the portions which are "hot" also representing hot links from the narrative to their timed positions in PHM. A similar approach may be taken for tests such as an echocardiogram, chest radiograph, or CAT scan. The "hot" portions from these studies are added to the PHM while the narrative reports are also embedded in the PHM at the time of acquisition. Examples of hot portions in the report may include the presence of a diagnosis and any numerical, measuring, scoring, or grading, (such as the presence of heart failure with lung congestion severity grade 2 of 5, cardiothoracic ratio of 0.6, a left ventricular ejection fraction of 0.24). The digital studies are also embedded in the PHM (for example, as read only or interpretable files) accessible through the PHM or the hot links in the narrative.

The ability of a physician or other worker to perform program assisted or unassisted interpretation of such studies is greatly enhanced by the availability of the PHM in relation to the study at the time of interpretation. In one example, the interpreter, or the processor 200, in response to the interpretation, may add links to events, binaries and/or force cascades in the PHM thereby assisting the processor 200 or healthcare worker in interpretation of the clinical relevance of the findings of the study to the global PHM. As with the PHM assisted history and physical examination, the PHM, upon identifying primers comprising, for example, findings in the study linked to relevant images in the PHM, may generate one or more questions for the interpreter, the answers and/or results to which may help improve the image in the PHM. At the discretion of the interpreter, the PHM may ask the interpreter directly in text or voice. In this way the PHM processor 200 uses dynamic image primers (or the lack thereof) to focus or expand the interpretation of clinical tests such as chest radiographs, CT scans, electrocardiograms, echocardiograms, or peripheral blood smears to name a few.

One example of a hot portion of a study is a result or finding which warrants detection of the force which caused the result or finding or which warrants detection of recovery or stability of the test or result. For example, a finding of a cardiothoracic ratio of 0.6 results in a detection of the force (for example, heart failure, pericardial effusion, cardiomyopathy, or valvular heart disease) which caused the high ratio. A high cardiothoracic ratio is therefore a hot portion of the chest radiograph interpretation and comprises an theta for which the processor 200 will seek an falpha and designate the binary as unsolved if an falpha is not identified. The processor 200 may also be programmed to expect hot portions in the interpretation (in this example, an indication of the measured cardiothoracic ratio) and to consider the interpretation incomplete if a hot portion is missing. The processor 200 may be programmed to send a notice to the interpreter to complete the hot portion or to warn before saving of the interpretation that a hot portion is incomplete. The processor 200 based potential linkages may proceed in real time and may displayed with the relevant segment of the PHM for the interpreter as in a window, as he or she dictates or enters the interpretation. In an example, the identification of the high cardiothoracic ratio may link to a high brain naturetic peptide (BNP) result, a low left ventricular ejection fraction, a pericardial effusion identified on a chest CT scan, and/or a high blood pressure result. These real time linkages do not indicate cause and effect but rather are parts of the dynamic image of the PHM.

An PHM may be generated which is comprises of all the data, narratives, reports, objects, and sets for which medical related data is available, from the beginning of data acquisition to the point of analysis. In one embodiment, the PHM is constructed as a single integration, comprised of all the objects and time series of objects available. The PHM comprises a medical records repository of linked objects comprising, perturbation forces, perturbations, recovery forces, and recoveries. The configuration and distortions of the PHM and its objects are monitored and analyzed to detect disease, drug reactions, recovery, the need for additional testing or treatment, etc.

The PHM may be divided into compartments or regions. A region of the PHM may be comprised of a set of time series of objects which relate to a specific organ or system. In one embodiment, the PHM is a large compartmentalized matrix dynamically changing in configuration in response to continuous or intermittent flow of medical data. According to some embodiments, the dynamic states of human disease are analyzed by the PHM monitor and outputted to health care workers as direct function of the detection and analysis of dynamic distortions of the PHM.

The PHM is constructed so that the biologic forces and biologic particle densities are highly interrelated. Furthermore, the particle densities and forces are substantially all potentially linked, or otherwise connected to each other in the PHM. For this reason, a new perturbation or a new perturbation inducing force in one region of the PHM will generally induce a dynamic distortion of the PHM which may extend to other regions of the PHM. This distortion will push or pull on other connected portions of the PHM causing secondary, tertiary, and at times cascading dynamic distortions along the PHM. These distortions (as comprised of polyquaternaries) are linked, and the processor 200 is programmed to follow and build the distortions and the motion image of and/or responsive to the linked distortions, and to output the motion image.

Pathologic PHM distortions are not present or are minimal in health. However, physiologic distortions of the PHM are normal in health, as during exercise, or stress. These physiologic, time-dimensioned distortions extend along anticipated regions of the PHM from perturbation force, to perturbation, to recovery force, to recovery, each linked in the PHM to each other to generate a complex physiologic PHM distortion. This distortion may be a "physiologic polyquaternary". A time segment portion of the PHM before a physiologic polyquaternary and after a physiologic polyquaternary is essentially identical whereas they are often different after a pathologic polyquaternary due to residual injury of the matrix.

As discussed in detail below, one embodiment comprises a PHM processor 200 which renders motion images derived from a limited PHM and/or the entire PHM. These images of the PHM may comprise for example, motion images of, indicative of, and/or responsive to a human phenotype or to PHM distortions. In one embodiment the distortions are outputted as complex, linked, cascading PHM distortions indicative of human disease and/or recovery from disease. The distortions may include linked images of objectified expense perturbations associated with the PHM distortions. Distortions of the PHM in one region may be compared with distortions of the PHM in the expense region.

The biologic particles which potentially comprise the PHM of some embodiments are vast in number and diversity. Yet, virtually all of these particles present in the PHM in high density relative to the environment. These particles comprise for example; ions, (such as; H+, K+, or Na+), endogenous molecules; (such as H2CO3, glucose, albumin or brain naturetic peptide); therapeutic molecules (such as levofloxacin, spironolactone, furosemide or cyclophosphamide); endogenous cells or other macro structures, (such as red blood cells, nucleated red blood cells, neutrophils, or platelets); and invasive particles (such as group A Streptococcus, lipopolysaccharides, Strongyloides stercoralis, peptidoglycan fragments, or bacterial DNA fragments).

The densities of various types of biologic particles in any given compartment of the PHM are generally different than the environmental density of that particle and often different than the density of the same particle in other compartments of the PHM. The relative particle densities in each compartment of the PHM are derived by clinical testing of human compartments (which may be invasive or non-invasive testing). Each patient has density defining forces which determine the densities of the biology particles under their influence. These density defining forces generally maintain each specific particle density at virtually a single density value, pattern of values, or within a very narrow density range. In health and the non-stressed state, the density range for each particle in each PHM compartment in relation to environmental and nutritional factors is specific to the genetic code of the individual human under test. Each patient generally has his or her own phenotypic density range for each biologic particle type in each PHM compartment. These phenotypic density ranges are much different than population defined "normal" densities. In one embodiment, the processor 200 determines the phenotype for the PHM compartmental densities of biologic particles by analyzing the phenotypic components of the PHM (derived in a state when the health of the patient and densities are at their resting baseline and wherein the densities are "unperturbed", for example, not acute or sub-acutely stressed) or of the phenotypic sub matrix.

One embodiment defines the phenotypic or population variability of a test around a measured value (which may, in some cases, be less than the inter-measurement variability due to the testing instrument itself. The patient's baseline and the phenotypic or population variability are used to define the phenotypically normal range for the patient rather than the use of the population normal range.

Each of the biologic particle density objects in the phenotypic sub matrix has, for example, the characteristics of absolute unperturbed density value, relative unperturbed density, and unperturbed density range, variability, and/or pattern. A phenotypic sub matrix may comprise a dynamic image of the densities of any or all compartments, physiologic systems, or physiologic grouping of cells. In one embodiment a segment of the PHM from a healthy young human at rest is used to define the future phenotypic values and ranges for future reference. The phenotypic ranges change as the patient ages and may be reassessed periodically.

As discussed, when defined statistically, the human population generally has a much wider range of so called "normal" particle densities than is defined by the unperturbed variability associated with any individual particle density phenotype. The common use of, for example, defining "normal" for an individual patient as a range of 2 standard deviation for the high limit of a population and a 2 standard deviation range for the low limit of normal of a population is incomplete. While the PHM may incorporate objects which relate to these traditional thresholds for reference, distortions of the PHM induced by these types of thresholds are considered along with the actual distortions in relation to the phenotypic ranges in the analysis process.

According to some embodiments, the phenotypic range for each density value is defined as the phenotypic range of the density value in a phenotypic sub matrix or when the PHM is undistorted by any active non-genetic force. The phenotypic range is ideally determined for each individual by making multiple measures over time but this is often not practical. For this reason, in one embodiment, the phenotypic range is determined by examining the individual ranges within individual phenotypic sub matrices of a large population. This range is then applied around the density value of the phenotypic matrix which is generated for the individual during a clinical state of health. The range may be defined by statistical methods but in this case it may for example, be the standard deviation of the individual ranges of unperturbed density variations in the population, rather than the standard deviation of densities in the population itself. Since the position of the density value in the range may not be known, an additional cushion may be added (such as one or two average deviations or standard deviations) to the high and low phenotypic range. Measurement of additional phenotypic densities, when available may be used to better identify the range and allow elimination of the cushion.

In one embodiment the PHM processor 200 is programmed to generate a large set of phenotypic populations sub matrices from healthy individuals during a non-stressed state of health and, analyze the sub matrices to define the phenotypic ranges of objects in the sub matrices and to define the phenotypic ranges of the unperturbed variability around the individual density values.

According to some embodiments, at least one phenotypic PHM distortion may be defined by analysis of a PHM distorted by a non-genetic force. This may be identified if a known perturbation force, such as a new or increased particle density of a drug, is introduced into the PHM and the perturbation induced by the force was within the expected range. The specific or general distortion of the PHM in response to the perturbation force induced by the drug may be defined as a specified force induced phenotype of that PHM.

Both the phenotypic sub matrix and the PHM distort with age but are often highly stable within periods of an individual's life. In one embodiment the rate of distortion with age of the phenotypic sub matrix and/or the PHM may be tracked and compared with other individuals or populations.

In one embodiment, the processor 200 defines human compartmental particle; densities, density perturbations, density recoveries, density rate of change, and density momentum mathematically by time series derived amplitude and slope formulae. The movement of a mass of particles into or out of a human compartment, or the consumption of particles within the compartment is inhibited by an aggregate resistance (modeled for the purpose of illustration as a human particle flux resistor) which is initially genetically defined and comprises a phenotypic density flux resistor. Particle flux resistance is particle and compartment specific and is initially phenotypically defined but may then be affected by disease, injury, environmental, nutritional, and/or aging factors. Particle flux resistance is a function of human systems, and may include a combination of factors such as membrane flux resistance, molecular buffers, molecular or ion pumps offsetting the flux, and organ compensation, to name a few.

Particle flux resistance may not be measured but is rather generally inferred by the time series pattern of the particle density in relation to the time series pattern of forces which potentially affect the particle density. These forces may or may not be detectable or measurable but are inferred as a function of particle density time series patterns. Low particle flux resistance may also be identified when particle densities which are stable phenotypically begin to vary widely (for example, oscillate) when no major exogenous forces are active. One example of this is the development of oscillation of oxygen molecules in the arterial blood compartment which may occur in association with severe decline on left ventricular function. In this example resistance to particle density flux (of arterial oxygen particles) has declined due to loss of sufficient flow rate of arterial blood. A normal arterial blood flow rate normally allows a central controller of the brain to respond to changes in oxygen density rapidly and therefore promptly resist the particle flux. Particle flux resistance may be also affected by exogenous factors (such as medications). In an example, an ACE inhibitor which improves left ventricular function may increase the resistance to the particle flux of arterial oxygen in the example descried above but decrease the resistance to positive K+ particle flux in venous blood.

A perturbation of particle density is generally caused by a force change which is associated with energy and work. According to some embodiments, a relative indication of the energy or work associated with a perturbation may be calculated. The density change is a direct function of the cumulative mass of the particles which are moved by the force (or the mass of other molecules such as water, which are moved into or out of the compartment to dilute or concentrate the particles). For the purpose of relative measurement, the density change may be substituted for the particle mass moved so that the amplitude of the particle density change may be substituted for the magnitude of the particle mass which moved across the resistor during the perturbation. The aggregate momentum of the density change (for a given perturbation or group of perturbations) may then be calculated as the product of the change in density (surrogate for the mass which moved) and the rate of density change (the velocity of movement of the mass).

Since the particle flux resistor actually comprises a system resistance to particle mass movement and is not generally calculated or known, the momentum associated with any perturbation is relative. A decline in resistance will increase the perturbation for the same force (and increase the apparent momentum as calculated above) but since both a decline in resistance and increase in a force are simply components of the same density change vector, the model of aggregate particle momentum for the purpose of medical diagnosis remains valid. In other words, since disease, such as infection, may lower the resistance to particle mass movement and/or may apply a force to induce particle mass movement, these relative effects are not readily separated and are therefore combined to generate the value of the "functional momentum" of a perturbation or recovery. Human life, and the integrity of the human system, is functions of the particle density and, as noted, this is substituted for the mass in the above equation for this model. Furthermore for the purposes of processor 200 based assessment various measurements such as milliequivalents (meq) may be substituted for the mass in the calculation of density.

As it relates to the state of life and health of a human system, the absolute values of a particle density or the absolute values of a particle density change of different particle types are not mathematically comparable either from a severity or probabilistic perspective. For example, a density rise of 7 meq/100 cc of bicarbonate in venous compartment (which would, in most cases not generally cause distress) does not comprise the same severity as a density rise in density of 7 meq/100 cc of potassium (which would generally be fatal). In many cases a severe a deviation above a threshold of one particle density may comprise a much less severe event than a mild deviation of another particle. To adjust for this disparity provide and image which is indicative of global perturbation severity and recovery, one embodiment comprises a processor 200 programmed to convert the absolute particle value types of; densities, density changes, density perturbations, and density recoveries, density rates of change, and/or density momentums, to "human numbers" called R which are more indicative of the human relevance of those values and which are comparable across a wide range of particles and value types. The conversion generates a "Human Life Relevance scale" (an "R scale") for the densities, density perturbations, density recoveries, and density velocity (rate of change), and density momentum (the product of the rate of change and the duration of the perturbation or recovery) thereby providing a comparable mathematic quantifications of these values in relation to the stability of human life.

In one embodiment, the processor 200 applies a process of conversion of particle density values to the human life relevance scale which may, for example, comprise the application of direct conversion formulae but generally a conversion table for each particle and value type is preferred because these relationships of these values to human life are not linear or readily defined by formulae. Using the conversion method, the processor 200 converts the absolute value into density relevance values DR which are unit less numbers. These conversions are processed in relation to a central point which comprises the normal range for the individual human which can, for example be designated by as 0 DR. A similar approach may be applied to convert perturbations, forces, recoveries, binaries, and images to respective R scales.

In one embodiment the density value range above the phenotypic range are converted by the processor 200 to a range of values from a first DR to a second DR (such as 1 DR and 15 DR). The particle density range below the phenotypic range may also be normalized from a first DR to a second DR (such as −1 DR and −15 DR). The value 0 may be specified for all densities in the phenotypic range, or may be set to the median or average value of the phenotypic density for the individual or the normal range for the individual human may, for example be designated as noted above by a range of 0-0.9 DR. If the phenotypic range is unknown 0 may be set to the median or average value of the population range until a phenotypic range may be established.

These conversions may be designated by the processor 200 with the particle, the compartment, and the DR (such as potassium, venous, −12 DR which indicates a dangerously low venous potassium). The term low may be added (−12 DR low) to assure the position of the potassium is instantly recognized by the researchers and programmers (as these designation are not for use by the healthcare workers, who, being trained with absolute density values, may become confused by the conversion).

As with the conversion of density changes discussed above, one purpose of the conversion is to allow comparison of severity of density values across different particle types. In one embodiment the conversion curves derived from the absolute values are configured with a hysteresis so that the values become more rapidly closer to 15 or −15 as the extremes of the potential range of the values are approached.

An example of a heuristically derived DR for venous $H_2CO_3$ when sepsis, diabetic ketoacidosis, methyl alcohol intake, or lactic acidosis pattern or image primers (which may for example include an elevated anion gap) are present comprises:

Venous $H_2CO_3$ (in meq) (on left)—converted to DR (on right) <16-15, 16-15, 17-15, 18-14, 19-13, 20-12, 21-10, 22-8, 23-4, 24-2, 25-1, 26-0, 27-0, 28-0, 29-0, 30-1, 31-2, 32-3, 33-4, 34-5, 36-6, 37-7, 38-8, 39-9, 40-10, 41-11, 42-12, 43-13, 44-14, 44-15, >44-15

In this conversion the elevated DR even in the low "normal range" and the rapid elevation of DR for each incremental $H_2CO_3$ value below 26 reflects the acuity of danger these densities may reflect. Since acidosis reflects often reflects a more dangerous dynamic in sepsis then in diabetic ketoacidosis higher DR may be selected for sepsis then for diabetic ketoacidosis. When two venous $H_2CO_3$ data values are available an actual perturbation will be detectable and this can be converted to PR using a perturbation conversion set. A second conversion below of $H_2CO_3$ (on left) to DR (on right) provides gradation of severity only in the direction of progression of sepsis. In this this example high normal and high Venous $H_2CO_3$ are given no severity weight.

<16-15, 16-15, 17-15, 18-14, 19-13, 20-12, 21-10, 22-8, 23-3, 24-1, >25-0,

If preferred the phenotypic range or the population normal value may be converted to DR from −0.9 and 0.9 so that density changes within this range may be tracked. The conversion curve for DR between −0.9 and 0.9 may also be configured with a hysteresis so that the DR become more rapidly closer to 0.9 as the extreme of the normal range is approached.

Like the conversion for densities, the conversion to R values also allows, for example, "human life relevant perturbation" (RP-) to be comparable across different types of perturbations. For example, for a potassium rise, the conversion to RP may be formulaic or a direct conversion of for example 0.2 milliequivalent of potassium rise for each RP between 1 and 15. Alternatively the RP- may be a combination of the density change and the absolute peak or nadir value reached. For example, a rise of 2 meq. of potassium to a peak of 5 meq. may generate a lower RP- then a potassium rise of 2 meq. to a peak of 7 meq. Each density rise may be combined with the peak produced by that change to generate a RP between 1 and 15 and this may be performed heuristically and then modified over time to enhance performance as it becomes evident that different RP are preferred. The use of the peak value in combination with the density change is consistent with the flux resistor model as applied in one embodiment as described above as the resistance to a density change is reasonably assumed to be higher as the peak of the change vector encroaches into extreme and/or dangerous density levels. The human system may have secondary layer of protective resistance near extremes so that resistance may suddenly increase when density levels rise or fall to values near the extremes. According to one aspect of some embodiments, the conversion curve for particle densities and peak or nadir values which fall within a specific range compatible with life, may demonstrate a prominent hysteresis near extremes.

In addition to the lack of direct comparability of absolute density changes between particles, one perturbation or abnormal value of a particle density caused by one force, may be much less severe, as it relates to immediate risk, than an identical density perturbation of the same particle density caused by another force. This may not be accounted for by a conversion severity scale unless the scale is adjusted for different perturbation forces or clinical conditions which inducing the density. In an example a H2CO3 of 22 which has fallen due to volume expansion is considered representative of mild severity whereas the same H2CO3 due to sepsis is considered representative of high severity. A universal conversion scale to a human severity value will not solve this problem of diversity of severity. The PHM may be programmed to have to apply different severity scales or otherwise adjust the severity of the particle density based on the image (for example a sepsis image) of which it is a component or based on a detected force which may be inducing induced the particle density. This is referred to herein as conditional severity adjustment. Alternatively or in combination the severity of the H2CO3 is not adjusted in this manner by the processor 200 upon detection of the image or force, but rather the force binary itself is designated with the high severity, that is the force binary comprises the conditional severity adjustment as a function of its components. This may be achieved by applying different severity scales to different force binaries even though the severity of the theta of the binary is not adjusted. This may prevent confusion by many healthcare workers who may find it difficult to mentally accept different severity indications for the same density value of the same particle.

One embodiment estimates a density velocity associated with the aggregate movement of particle mass associated with a single perturbation or recovery or a combination of a perturbation and recovery. The output of the density velocity as defined by the slope of density change may be converted to adjust the R scale from, for example 1-15 velocity R (VR), so that the severity of momentum is reasonably comparable across particle types. One embodiment estimates a density momentum associated with the aggregate movement of particle mass associated with a single perturbation or a recovery or a combination of a perturbation and recovery. The output of the momentum estimation may be converted to adjust the R scale from, for example 1-15 "momentum R" (MR), so that the severity of momentum is reasonably comparable across particle types. Other converted severity values such as perturbation force may also be calculated if multiple measurements are made allowing the detection of acceleration. It may be preferable to use the various R only as tools to generate images and not to output or quote R to clinical staff as clinicians may confuse these normalized severity measurements with actual density values. The displayed numeric outputs in the organelles are preferably the absolute values of density or density change, whereas the color, size, shape, movement, or position, of a given organelle may be a function of one or more R or other indicator of severity such as relational indicators.

With this approach density changes may be defined as a function of the R. In one embodiment changes in density toward normal are considered recovery changes or recovery vectors. These may be quantified as recoveries and designated with the direction, momentum, and duration of the vector. For example a low venous potassium density of 2 meq/100 cc may be designated with a conversion to 12 DR (as it is a life threatening low density) whereas a potassium value of 4 meq/100 cc may be converted to 0 DR as this value is likely to be phenotypically normal. If the potassium moved from 2 meq/100 cc to 4 meq/100 cc in 24 hours, the converted perturbation severity may be calculated as 0 PRP as the movement from 12 DR to 0 DR is not considered a perturbation but is rather considered a recovery. In this example the recovery change will be designated as 12 Recovery R (RR) reflecting excellent recovery from a severely perturbed density value.

One example of DR and PR designated heuristically. In this example, if the potassium was 2 meq/100 cc and then measured 24 hours changed to 5 meq/100 cc this may, for example, generate a first venous potassium DR of −12 and a second venous potassium DR of +4. However, the movement of such a large mass of venous potassium into the venous compartment may pose a risk if the force causing the movement remains operative. However movement toward normal carries less risk than movement away from normal so this may be weighted (for example by multiplying a recovery movement by 0.5 or another value as reflected for example in a weighting table). Therefore, the conversion for the above rise event from 2 meq to 5 meq to R would comprise three vectors, two sequential positive R vectors, the recovery R vector and the perturbation (overshoot) R vector, and the vector sum of the two R vectors, all three of these may be described by R values with the third representing a vector sum, the vector sum representing the total movement of particle mass during the sum of the duration of the two vectors. For some particles, anytime the total change is high there is reason for concern whereas with others, such as invasive particles, a fall may only be favorable so that for this particle the weighting of the severity of a change may be different for different particles, for example with invasive particles change, the absolute value of any fall in particle density may always be designated by RR.

The connections and interrelationships of the forces and the particle densities which comprise the PHM are extensive and the PHM is temporally and spatially interdependent. For this reason, a local primary distortion of the PHM often induces secondary distortions of the PHM. These secondary distortions comprise dynamic changes of other particle densities and/or other forces which comprise the PHM. This secondary distortion may be self-limiting and may be reversed by secondary recovery forces or this secondary distortion may induce a tertiary distortion or a force cascade of PHM distortions which may spread across the PHM and overwhelm even cascading density stabilizing and recovery forces until these forces are no longer sufficient to return the PHM to a state where sustained life is possible. The PHM now is in a state of terminal distortion. Terminal distortions are generally initially highly complex and may further increase in complexity despite the inability of the matrix or healthcare workers acting on the matrix to return the matrix to a state which will remain living very near death and after death the matrix may exhibit a progressive more entropic pattern over time as life forces progressively diminish to the no life force state. The entropic progression may be more rapid in specific compartments of highly complex function and high dependence on high instantaneous oxygen density, such as the brain, whereas it may be less rapid in compartments with less complex function and less dependency on instantaneous oxygen density.

According to some embodiments, the presence of a density modifying force in the PHM is identified by identifying a density perturbation of at least one biologic particle in at least one PHM compartment. The density perturbation (and the related severity of the perturbation) may comprise, but is not limited to, at least one of a magnitude, a slope, an acceleration, a pattern, a polarity, a percent change, a frequency, an amplitude, and relational combinations of the preceding variations of the same or with other particle densities. Density perturbations commonly occur as a rise (increasing biologic particle density) or a fall (decreasing biologic particle density) or in the alternative a perturbation may comprise a deviation form a normal (phenotypic) pattern of a particles density over time. However, two instances of increasing density of the same particle, for example, may comprise different types of events which only share the common feature of comprising a rise in the same particle density. Since, in one embodiment, as will be discussed, the processor 200 links perturbation inducing forces with perturbation events, the two instances may not be otherwise related in terms of causality. In an example a fall in platelets with a low slope may be defined by the processor 200 as a different event (rather than a less severe event) from the decrease in platelets with a high slope. In this way perturbations of similar polarity but with different patterns suggestive of different causal forces may be readily linked by the processor 200 to the forces more likely to have inducing them. In one embodiment the linkage is of variable strength and based on probability of the linkage.

The linkage may be scaled between 0 and 15 with 15 representing the highest probability of causal linkage. For example a H2CO3 fall associated with a rising anion gap, and a rising lactate, and a low SVO2 provides a linkage of 15 indicating the pattern of forces is sufficient to render a definitive causal diagnosis that these forces caused the negative perturbation of H2CO3. However, neither a rising anion gap, nor a rising lactate, nor a low SVO2, are apical forces which may begin the process. In one embodiment the processor 200 is programmed to proceed with searching and testing until the apical force is identified.

In one embodiment the PHM processor 200 builds the PHM and its distortions by linking objects to produce basic relational objects which may comprise 2 linked events (binaries), three linked events (trinaries) or four linked events (as coupled binaries or as quaternaries) and builds more complex objects (for example force cascades of events or force cascades of binaries, trinaries or quaternaries) by adding objects. Binaries include but are not limited to: An image binary may be comprised of, a first event or exogenous action (called an ialpha event) and second event or exogenous action which occurs in relation to the ialpha (called an ibeta event).

A perturbation force binary may be comprised of, for example an endogenous force or exogenous action (called a falpha event) which potentially induces a perturbation event (called an fbeta event). This is contrasted with image binaries which are linked due to their relationship in an image or cascade and not necessarily due to a force-density perturbation relationships.

A recovery force binary may be comprised of, for example an endogenous force or exogenous action (called an fsigma event) which potentially induces a recovery event (called an ftau event).

In one embodiment, an fbeta cascade comprises a cascade of perturbations (which is the typical early image of a cascade). An ftau cascade comprises a cascade of recoveries (which is the typical late image of a treated cascade). An fbeta cascade-ftau cascade reciprocation may be comprised of the combination of a perturbation cascade and a recovery cascade. These are the types of incomplete images of distortions which often exist before the polyquaternary which defines the identity of the distortion of the PHM is solved.

One or more variations of falpha may induce or otherwise cause or contribute to the same type or types of variation or a different type or types of variation of the fbeta event. A particle density modification which comprises an fbeta event is often both a threat to the health of the human and also a marker which the processor 200 analyses along with other binaries or image components to generate a distortion comprised of the falphas and fbetas and to identify to the source(s) of that threat.

Within one compartment of the PHM, such as, for example, venous blood, a first particle density induced by a first force may comprise a second force which alters or tends to alter the density of at least one second particle within the same or another compartment. The second density modifying force may be induced by the second particle density directly or indirectly (as, for example, through the action of the particle on an organ or group of cells which induces the density modifying force). The processor 200 continues to links new forces and densities to generate images and cascade of linked forces and perturbations. Alternatively dysfunction or failure of an organ or group of cells, and/or the increased or decreased intake or output of a given particle, may comprise a first density modifying force without an intermediate particle.

A first perturbation of particle density responsive to a first force may comprise a second density modifying force on at least a second particle density. These events and forces are linked by the processor 200 to generate cascades of particle density perturbations and the companion cascades of particle density modifying forces which induce the perturbation cascades. These generate apical or primary, secondary, tertiary and cascading distortions of the PHM and of the motion images responsive to or representative of the dynamic distortion.

In one embodiment, a density modifying force is defined as a recovery if the direction if the force vector is toward a normal range and as a perturbation of the direction of the vector is away from a normal range. The density modifying force is further defined as positive (and/or the perturbation or recovery is defined as positive), if the particle density perturbation or recovery responsive to the force comprises a rise in density of the perturbed particle. The density modifying force is defined as negative (and/or the perturbation or recovery is defined as negative), if the particle density perturbation or recovery comprises a fall in density of the perturbed particle. The density modifying force may be a direct force or may be mediated by one or more controlling sensors responding to the perturbation, and/or one or more other particle densities or perturbations.

In an example, an alpha (a perturbation force) comprising a rise in the density of the molecular particle, H2CO3 in venous blood away from the normal range, may induce an theta (perturbation event) comprising a rise in the density of the gaseous particle CO2 in arterial blood. In another example, an alpha comprised of arise in the density of the particle cortisol (as defined by the administration of the drug or a measured drug level) may further comprise a positive falpha in relation to particles glucose, insulin, and neutrophil and a negative falpha in relation to particles lymphocyte and eosinophil. In a further example an falpha comprised of the infusion or at least a minimal density of the particle heparin may further comprise a negative falpha on the particle platelets in the presence of an falpha comprised of a minimum density of a companion falpha particle, antiplatelet factor 4.

The processor 200 is programmed to manage exceptions to this approach. For example, during a sepsis cascade, a rise in the density of neutrophils may peak and then the neutrophils may fall back toward, into and then below all of the normal ranges. In one embodiment, this is identified and designated as a bipolar perturbation which is a subclass of a perturbation wherein the positive perturbation force is later replaced by a negative perturbation force (in the case of neutrophil case comprising relative failure of bone marrow production or release) and is divided into two sequential force binaries, a first perturbation binary and a second negative perturbation binary which is corrected by a positive recovery.

The processor 200 may be programmed to consider a plurality of factors in discriminating a bipolar force perturbation from a force quaternary. For example, if the processor 200 detects at least one of, parallel perturbations or the slopes of parallel perturbations which have not become less severe, the interval after treatment to the onset of the reversal in polarity is insufficient to expect recovery, or a new perturbations suggestive of increasing severity has developed adjacent in time to the reversal, then the processor 200 designates the perturbation as a bimodal perturbation and identifies the second portion of the bimodal perturbation as a second force perturbation having the same force as the first force perturbation. In the above example if the processor 200 detects a rise in neutrophils followed by a fall, the processor 200 looks for the forces which induced the rise and the force which induced the fall. The processor 200 also evaluates the parallel perturbations or the lack thereof. If, for example, if the processor 200 detects that a negative perturbation of H2CO3, a negative perturbation of platelets, and/or a positive perturbation of heart rate continue without reversal of slope or improvement then the processor 200 may identify the neutrophil pattern as a potential bimodal perturbation of neutrophils and then may designate the rise in neutrophils as a first perturbation and the fall in neutrophils as a second perturbation not a recovery. These two sequential perturbations will have the same falpha (in this case sepsis). However, the processor 200 may seek to identify another other force or other forces (other than sepsis) along the PHM which may have triggered a fall in neutrophils (such as chemotherapy).

For particle densities which may potentially exhibit a bipolar pattern, for example in response to a common a single force, the designation of a recovery (ftau) by the processor 200, will occur if an antecedent theta (which is at least partially reversed by the ftau) has been detected and no competing perturbation, force which would explain the reversal and solve the change as a new force perturbation is identified. If no theta has been detected a change in such a particle is designated as a perturbation.

A recovery may overshoot and this will comprise an overshoot perturbation and will be detected by the processor 200 as a continuation of the recovery vector until it turns into a perturbation as it passes the normal range. A recovery force comprises the perturbation force of the overshoot perturbation. One example which may produce a positive perturbation overshoot is a neutrophil recovery in the above example.

The particle density which induces a perturbation force may be external to the compartment wherein the perturbation of particle density occurs. A positive or negative perturbation force, or a high or low value of particle density, in relation to the patient's phenotypic range (or the relevant population's normal range of a the particle density) indicates that one or more forces, which may induce that range of positive or negative perturbations, has likely occurred.

In one embodiment the processor 200 is programmed to detect a perturbation in density of one particle along the matrix and then to determine at least one value indicative of the perturbation or one or more features or measurements of the perturbation (for example a change in density value, density slope, etc.). The processor 200 is programmed to order, detect, and/or quantify the density of other particles and/or to detect a perturbation force or recovery force which would be expected to induce the perturbation or recovery the at least one value indicative of the perturbation or recovery. In one embodiment the processor 200 builds a time matrix of particle densities, actions, and dysfunctions, objectifies the time matrix, and then identifies the occurrence of objects comprising potential perturbation forces by identifying the occurrence of positive or negative density perturbations or of high or low density values, and then identifies and/or outputs the potential perturbation forces as well as the projected forces on other particle densities as well as the matrix or an image representative of the matrix.

In an example, if a positive density perturbation and/or high density value of the particle K+ is identified in the venous blood compartment of the PHM, then this indicates that a perturbation force has occurred because the K+ particle density or at least one feature of the perturbation is outside the range or otherwise is varying in a manner, which would, without the presence of this perturbation force have been prevented by the density normalizing force that particle. The recognition by the processor 200 that a density modifying force either has occurred, or is occurring, triggers a search for the perturbation force which could cause the detected density value or density perturbation. This force may, for example, be one or more of: an action causing an increase in intake of K+, an increase in intake of K+ itself, another particle density which causes a positive change of K+ such as a beta agonist particle or aldosterone antagonist particle, or an organ dysfunction such as renal dysfunction (which may, for example, also induce a perturbation force on the particle creatinine so that venous creatinine density may be used as a marker for the force (for example, a positive perturbation force comprising an increase in the venous density of creatinine may then comprise the falpha for an beta event comprising high or increasing venous K+ density). The perturbation force binary would comprise a linked increase in creatinine density and an increase in K+ density. The processor 200 would then search for other potential falphas such as the intake of aldosterone antagonists and/or an angiotensin converting enzyme inhibitor, and/or the intake of KCL or other molecules containing K+. The processor 200 will then search for the one or more fsigmas, (the recovery force(s) which will induce the recovery of the perturbed K+ density), such as, for example the discontinuation of the angiotensin converting enzyme inhibitor. If no suitable fsigma is detected, the processor 200 may be programmed with protocolized order for at least one fsigma and then to detect the occurrence of the fsigma which was ordered, and to order additional diagnostic testing to assure the expected or desired ftau (recovery of the venous K+ density occurs) within the specified time interval.

In addition to the sequence above the increase in venous creatinine density represents both an ialpha and a falpha. In one embodiment five or more ranges or relational ranges of density values are stored for a particle density (such as creatinine) for any given compartment; a first population range as defined by the relevant general population, a second phenotypic range, a third personal baseline range as defined by the patient's baseline values around which is the phenotypic range, a forth risk range, as defined by that particle density related risk values (if any) in relation to the PHM, which may include the medications received, the images and or cascades generated by the patient, or the patient's known conditions, and a fifth range as defined by a range of preference or for some specific purpose by the healthcare worker(s) managing the patient.

In the instance of creatinine, a positive perturbation of venous creatinine density outside the patient's phenotypic range comprises an theta for which the processor 200 will search for the falpha which could have induced that perturbation in relation to the PHM. The falpha (perturbation force) may comprise a medication, an inflammatory cascade, sepsis cascade, a fall in fluid intake, a fall in cardiac output, to name a few. If a suitable falpha is not identified or if a detected fsigma (recovery force) fails to reverse the falpha, when reversal would be expected if the falpha was the only force active in relation to creatinine, then a range of testing for falphas may be ordered by the processor 200 as protocolized. In addition, this theta of creatinine comprises a positive sentinel falpha for many other positive particle density perturbations of, such as medications cleared by the kidney. Furthermore, this theta of creatinine comprises a negative sentinel falpha for negative particle density perturbations such as H2CO3.

The processor 200 may be programmed to search for, analyze, and link each potential theta and to order tests for particle densities which, given other distortions along the PHM, may be affected and to reduce particle densities (such as drug dosages) which are likely to be affected. In one embodiment, a perturbation of a single particle density (such as a positive perturbation of venous creatinine density or a negative perturbation of venous platelet density) may trigger a range of object linkages extending from the falpha objects generated by processor 200 which characterize the positive perturbations. These objects may then be linked to the theta. The theta will be linked to the fsigma, which will be linked to the ftau. The combinations of these many linked objects generate an image and physiologic characterization of the global impact on the PHM and in particular on the dynamic patterns and values of densities of a wide range of particles in the venous compartment that an falpha may be inducing (or signaling in the instance of a sentinel falpha).

Perturbation force binaries may be identified as having a solution if one or more falphas, which would be expected to induce the perturbation values or range, has been identified. Perturbation force binaries are identified as having no solution if no falphas have been detected which would be expected to induce the perturbation values or the range which has been detected. Binaries with no solution, comprise for example; perturbations and or high or low density values, without the expected forces or relational events, perturbation forces without the expected perturbation, recovery forces without the expected recoveries, and recoveries without the expected recovery forces. A time matrix or other rendering of binaries which have a solution may be generated and displayed in combination with or separate from the time matrix or other rendering of binaries without a solution. In one embodiment, a PHM may be comprised of binaries with and without solutions which may be differently designated or displayed.

In an example, a positive perturbation of venous density (or a high venous density value) of neutrophils may be induced by a range of forces. As noted, the presence of a minimum density of corticosteroid particles comprises one potential falpha inducing a positive perturbation of neutrophil density. However, the increase in density of neutrophils induced by corticosteroids is generally modest and corticosteroids would not be expected to induce marked increase in density of band particles. Therefore, a perturbation indicated by a modest increase in the density of neutrophils (a first theta event) would have one solution identified if corticosteroid administration is identified as an falpha event by the processor 200. However, if a positive perturbation in temperature (a second theta event) and a positive density perturbation theta in band particles 9a third theta event) is identified, the forces inducing these two fbetas cannot be solved by a corticosteroid falpha. Furthermore, since the three fbetas are all potentially relational (relate to a common falpha), the corticosteroids are designated by the processor 200 as an unsolved perturbation force binary for the relational binary wherein the theta is a complex object comprised of a combination of the three related fbetas. In one embodiment, the processor 200 is programmed to output the presence of two perturbation force binaries with no solution and a third perturbation force binary with a solution. The processor 200 may then output a visual indication of all three thetas and variations of the relational pattern of all three thetas (as derived from the increase in venous neutrophil density, increase in temperature, and increase in density of band particles) along with the designation that the falpha for these thetas and particularly for the combination of these thetas (when grouped as a single theta object) has not been identified.

In one embodiment all elements that have a potential to form any binaries—exogenous events, occurrences, patterns, and forces to name a few—are continuously monitored (e.g. searched for) such that the absence of an element, after a sufficient processing delay or cycle indication, may be recognized as a failure of identification for a given time span, and therefore may indicate a binary without a solution.

Overlapping dynamic visualizations such as weather maps responsive to binaries with solutions and without solutions may be generated. In one embodiment annotations or other indications are provided which may indicate that a patient storm cell or group of patient storm cells does not have a solution and the falpha (and particularly the apical falpha) inducing the storm cells is unknown.

In one embodiment, the processor 200 is programmed to display which binaries have complete solutions and which do not. Overlapping weather maps responsive to binaries with solutions and binaries without solution may be generated. In one embodiment annotations or other indications are provided which indicate that a patient storm cell or group of patient storm cells does not have a solution (and the forces or inducing the patient storm cell is not yet known).

The unsolved falphas and fsigmas may be mapped on a time matrix in relation to the position of associated positive and/or negative density perturbations (and/or high or low density values) and recoveries which indicated the presence of the undetected forces. A large or expanding matrix of many binaries with no solution may be indicative of diagnostic delay (for example, caused by inadequate protocol, a breakdown in protocol, inaccurate diagnoses to name a few). The processor 200 may be programmed to quantify the number of individual and relational binaries which do not have a solution and to provide an output indicative of unsolved forces per unit time.

Early in the presentation of the patient, there may be many binaries without a solution. As time progresses, the number should progressively reduce. A graphical representation of the number of unsolved binaries may be presented to QA personnel and protocol violations may be indicated. At discharge, binaries without a solution which remain may be outputted by the processor 200 along with orders or recommendations for solving the binaries if warranted. The identification and quantification of density perturbation forces according to some embodiments provides more sensitivity to residual and dynamic diagnostic deficiency then the conventional identification of abnormal laboratory or vitals values at discharge.

In one embodiment the processor 200 is programmed to differentiate in the display image binaries (which represent image components) from force binaries (which, in addition to representing image components may also be defined by the density modifying force exerted by the falpha on the theta or by the fsigma on the ftau). The display of the force binaries as overlays, or in-combination with the image binaries may be provided. The forces or the force binaries may be presented as a semi-transparent overlay.

The physician may have the option, as by right clicking on the displayed density modifying force or force binary of the PHM or on the display such as a weather pattern produced by the density modifying force or force binary, to identify or select the falpha and particularly the apical falpha likely inducing weather patterns or to select an action, such as testing, to identify the falpha. At the time of patient discharge a relational timed display and/or listing of the residual binaries without a solution may be provided. The physician may then select the falphas likely inducing the perturbations detected by the processor 200. Since, with more data and time, the processor 200 may identify the falphas and thereby find the solution for these binaries, additional information and further processing after discharge may disclose whether or not the physician's designations were correct. The processor 200 may be programmed to provide a context sensitive group of testing choices (as from a drop down menu) known to potentially identify one or more falphas which could have induced the detected theta.

The processor 200 may be programmed to automatically order future testing to determine the future of the falpha, or may be programmed to provide an option for the physician to instruct the processor 200 to ignore one or more of the forces. In one example, when there is sufficient time, without undue risk of diagnostic delay, to perform tests in sequence, the processor 200 may process a risk cost based analysis to determine the next tests to be performed. For example the processor 200 may rate the probability that the test will identify the falpha, rate the potential risk of the test, rate the risk of failure to perform the test, and rate the cost of the test. The processor 200 may be programmed to rate the risk of the test from 1 to 5 with 1 being the lowest risk, the risk of failure to rapidly diagnose rated from negative 1-negative 5 with the lowest risk being negative 1, the probability that the test will identify the falpha may be rated from 1-5 with the highest probability being 1, and the cost of the test from 1-5 with the highest cost being 1. The risk of the test or the risk of failure to rapidly diagnose may be weighted to provide 2-3 times its value. Alternatively another factor may be weighted. The test selected to order first may be the one with the lowest sum. (Alternatively non-invasive and minimal or non-irradiating tests may be prioritized and quantified separately from invasive tests because to place the do-no-harm doctrine as a prime objective.)

In an example a negative perturbation of venous platelet density is identified by the processor 200 along the PHM as a 10% decline in platelets over 24 hours with a fall slope of ⅚ per hour and an absolute fall of 20 from 200 to 180. The processor 200 searches for an falpha, for example, prior infusion of heparin, inflammatory augmentation, recent transfusion, recent treatment with clopidogrel, positive antinuclear antibody, to name a few and searches for other potential falpha or sentinel falpha along the PHM (which may include for example prior infusion of heparin and/or an evolving sepsis cascade). If the processor 200 identifies heparin infusion within the appropriate time, the processor 200 may be programmed to proceed with testing as a function of a threshold or a derivative of the combinations of the numbers or based on a pattern of the time series of the sum or a derivative of the combination of the numbers. For example the processor 200 may be programmed to proceed with ordering a test if the sum is less than 5. Platelet factor 4 is an expensive test which may be rated a 4 in terms of cost, but it is a simple blood test it has a low risk which may be rated as 1 in terms of risk. However, the risk of failure to diagnosis heparin induced thrombocytopenia is high but, if present, it is still very early so this may be rated as only negative 3 and finally the probability the test will be positive is low given the marginal decrease in platelets and brief decline so this may be rated as 5. The sum is 7, which is above the threshold so the processor 200 will not order the test unless overridden. The processor 200 may be programmed to calculate the time, as projected by the slope, wherein the sum would be 5 if the slope of the decline continued and to repeat the platelet count at that time and make another programmed decision about which tests to order (if any). These ratings may be heuristically derived by expert panels and then readjusted as determined by assessment of cost and performance associated with the ratings.

Even seemingly minor density modifying forces may be deadly because they may irreversibly distort the PHM. This is especially true if the forces continue unabated or progressively increase (as may be the case when a self-replicating microbe has invaded the human, distorting the PHM). Often only a few organisms initially invade the PHM and produce minimal distortion of the PHM. Distortion of the defense (immune) system of the PHM often comprise the first fbetas and falphas which are readily detectable when the numbers of organism which have invaded the PHM is still too low for detection even by blood polymerase chain reaction testing.

Here it is the dynamic distortion of the PHM, and not any single or relational density value, which best characterizes the state and cause of invasion. As the organisms increase in numbers, the PHM distortion they induce in the immune system increases and the invasive proteins generated by the organism may induce PHM distortion, for example in the clotting system. Each distortion in this comprehensively connected PHM pulls or pushes on another portion of the PHM dynamically distorting that portion. Each time a distortion occurs in the PHM, dynamic compensatory perturbation forces may be triggered to protect the PHM. In addition dynamic recovery forces may also be triggered to move the PHM into a more life favorable matrix configuration which may not be the original configuration of the PHM. Compensating forces, while responsive to perturbations are different from recoveries in that they will not mitigate the falpha but are rather temporizing and often simply mitigate the fbeta producing a false sense of recovery. In one embodiment, compensating forces and compensating events comprise companion falpha and fbeta to the perturbation being compensated. The severity vector of the compensation fbeta may be combined by the processor 200 with the severity vector of the primary perturbation fbeta to reveal the actual severity induced by the combined perturbation and compensating perturbation.

Upon detection of early distortion of the PHM, the risk of excessive or irreversible distortion of the PHM posed by one or more perturbation forces (such as that induced by invasive bacteria) may be reduced by empiric treatment in programmed response to one or more fbetas and/or falphas or larger pattern along the PHM. In one embodiment, perturbation force binaries have four basic states presented in order of increasing risk; solved and falpha and/or fbeta treated, unsolved but potential falpha and/or fbeta empirically treated (as by processor ordered and processor confirmed treatment), unsolved and potential falpha and/or fbeta untreated, solved but falpha and/or fbeta untreated. The last two risk categories may pose an equivalent risk.

The processor 200 may be programmed to detect a new increase in binaries without a solution and identify as by display when an increase and/or a cascading matrix of such binaries occurs and to indicate the presence of the development of a new undiagnosed condition or complication and to suggest or automatically order testing in search of the missing binary components which may provide the solutions for the binaries. Binaries or cascades of such binaries without a solution may be severity indexed based on the potential risk associated with the binaries and the index outputted.

In an example, a negative perturbation of the density of venous H2CO3 in combination with a preceding positive density perturbation of venous bands, a subsequent negative perturbation of the density of venous platelets, may be displayed on the PHM as either as a grouping of perturbation image binaries, perturbation force binaries, or both. This grouping of binaries, if unsolved and not empirically treated, has a high severity risk indicating that a rapid solution comprising determination of the falphas (one of which may be sepsis) is mandated. With these binaries and the cascade distorting the PHM, the risk of failure to rapidly diagnose is high, for this reason the processor 200 is programmed so many tests will be immediately ordered by the processor 200.

Domain of Sets of Biologic Particle Densities of Living Human Beings

A formal domain exits which comprises measurements of compartmentalized biologic particle densities in human beings. This is a primary domain in the field of medical diagnostics. However, data sets of this domain generally lack formal objective mathematical solutions so that large sets of data (such as those in the cloud or on hospital servers), existing with little or no mathematical solution, is a normal final state of data for this domain. For a typical data set in this domain, the lack of a mathematical solution is supplemented by subjective solutions to render highly variable diagnostic results. This renders a domain wherein: a perpetual state of even a large data set with little or no mathematical solution is typical; simple data points existing as "numbers on a page" are acceptable final data formats; and incomplete data sets commonly exist without being so identified.

This explains the crisis which exits in this domain. There is a need to define a formal mathematical solution for data sets in this domain.

Axioms of the Domain of Sets of Biologic Particle Densities of Living Human Beings Given a biologic particle density set D of a living human there exists a force set F, whose members induced exactly those members of D.

Given a biologic particle density set D there exists a probabilistic force set P(F), whose members have a probability >0 of having induced exactly those members of D.

Given a collection of biologic particle density sets there exists a normal set N, whose members are exactly within a phenotypically normal range.

Given a normal set N there exists a normal force set $F_n$, whose members induced exactly those members of N.

Given a normal set N, there exists a probabilistic force set $P(F_n)$, whose members have a probability >0 of having induced exactly those members of N.

Given a collection of biologic particle density sets of a living human there exists a perturbed set P, whose members are not the same as the members of set N.

Given a perturbation set P there exists a variation force set $F_v$, whose members induced exactly those members of P.

Given a perturbation set P there exists a probabilistic variation force set $P(F_v)$, whose members have a probability >0 of having induced exactly those members of P.

Given a collection of density sets of biologic particle density sets of a living human there exists a recovery set R, whose members are not the same as the either the members of set N or the members of set P.

Given a recovery set R there exists a recovery force set $F_r$, whose members induced exactly those members of R.

Given a recovery set R, there exists a probabilistic recovery force set $P(F_r)$, whose members have a probability >0 of having induced exactly those members of R.

According to one embodiment, this set of axioms, analysis may proceed with standard mathematical methods of reduction, inference, simplification and synthesis to engage the science of human medical diagnosis through application to the parallel human time matrix.

In an embodiment, a display is provided indicative of a PHM comprised of solved perturbation image binaries; recovery image binaries, perturbation force binaries, and recovery force binaries, as well as unsolved binaries. Compensating image or force perturbation binaries, which may comprise a sub class of perturbation binaries, may also be uniquely designated in the display so that the severity of compensatory perturbation force and/or compensatory perturbation may be readily visualized. Since in response to severe r progressive perturbations, compensation is often limited in severity and time the processor 200 may show a display indicative of the severity of compensatory perturbation in relation to its projected limits. Binaries and/or the graphical representations derived from them (such as weather map type images) may have a different colors, or other markings to differentiate different binaries and between solved and unsolved binaries or the storm cells associated with different binaries.

While the ialpha of an image binary is not generally a medical condition (although it may be), at least one falpha of a force binary is often a medical diagnosis. A plurality of force binaries may be generated with the same falpha or the same theta. For example, one perturbation force binary may have a theta comprising an increased density of lactate in the venous compartment and/or metabolic region of the PHM and its falpha comprising the diagnosis of sepsis, while a second perturbation force binary may be comprised of the same increased density of lactate but with an falpha comprising a decreased density of central venous oxygen, while a third perturbation force binary may be again comprised of the same increased density of lactate but with an falpha comprising a decreased cardiac output. The decreased cardiac output may also be the falpha for the theta comprising the aforementioned decrease in density of central venous oxygen. Furthermore a decrease in density of venous H2CO3 may be the theta for the three falpha comprised of; increased density of lactate, the decrease in density of central venous oxygen and the decrease in cardiac output. Finally the low central venous oxygen density may be an theta for the decrease in cardiac output. A low vascular volume may be one falpha for the theta which comprises a decrease in cardiac output and sepsis may be another falpha for that same theta. Finally active sepsis may be an falpha of perturbation force binaries for each of these fbetas. In this way, an embodiment generates cascades of perturbation force binaries comprising falphas (force inducers) and fbetas (for example particle density changes) responsive to the force inducers.

These linked sequences and cascades of binaries define the mechanisms and physiologic basis for the operative pathologic process and source of the primary distortion of the PHM, which for example with sepsis as an apical falpha comprises the common or global falpha for the entire perturbation force cascade. However although sepsis may be designated as an apical falpha, sepsis cannot comprise a completed proximal end of a cascade. The cause of the sepsis (the triggering event, the invasive organism, and the primary and secondary compartments invaded) are all potential proximal falphas for systemic sepsis which need to be solved for the binary which contains sepsis as the theta to have a designated solution by the processor 200.

The processor 200 is programmed to follow the cascade back in time to its origin to detect the apical falpha and also the actions (such as central line insertion or surgery which may have triggered the apical falpha.

In one embodiment a single diagnosis (such as active sepsis) may comprise an apical falpha for each component of a perturbation force binary cascade and a single treatment, such as penicillin infusion may comprise an apical fsigma for each component of the subsequent recovery force cascade. Many other falphas will also be identified for smaller patterns of fbetas or for individual fbetas.

Many diagnoses which comprise active disease have companion events embedded within the PHM, which related to treatment or to another condition or sprigs of early recovery from another condition. In an example, perturbations which would not be expected to be induced by the force of active sepsis (such as a sever fall in density of venous potassium) will not, if detected, be included in the cascade of perturbation force binaries having an falpha of active sepsis and despite the detection of a massive sepsis cascade, the processor 200 will search for another falpha to explain the severe fall in density of venous potassium. The detected falpha may be, for example, the administration of furosemide anther force.

In one embodiment all particle densities are designated as falling into at least a portion of the following categories; particle density in normal population range, particle density in the phenotypic range for the patient, particle density chronically stable and elevated or decreased in relation to phenotypic range, particle density chronically changing and elevated or decreased in relation to phenotypic range, particle density high or low in relation to phenotypic range but stability is unknown, particle density acutely increasing or decreasing. Any of these may be identified by the processor 200 as ibetas or fbetas. In this way the processor 200 tracks all densities and density variations, establishes the phenotypic density range or another range for each patient and determines when the densities have been perturbed and searches for one or more falphas which may have induced that perturbation. The processor 200 may generate outputs for healthcare workers wherein all densities have the above designations and densities which are not stable are flagged and automatically tracked by testing. The timing of testing may be, for example, defined by the rate of change and/or the falpha (if known), or by other healthcare worker or statistically testing defined protocols. The above categorization of betas and testing protocols, according to some embodiments, provides a mechanism to prevent density changes from proceeding without, at least, process based analysis of that density change and healthcare worker notification, if indicated.

In one embodiment, the healthcare worker may choose to visualize at least one time segment of the PHM in a format such as a color radar weather map as derived from solved and/or unsolved perturbation image binaries, recovery image binaries, perturbation force binaries, and/or recovery force. Drill downs requesting the binary information relating to the patient storm cells may reveal the spatial and temporal pattern relationships of both density modifying forces and density changes. Drill downs, as by touching a storm cell, or passing a pointer or mouse over a storm cell requesting the image binary information relating to the patient storm cells may reveal the spatial and temporal pattern relationships of events, patterns and cascades comprising the image of a patient's condition and care.

Perturbation of the phenotypic dynamic relational range and/or a pattern of densities may also comprise an theta or ibeta and a force modifying one or more components of the dynamic relational range or pattern of densities may be a falpha producing a perturbation force binary of the dynamic relational density range or density pattern.

In one embodiment, other events other than values or perturbations of particle densities may be included as fbetas or ibetas of the PHM. For example the frequency or consistency of bowel movements may be entered as by subjective assessment by a nurse or by sensor on the toilet which automatically detects bowel movement frequency and/or consistency. If diarrhea is identified by the nurse or detected by the sensor this becomes the theta and the processor 200 searches for an falpha. If, for example, recent prior or present cephalosporin administration is detected along the PHM this may trigger an order for example Clostridium difficile testing on the stool by polymerase chain reaction. If this testing is positive then both the cephalosporin and the clostridium difficile becomes the falphas for the theta diarrhea. Together they comprise two perturbation force binaries as the cephalosporin will become the falpha for the theta comprising a minimum particle density of clostridium difficile in the large bowel compartment. The PHM processor 200 may be programmed to check the PHM for allergies and order treatment if protocolized to do so, which may include discontinuation of the cephalosporin or substitution with another antibiotic if the PHM suggests incompletely treated infection requiring continued antibiotics. The perturbation force binary now has a solution and both the theta and falpha of the binary are under treatment. The processor 200 will then search for recovery of the fbetas (for example recovery of the diarrhea, and a fall of in Clostridium difficile in the stool).

If despite the fsigma, which may comprise the administration of vancomycin, discontinuation of the cephalosporin and/or other recovery inducing force, the ftau is not detected (recovery does not occur within the expected time) then the recovery force binary is considered unsolved and the perturbation force binary is designated as a perturbation force binary with recovery failure. Processor 200 identification of perturbation force binaries with recovery failure generates an output indicative of recovery failure despite treatment for the healthcare workers.

In another example, an increase in venous density (for example form zero density) of chemotherapy as indicated by chemotherapy infusion may be designated as an falpha. If the chemotherapy is known to be myelosuppressive one expected theta of a perturbation force binary may include a decrease in density of neutrophils over a time period following the chemotherapy. The processor 200 projects the expected range of values and slope of the theta over time as for example determined by population studies. A change in neutrophil density and a slope of the change falling within this range comprises a solved perturbation force binary whereas a neutrophil density change or lack thereof or slope which is out of this range comprises an unsolved or incompletely solved perturbation force binary. The incomplete perturbation force binary then becomes the theta for which the processor 200 may be programmed to detect the falphas by ordering additional or more frequent testing or other diagnostic or therapeutic action, such as blood or fluid polymerase chain reaction testing, blood cultures, and/or the administration of granulocyte growth factors provided the processor identifies no contraindication. In this manner all chemotherapeutic administration events are processed to assure that the perturbation force binaries are promptly solved and recovery detected and assured, if possible.

In another similar example, a surgical procedure may comprise an falpha, which is expected to produce a range of thetas including, for example, a modest increase in venous density of neutrophils and a decrease in venous density of lymphocytes or of one group of lymphocytes such as T helper lymphocytes (as for example determined by population studies for that surgical procedure). The processor 200 projects the expected range of values and slope of the thetas over time as for example determined by population studies. A rise in venous neutrophil and a fall in lymphocyte density and slopes of rise and fall within the expected ranges comprises solved perturbation force binaries whereas a neutrophil density change or lymphocyte change or slopes which is out of this range, comprises an unsolved or incompletely solved perturbation force binary.

Likewise after surgery a segment of the PHM with a change in the density of bands outside the expect range comprises an unsolved or incompletely solved perturbation force binary. The presence of one or more unsolved perturbation force binaries may comprise new falphas which trigger additional or more fbetas and falphas such as testing or other diagnostic or therapeutic action, such as polymerase chain reaction testing, blood cultures, and/or empiric antibiotic therapy. The binary linkages are continued until the recovery force binaries are solved or otherwise resolved along the post-surgical segment of the PHM.

In one embodiment one or more human genes, gene variations, or mutations may comprise the falpha (the force inducer) for a given particle density or relational density change. The identification of a density which is outside or nearly outside the statistical range identified for the relevant population or demonstrating a dynamic particle density response to a force (such as the venous density of a pharmaceutical) which is outside the range which is expected statistically in response to that force may generate a review a comparison with the genetic code of the patient.

In one embodiment the PHM processor 200 is applied to test the relationship of a wide range of human genes to the resting particle densities and/or particle density variations in response to at least one force. Each gene (which may be a mutated gene) may be the equivalent of a fixed step function on the matrix as for example is the genetic sex of the patient. Perturbation force binaries wherein theta are at least one of density values, density variations, relational densities, or cascades of density variations, are combined with each known gene of the patient as the falpha to produce hybrid force binaries containing genetic information. The hybrid force binaries may then be statistically evaluated to determine if specific genes or clustering of genes are associated with one or more specific perturbation force binaries, one or more density modifying forces, or one or more thetas.

In one embodiment when multiple perturbation force binaries are identified with a single theta instance the processor 200 may aggregate the forces to determine whether a possible complete or partial solution has been identified.

In one embodiment, the health care worker may be provided with an environment to explore "what if" scenarios to examine what conditions may adequately solve the perturbation force binaries present. In this way, the health care worker may narrow proposed solutions even before lab results have been returned. For example, a health care worker may believe that a force would solve a binary but not realize that the severity of the theta cannot be adequately explained by the proposed falpha. In this way, simplistic or inadequate explanations which may, without an environment containing the rigor of force aggregation and projection, have been considered possible answers can, through the application of the PHM be quickly ruled out or considered suspect.

In one embodiment, the solution of the force binary is designated as a function which compares properties of the falpha or fsigma to properties of the theta or ftau in, for example, a ratio. For example, the slope of the theta may be defined in relationship to the magnitude of the falpha. In the case in which the falpha is a diagnosis, ranges may be provided for the severity of the diagnosis in a manner discussed previously for forces perturbations and recoveries.

Organ or cellular failure may first induce a density modifying force on a passive (non or minimally force inducing) particle which provides indication of the organ dysfunction or failure and may therefore be designated as a sentinel falpha. Perturbation of the density of a sentinel falpha indicates that a density modifying force is likely being generated (or may be generated in the future) on at least one other particle density.

In one embodiment, the time relationship between the falpha and the theta may include a phase shift based on presentation delay. If the mechanism of acquiring the density values includes a delay, this delay may be included in the time relationship and may even include the possibility that the theta may be identified before the falpha presents to the system.

According to some embodiments, the value of a test, such as a measure of a compartmental density of a biologic particle, as an "enhancer" of the probability that a given clinical condition is present, is a function of the effect the incorporation of the test into the PHM has on the probability of the PHM for that condition at the time of incorporation. In other words, the sensitivity and specificity of a measured biologic particle density for a condition, such as sepsis, is a function of the sensitivity and specificity of the PHM which incorporates the particle density measure, minus the sensitivity and specificity of the PHM when the has not been so incorporated. Using the PHM, the value of a diagnostic test is defined by its ability to more completely fill in the missing components of the dynamic PHM image so that the image is more sensitive and/or specific for a clinical condition than was the original image which did not incorporate the test.

In one embodiment the PHM includes a probability matrix as one of its components which may be integrated with the other components of the PHM. The probability matrix comprises a matrix of time series wherein each times series is comprised of the timed probabilities of a condition (for example sepsis) as defined by the PHM (including the other probability time series).

The time series matrix of probabilities, correlation, and/or probability discriminating measure (such as sensitivity and/or specificity) is preferably objectified and analyzed to define probability perturbations (theta) and to identify the forces (falpha) inducing those perturbations of probability (such as a diagnostic test result, historical or physical finding). For example, the processor 200 identifies a 30% increase in specificity of a time segment PHM for sepsis after a high density of procalcitonin has been added to the PHM, in this case procalcitonin is identified as the force (the falpha) inducing the positive perturbation (the (beta) along the sepsis probability time series of the PHM. A positive polymerase chain reaction test for bacterial DNA in venous blood may be a very strong falpha inducing a positive perturbation in the objectified sepsis probability time-series of the PHM sufficient to alter treatment and testing.

According to one embodiment of a method of some embodiments, clinical trials to determine at least one diagnostic probability or discriminating measure (such as sensitivity and/or specificity) for example, of a new test are performed using the PHM. One method for evaluating the at least one value indicative of the diagnostic discriminating value of a diagnostic test comprises; obtaining medical data, which may include for example, genetic, historical, or test derived data, from a set of patients, generating a PHM for each patient derived from the medical data, determining a first result comprised of the probability or discriminating measure of a condition using a PHM which does not incorporate the result of the diagnostic test, incorporating the result of the diagnostic test into the PHM, determining a second result comprised of the probability or discriminating measure of a condition using the PHM having the diagnostic test incorporated into the PHM, comparing the first result to the second result and calculating a comparison result and defining at least one diagnostic probability or discriminating measure as a function of the comparison result. The comparison result may for example be derived by subtracting the first result for the second result.

After a biologic particle has been sampled its probabilistic value begins to move away from the sample value and defines a probabilistic range of values which may be considered a probabilistic wave function of the particle. The distance between the sampled value and the probabilistic range of values after a given time interval will be affected by the clinical condition of the patient.

One approach for projecting a path of the PHM and particularly the path of a distortion in the PHM and for determine a patient specific frequency of automatically ordered lab testing is to calculate a potential worst case path or value of a parameter and then identify the retesting time based on the minimum change of the parameter which would have clinical relevance given the potential condition or conditions identified by the processor 200. For example, if the processor 200 has identified severe sepsis as a potential condition, then a projected bicarbonate (or other lab values) may be calculated by Equation 1:

$$V_p = V_s + T_D(dV/t) + T_i(dV/t) \qquad Eq(1)$$

Where:
  $V_p$ is the projected value of the parameter at the projected time;
  $T_i$ is the time interval between the last sampling time and the projected time;
  $T_D$ is the delay between the sampling time and the display time;
  $V_s$ is the value of the parameter at the sampling time (this may not be known until later if there is a transport and/or testing delay); and
  $_dV_/t$ is the worst case or near worst case slope of the parameter given the condition(s) identified as potentially present by the processor 200 (such as sepsis).

An efficient timing of retesting which would enhances the ability to early detect change may be made by setting the next sampling time to an interval calculated from specifying the minimum or maximum (depending on the polarity of the trajectory) of the projected value which would (if known) affect diagnostic or therapeutic action given the condition(s) identified as potentially present by the processor 200. For example, suppose the bicarbonate value at the sampling time (Vs) was 20 and is identified by the processor 200 as falling at a rate of 0.5 meq/hour and the processor 200 further identified the image as representing a high probability that sepsis is present, yet the processor 200 identifies the next test for bicarbonate has been ordered by the physician at 8 hours and the average, worst 10 percentile (or other measure), of delay from sampling time to display time (TD) is known or calculated to be 1 hour for this particular hospital ward. Then in one embodiment the processor 200 may be programmed to identify an improved sampling interval based on a projected "near worst case" bicarbonate fall of 1 meq/hour for the condition of sepsis, and adjust the repeat bicarbonate testing to 2 hours since a fall in bicarbonate to 17 (the value which could reasonably be present in 3 hours (sampling interval plus delay interval) would (if known) affect diagnostic or therapeutic action given the condition(s) identified as potentially present by the processor 200 (in this case sepsis). In the alternative, when managing this patient without the processor 200 intervention of some embodiments, the bicarbonate could have fallen to 11 (before outputted as 12 on the display) and this value in this range may result in death (perhaps before the sample is even taken). As demonstrated in this example, the condition or pattern specific projection of individual parameter values provides both warning and a means to improve sampling time and therefore the diagnostic utility of the motion image and improved protocolization of treatment. Furthermore the projection of multiple parameters may be used to render one or more possible paths which the patient storm may take if, for example, intervention in not provided.

The processor 200 may be further programmed to, based on the diagnosed clinical condition, or a distortion along the PHM, calculate or project a potential path range of the first particle density, and then calculate or project at least one other path range of at least a second particle density based on the first particle path and the clinical condition and or distortion. The processor 200 may project or calculate a cascade of paths based on the first particle path and the clinical condition and or distortion. The processor 200 may be programmed to generate a color rendering of an image of the matrix and to project the path as a color rendering. The rendering may have an appearance of radar weather display and the path may be projected as a color rendering, which may be a time lapsable motion image having an appearance of a path of weather progression over time.

In an example, based on the projections for H2CO3 provided in the above example, in a patient with sepsis, the processor 200 may project a H2CO3 of 12 in 12 given a projected fall rate of based on the present rate of fall and a value of 12 in 6 hours based on a "near worst case" fall rate. The projected respiratory rate when the H2CO3 is 12 likely exceeds 30. Therefore a rate range may be projected by placing the rate at 30-36 in 12 hours for a present rate based display and at 30-36 in 6 hours and the paths connected back by the processor 200 to the instant respiratory rate on the display. A similar approach may be taken for heart rate which would be projected in an individual less than 60 without heart disease or beta blocker to be about 130-140 when the H2CO3 is 12. These projections need not be precise as they are presented to warn of the likely dynamic consequence associated inaction in the face of this projected perturbation in particle density and to teach the physician to think of the projected future based on the dynamics of the particles in the present and the disease or disorder present.

The processor 200 may be programmed to project the time range of arrest or intubation based on these parameters. Similar projections may be made for example the anion gap anion may be projected and the dyspnea index.

In one embodiment the efficiency of testing is quantified. In one embodiment the pattern of testing is analyzed to determine the pattern of testing and the pattern of testing is analyzed to determine the correctness, timeliness, and the efficiency of testing. The pattern of testing includes, for example the distribution and timed frequency of a single type of test, or all tests, particularly in relation to a clinical condition such as sepsis. According to one aspect of some embodiments, the processor 200 identifies the pattern of distribution of testing for sepsis. Patterns of sepsis diagnosis associated with a favorable outcome are then compared to identify the most efficient patterns such as a pattern which demonstrates a high frequency of tests early along the sepsis pattern or a pattern which comprise a high testing frequency maintained until the onset of recovery has been identified or a decision to reduce care due to futility or family preference has been specified.

One processing method for optimizing the detection of sepsis comprises, generating a distribution of testing in relation to time and/or at least a portion of the image of the sepsis, comparing the distribution to destitutions of testing associated with a favorable outcome, comparing the cost of testing, identifying at least one testing distribution for sepsis, which has a favorable cost and outcome. The method may compare the distribution of the number of tests per unit time and the distributions of each type of group of tests per unit time in relation to the onset of the sepsis pattern or another aspect or portion of the sepsis image.

In one embodiment the relationship between binaries, and in particular, falphas and their fbetas are non-consuming. In other words, the processor 200 creates binaries of all possible connections rather than the first or a statistically preferred connection. Once all possible connections are created (i.e. those that meet the criteria as specified) then the processor 200 may further characterize the set of possible falphas per fbeta to indicate a continuum of probabilities per binary identified. This continuum may be constructed using the probability matrix as described above as well as other mechanisms of proximity, similarity of severity to name a few. Further, the PHM processor 200, once a non-consuming pass has been accomplished, may include a second consuming pass in which at least one "best fit" models is proposed. In one embodiment, the healthcare worker is provided with an environment in which a set of "best fit" models are presented. The healthcare worker may interact with the models through gestures using a mouse, touch surface, keyboard, and/or natural interface to name a few. For example, the healthcare worker may identify links to be "suspect" or otherwise unlikely. As well, the healthcare worker may indicate a link as "highly likely" or otherwise indicated as preferred. The processor 200 continuously processes the "best fit" algorithms given the new weights provided by the healthcare worker. Outputs of the "best fit" models would provide transparency indicating the alternatives that were rejected as well as the results of the healthcare worker gestures which were included in the weighting of diagnostic options.

In an alternative embodiment, the healthcare worker and/or student is provided with an environment presenting the model with no force designations, or only very low level force designations. The healthcare worker and/or student may then "solve" the model by selecting forces that satisfy the extant occurrences. One or more diagnosis may be added at a specific point in time to indicate the apical force.

In one embodiment, a perturbation (and/or a force, recovery, binary, quaternary or polyquaternary) is programmed to be aware of its state as a solved or unsolved perturbation and to have a "seeking state" wherein it seeks its binary and quaternary links. The seeking state may be defined by game theory and the strength of the seeking may be defined by the type of perturbation and the potential time dependency and severity of the risk associated with the potential solutions. As other seeking perturbations find their forces and recoveries, the new binaries or quaternaries become potential matches for the seeking perturbation. The seeking state may continue after one or more solutions. The seeking and self-solving binaries and quaternaries and manual, semi-manual, or automatic distortion building also provides an education function. This education may be provided as a video game for dynamically building PHM distortions (for example fbeta cascades or polyquaternaries) and rendering a diagnosis and treatment as a function of the building. With this game, the student is learning a new science of computer assisted dynamic relational diagnostics.

In one example of such a video game, the student is first presented with an PHM to review for a time interval, the PHM provides a history by going back in time along the PHM or viewing historical segments which may be compressed or time-lapsed and by reading the linked narratives or attached digital files. For those who may be inclined, the PHM may also be viewed as a naked objectified matrix (as for example in FIG. 6), with the forces, perturbations, and recoveries, and their features identified and color coded for severity. The student may use supplemental viewers presenting for example weather maps or other dynamic views, examine the raw data in tabular form or as manipulate able time series matrices.

After preparing, the student is then shown the PHM with a dynamic distortion (which may change more quickly that the real distortion) emerging which will generally be comprised of only perturbations such as particle density perturbations. The student can link a sufficient portion of the perturbations and recoveries if any for the student to identify a disease or disorder which likely as induced the polyquaternary. The student is expected, upon seeing the primers, to recognize the need for other tests, order them, and link the new test results in the PHM to grow the distortion (for example the polyquaternary). The distortion (and the polyquaternary if the entire distortion is being built) at this time will be incomplete and comprised primarily of linked perturbations. The student is then expected to solve the polyquaternary (the distortion of the PHM), by for example inserting the correct apical falpha which comprises the final diagnostic step in the solution and the insert the correct treatment falpha, which may comprise the final solution step. Upon insertion of the treatment, the game may then insert a range of other forces along the distortion and present a time lapse of the PHM showing the anticipated recovery and resolution of the distortion of the PHM. In one scenario, a new distortion (as for example induced by an adverse drug reaction) may arise and the student will need to solve this distortion without allowing the original distortion from recurring.

In one embodiment the processor 200 may generate a dynamic two or three dimensional parallel construct from medical data, and to analyze the construct for dynamic distortions indicative of at least one of disease, drug reactions, age related declines in function, or clinical failures, the construct comprising a highly organized time matrix comprised of grouped, bonded, linked, related, encapsulated, or otherwise connected; perturbations, perturbation forces, recoveries, and recovery forces. The processor 200 may generate a time-matrix construct of electronic medical data comprised of perturbation of particle densities linked to the forces which may have induced the perturbations.

In one embodiment a processor 200 may be programmed to generate one processor 200 programmed to generate a time-matrix construct of electronic medical data comprised of perturbation of particle densities linked to the forces which may have induced the perturbations. Alternately or in combination a processor 200 may be programmed to generate an image of electronic medical data comprised of dynamic color displays responsive to linked dynamic quaternaries comprised of perturbations, perturbation forces, recoveries, and recovery forces.

A processor 200 may be programmed to generate a time matrix which comprises linked particle densities, exogenous forces, endogenous forces, perturbations, and recoveries and an analysis comprising; detection, identification, quantification, and tracking of cascading perturbations, the forces inducing the cascading perturbations, as well as triggering events (such as a surgical procedure) which may have induced the forces. Alternatively or in combination at least one processor 200 may be programmed to process medical data, detect a grouping of linked perturbations and perturbation forces, detect a cascade comprised of the grouping, search the medical data for at least one apical force which induced the cascade, and output an indication of the apical force.

A processor 200 programmed to process medical data, generate a time matrix comprised of the medical data, detect a grouping of linked perturbations and perturbation forces along the time matrix, detect a cascade comprised of the grouping among the time matrix, detect a grouping of linked recoveries and recovery forces along the time matrix, and output a dynamic timed image responsive to the time matrix. Alternatively or in combination at least one processor 200 may be programmed to convert the medical data into a time series matrix of objects comprised of linked objects of binaries comprised of perturbations and the perturbation forces which induced the perturbations, and recoveries, and the recovery forces, and recovery forces which induced the recoveries, store the time series matrix in a data repository, and periodically adding new binaries onto the matrix over time.

A processor 200 may be programmed to process medical data, generate a time matrix comprised of the medical data, detect a grouping of linked perturbations and perturbation forces along the time matrix, identify linkages which comprise history primers and, upon the detection of one or more primers generate one or more questions for the patient to focus the history in response to the linkages. Alternatively or in combination at least one processor 200 may be programmed to identify linkages which comprise image primers and, upon the detection of one or more image primers generate one or more tests to be performed on the patient to complete the image.

One processor 200 may be programmed to generate an image of a patient's medical data comprised of at least one perturbations, perturbation cascade, force binary, force binary cascade, quaternary, or polyquaternary. The processor 200 may generate a parallel construct such as a time matrix of a patient's medical data comprised of a plurality of linked binaries wherein each binary is comprised of a perturbation and the force which induced the perturbation, or wherein each binary is comprised of a perturbation and the force which induced the perturbation, or wherein each binary is comprised of a perturbation and the force which induced the perturbation.

A processor 200 may be programmed to order tests based on detection of at least one force binary, force binary cascade, quaternary, or poly quaternary. The processor 200 may generate an image of a patient's medical data comprised of at least one perturbations, perturbation cascade, force binary, force binary cascade, quaternary, or polyquaternary, and identify an image primer comprising a partial image of a clinical condition, and order tests and/or treatment based on detection of the image primer to a render sufficient portion of the image to identify the image and/or to treat the likely condition inducing the image. One embodiment comprises a processor 200 programmed to generate a time matrix comprised of force binaries, the processor 200 further being programmed to provide a process for linking of lab values in the time matrix to build a distortion so that the student may learn to construct mental images of the dynamic building process of human pathophysiologic distortions in response to disease or adverse drug reactions.

A processor 200 may be to identify a clinical condition or pattern, based on the clinical condition or pattern calculate a potential worst case path or value of the lab value, identify the retesting time based on the minimum change of the parameter which would have clinical relevance and which may include the expected delay in lab reporting in relation to the ordered testing time, and order the lab test for a future time, based on the calculated retesting time.

A processor 200 may be programmed to identify the clinical condition or pattern, and based on the clinical condition or pattern calculate or project a potential path range over time of at least a first particle density, and output the expected path range of the first particle density on a display. The processor 200 may be further programmed to, based on the clinical condition or pattern, calculate or project a potential path range of the first particle density, calculate or project at least one other path range of at least a second particle density based on the first particle path.

The processor 200 may be further programmed to, based on the clinical condition or pattern, calculate a potential path range of at least a first particle density, and calculate a plurality of path ranges for a plurality of other particle densities based on the clinical condition and the first particle pathway. The processor 200 may be further programmed to, based on the clinical condition or pattern, calculate a potential path range of at least a first particle density and calculate a path range for a cascade of particle densities based on the clinical condition or pattern and the calculated or projected path range of the first particle density.

One processor 200 may programmed to compose interconnected cascades of physiological occurrences by combining into a quaternary four elements or objects comprising, a perturbation, at least one perturbation force which is capable of inducing and may have induced the perturbation, a recovery, at least one recovery force which is capable of inducing and may have induced the perturbation. The quaternary may be defined or its construction triggered by the detection of at one of the elements. The quaternary may be characterized as solved or unsolved. A quaternary may be are considered solved when all four elements are included, the collection of perturbation forces is determined to be compatible with the perturbation, and the collection of recovery forces is determined to be compatible with the recovery. A perturbation in one quaternary may be a perturbation force in another quaternary. A perturbation in one quaternary may be a recovery force in another quaternary. Any element in a quaternary may also be any element in a different quaternary. Interconnected cascades of quaternaries may be identified as candidate causation models for a patient condition. At least one candidate apical force 700 may be determined as the first perturbation force within a cascade. The identification of apical force may 700 be used by the processor 200 to identify or produce a diagnosis. At least one causation model may be displayed to a healthcare worker. At least two causation models may be compared. At least one preferred or "best fit" causation model may be determined. Unsolved quaternaries such as 702A and 702B of FIG. 7 can be displayed and/or initiate testing or a change in frequency of testing and/or be tracked as a time series and/or initiate an alarm. Solved and unsolved quaternaries 702A and 702B are identified on a color weather map visualization. A healthcare worker may select and/or weight the solution to a perturbation and/or recovery.

As discussed, in one embodiment perturbations, recoveries, binaries, quaternaries and polyquaternaries have seeking states and non-seeking states. The "seeking gravity" of the state can depend on factors such as risk, cost of finding solutions, and/or other factors. A high number of unsolved perturbations or perturbations with a large "mass" (as defined, for example by a potentially high risk), generate an "unstable" image with high internal gravitations forces. The image is stabilized when the seeking state of the perturbations is mitigated or resolved by either finding the matches or by being instructed (manually or automatically, as by internal "seeking buffers") to stop seeking.

In one embodiment a game can be constructed to show how the program functions and to teach the pathophysiology of distortions. The program can have a "game mode" allowing insertion of real or simulated physiologic data to generate a plurality of perturbations and forces. At least a portion of these will have no solutions so they will begin seeking. The presence of seeking perturbations can be designated by moving or otherwise enhanced graphical avatars, geometric shapes, or icons. As a first perturbation finds its match(es) a resulting solved binary and/or quaternary (which may be seeking) is generated. A second seeking perturbations may then find the solved binary and/or quaternary as its solution. This may produce a automatically growing cascade comprising a global solution and relieving the gravitational instability. All of this can occur on a graphical image building a moving image as the components seek each other and come together to for a solved game.

In one embodiment the seeking is bilateral and the gravitational pull between two mutual seekers is defined by a new and often much larger force related to the risk associated with the combination of the seekers. In an example a perturbation comprising a fall in bicarbonate is seeking a plurality of perturbation forces, one of which is a rise in absolute band count. A rise in absolute band count is also seeking a plurality of perturbation forces is a fall in bicarbonate. If a rise in absolute band count finds a fall in bicarbonate they are attracted by a very high force because the combination suggests a time dependent dangerous condition which can evolve rapidly.

In one embodiment, vector analysis is performed to provide insight into diagnostic paths for patient conditions, failure modes, and clinical failures. Patient conditions, failure modes, and clinical failures are associated with one or more object types. Each object type has a set of instances (occurrences) per patient. Vector analysis reviews the paths leading to the condition or failure in time to provide insight into the evolution of perturbation and/or recovery. The analysis also provides a method for improving retrospective quality review. Further, vector analysis can be utilized to refine the definition of occurrences within an image or cascade to improve sensitivity, specificity or other correlatively feature.

A complex object type represents a tree structure of other object types of which it is composed. For example, if X is a binary of type A and type B, then X has a tree structure in which X is a tree and A and B are leaves of the tree. In this simple case, if X was associated with a condition, failure mode or clinical failure then vector analysis would consider X to have two diagnostic paths: A→X, B→X. In the domain (XAB) A and B are considered initial types and X is considered a diagnostic type. Were a single instance of X to be identified for a patient, then there would be two diagnostic path traversals (OA1→OX1) and (OB1→OX1) where OA1, OB1, and OX1 are Occurrences of types A, B and X respectively in which OA1, OB1 are components of the binary OX1.

Figure 8:
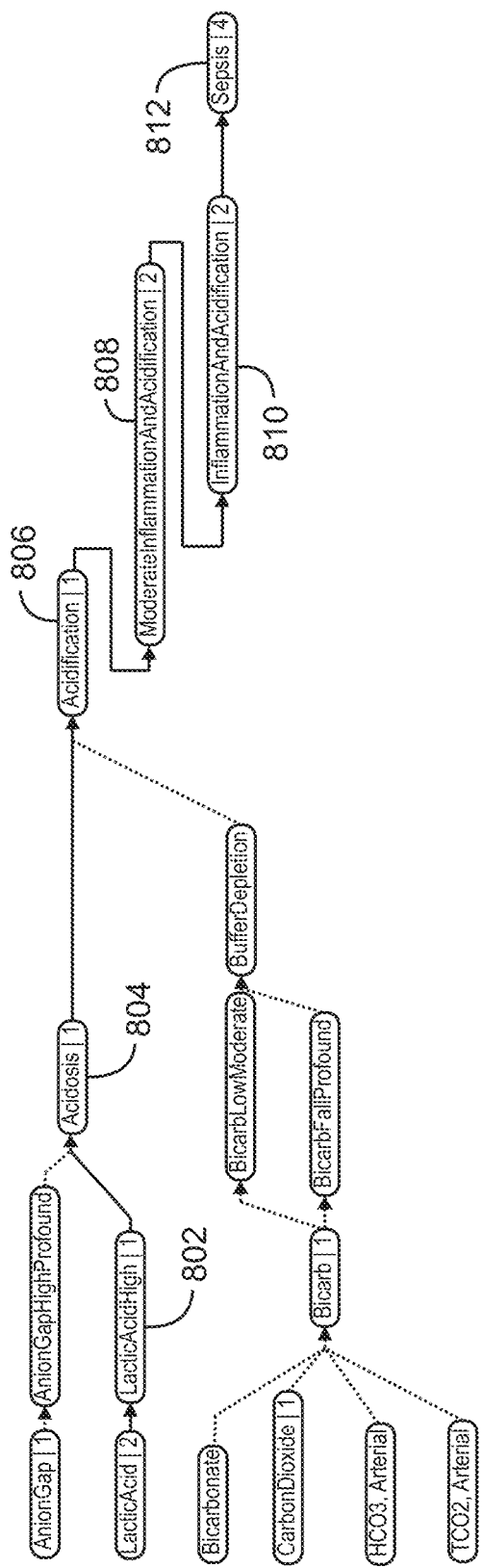
FIG. 8 depicts a single complete diagnostic path traversal for Sepsis in which solid lines between types of perturbations indicate traversal and dotted lines between types indicate no traversal. The instance depicted has an initial occurrence of LacticAcidHigh traveling through Acidosis, Acidification, ModerateInflammationAndAcidification, and InflammationAndAcidification to Sepsis.
Figure 9:
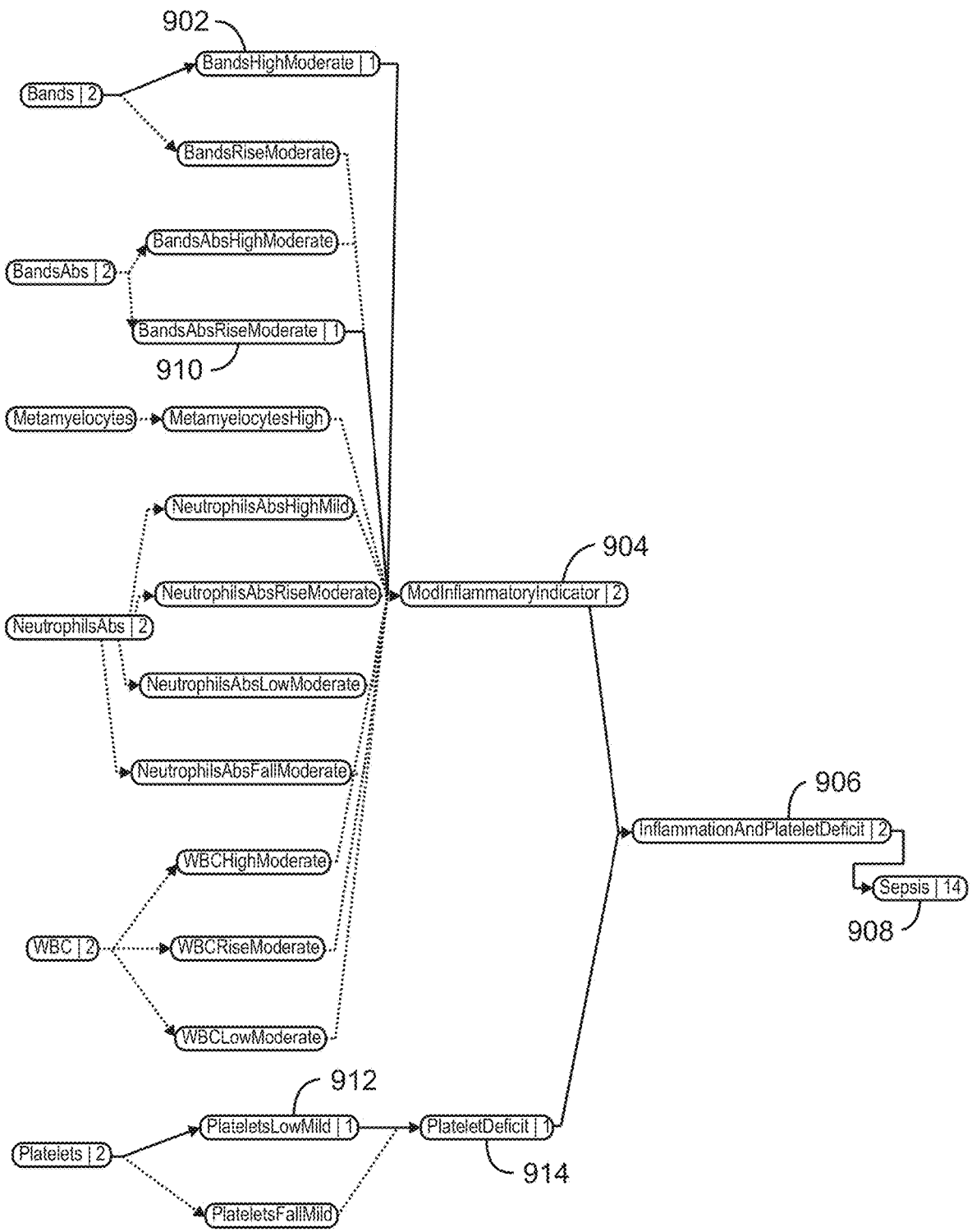
FIG. 9 depicts multiple complete diagnostic path traversals for Sepsis in which solid lines between types of perturbations indicate traversal and dotted lines between types indicate no traversal.

In more complex scenarios, a diagnostic path traversal would have the structure of I→L1→Ln→D where I is the initial occurrence, D is the occurrence indicative of the condition and L1 through Ln are linking occurrences. For example, in FIG. 8 a single diagnostic path traversal is shown. The path with a solid line (as opposed to a dotted line) indicates the actual traversal of one or more occurrences. FIG. 8 shows a single traversal traveling from LacticAcidHigh 802 through Acidosis 804 through Acidification 806 through ModerateInflammationAndAcidification 808 through InflammationAndAcidification 810 to Sepsis 812. As another example, in FIG. 9 we can identify three complete diagnostic path traversals. The first diagnostic path traversal has an initial occurrence type of BandsHighModerate 902 and then proceeds through ModInflammatoryIndicator 904 then InflammationAndPlateletDeficit 906 and then to Sepsis 908. The second diagnostic path traversal has an initial occurrence type of BandsAbsRiseModerate 910 and then proceeds through ModInflammatoryIndicator 904 then InflammationAndPlateletDeficit 906 and then to Sepsis 908. The third diagnostic path traversal has an initial occurrence type of PlateletsLowMild 912 and then proceeds through PlateletDeficit 914 then InflammationAndPlateletDeficit 906 and then to Sepsis 908.

Given a patient matrix, vector analysis will derive 0 or more complete diagnostic path traversals. For example, given the domain (XAB) used above, if a patient has two instances of the X object then (given that both components of a binary are required) there will be 4 complete diagnostic path traversals.

Object types, such as classification which have optional or variant sources provide variability in paths. For example, if a classification Q is defined as R or S or T then in the domain (QRST) there are 3 diagnostic paths: R→Q, S→Q and T→Q. If a patient has two instances of Q then (given that a classification is created from any one of its sources alone) there will be two complete diagnostic path traversals.

Diagnostic path traversals provide the basic building block of vector analysis. In one embodiment, diagnostic path traversals are represented as records with the following fields: condition, patient id, diagnostic instance id, diagnostic instance type, diagnostic instance earliest identification time, initial instance id, initial instance type, initial instance earliest identification time, diagnostic path traversal signature, and primary sub-path.

In one embodiment, the diagnostic path signature is defined as a string containing the path elements listed with a connector (e.g. "→"). For example a path signature from the complete traversal in FIG. 8 is the string: "LacticAcidHigh→Acidosis→Acidification->ModerateInflammationAndAcidification→InflammationAndAcidification→Sepsis".

Since conditions are often defined in terms of a classification (i.e. a statement with a list of alternatives separated by an 'or' operator) it is useful to consider primary sub-paths into a condition. If, for example, Sepsis is defined as "SIRSSevere or InflammatoryAugmentationProfound or SIRSandRespFailureMod" then there are at least 3 primary sub-paths into Sepsis. If any of these three elements specified are themselves simple classifications (e.g. a list of alternatives separated by an 'or' operator) then the members the classification will replace the original classification as primary sub-paths. This process is repeated until all primary sub-paths are identified. Therefore, the primary sub-path is a direct unqualified gateway into the condition. More formally this is specified as a type for which an occurrence will be guaranteed to become an instance which indicates the condition but for which arriving occurrences to the type are not.

Primary sub-paths provide a top-level differentiation of diagnostic paths and are much more cognitively manageable than an entire diagnostic path.

In one embodiment the diagnostic path traversal record contains any reference information necessary to access the occurrence instances represented in the path.

In one embodiment additional key characterizes (e.g. Severity Category) are included in the record and in the path signature to provide additional specification.

In addition to instances of complete diagnostic path traversals, vector analysis identifies and maintains partial path traversals. Further analysis can be done to identify the reasons that the path did not become a complete diagnostic path traversal. Failure reasons are derived by determining all of the next steps that could have been taken. For each candidate next step a failure reason (e.g. no SevereInflammation found within 1 day) is derived and stored.

In one embodiment, failure reasons are stored by the real-time engine during execution. In one embodiment, a minimum distance is specified indicating the number of steps required from the end of the path traversal to the type indicating the condition. In one embodiment additional information is provided to quantify the failure (e.g. indicating by "how much" a qualification was missed).

In one embodiment partial diagnostic path traversals are aggregated along with complete diagnostic path traversals. These records include failure reasons, distance from diagnosis and potential primary-sub paths to name a few.

Figure 10A:
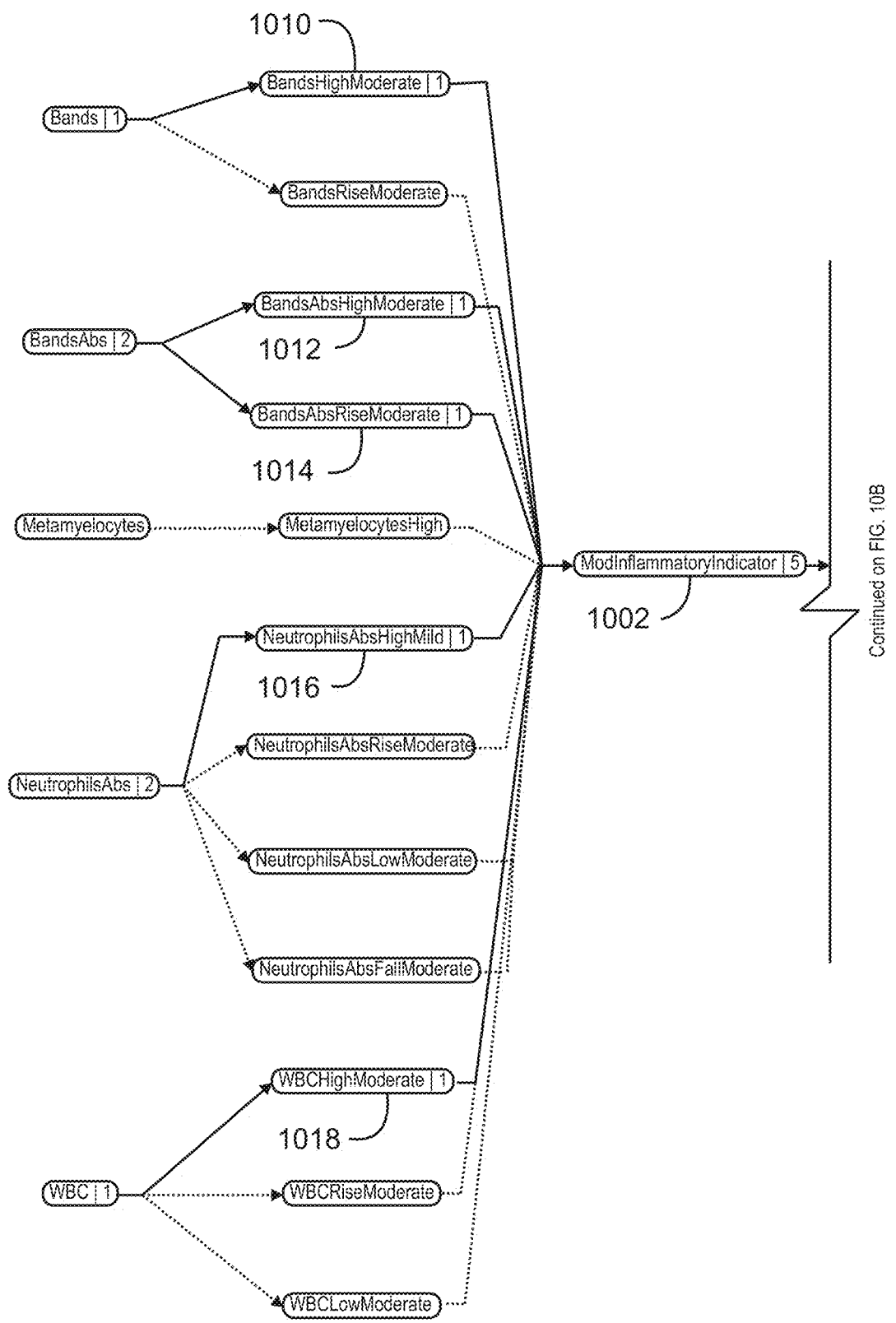
FIGS. 10A and 10B depict multiple complete diagnostic path traversals for Sepsis. In the example illustrated in FIGS. 10A and 10B, the path traversal for Sepsis includes the ModInflammatoryIndicator. The solid lines between types indicate traversal and dotted lines between types indicate no traversal. In the case illustrated in FIGS. 10A and 10B, 3 primary sub-path traversals are shown—SequentialInflammationInjury, InflammationAndPlateletDeficit, and InflammationAndAcidification. Further, 3 other primary sub-paths are shown as not being traversed—InflammationAndIonCalciumFall, InflammationAndAlbuminFall, InflammationAndCalciumFall.
Figure 10B:
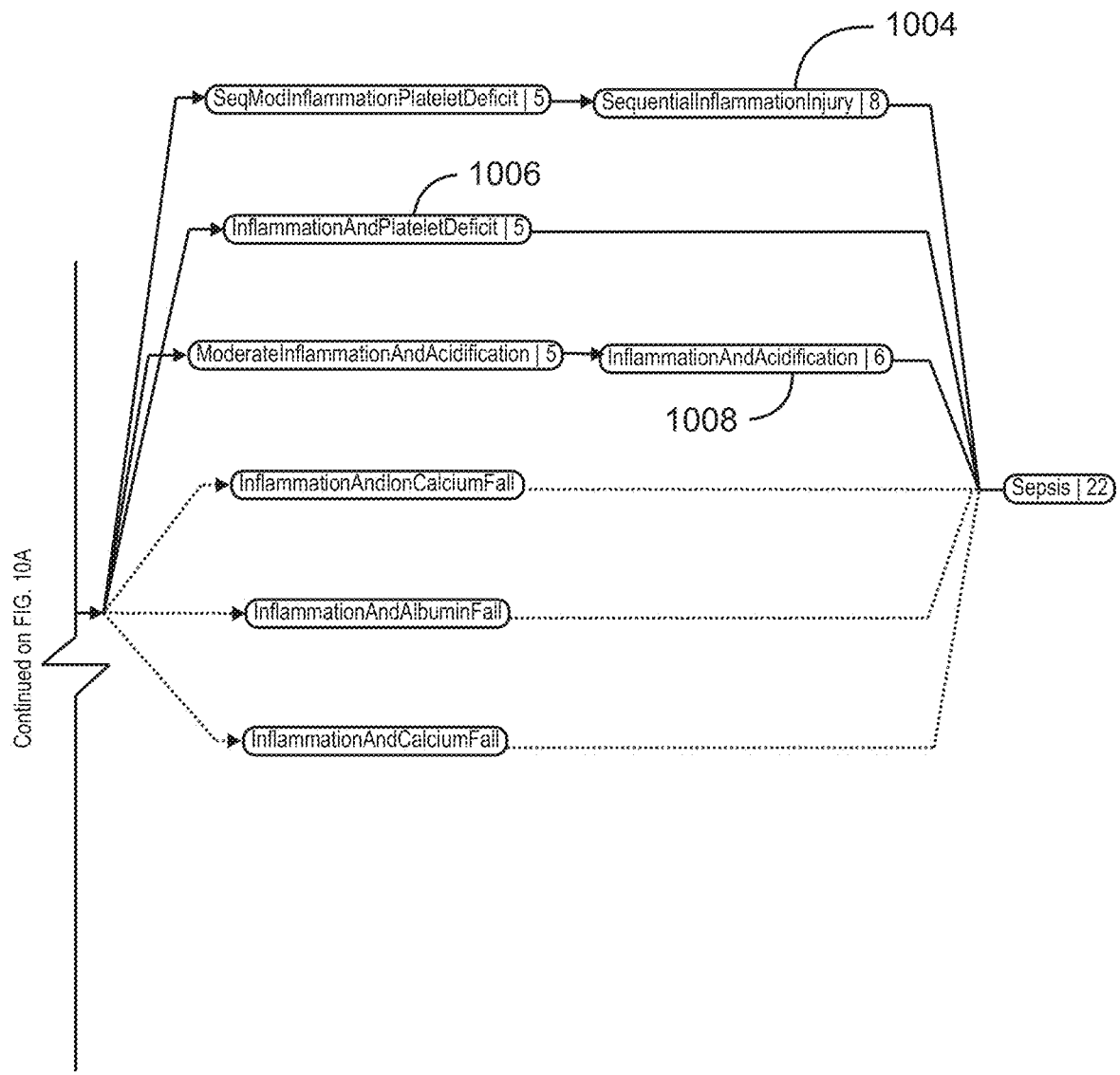

Having a comprehensive set of partial and complete diagnostic path traversal records provides a powerful mechanism for analysis and deriving insight into patient condition, disease evolution and recovery. For example, in FIG. 10 the filtering of path traversals by ModInflammatoryIndicator 1002 shows initial types, paths and primary sub-paths through which Sepsis identification was accomplished for a given patient at a specific point in time. FIG. 10 shows, for example, that 3 primary sub-paths used for the traversals (SeqentialInflammationInjury 1004, InflammatioNAndPlateletDeficit 1006 and InflammationAndAcidification 1008) are dependent on the identification of ModInflammatoryIndicator 1002. Further, it is clear that 5 different initial types (BandsHighModerate 1010, BandAbsHighModerate 1012, BandsAbsRiseModerate 1014, NeutrophilsAbsHighMild 1016 and WBCHighModerate 1018) are triggering ModInflammatoryIndicator 1002.

Alternatively occurrence definitions can be analyzed in the context of sensitivity/specificity analysis or other statistical analysis to refine the definitions either automatically or through the direction of a medical expert. In either case, metrics can be derived by sorting, filtering and aggregating this set. Analysis can be executed against large patient populations, sub-groups or single patients to name a few.

For example, given a patient set, vector analysis can indicate what the top 5 initial paths to Sepsis are for patients over 60 who contracted Sepsis in-hospital.

Basic metrics can be derived around an occurrence within the traversal, a type within the traversal, an initial occurrence, an initial occurrence type, a condition, a diagnostic path, a path signature, a traversal signature, a primary sub-path, a potential primary sub-path, or a failure reason to name a few. Metrics can be derived in counts and percentages both of instances and/or patients.

In one embodiment, a time series of metrics is derived by performing or deriving vector analysis at multiple points in time over the patient stay. In one embodiment, metrics are derived continuously per point received within the system. It is particularly useful for a comprehensive understanding of condition evolution that filters and a time-series approach be used in concert. In one embodiment a patient group is filtered down to limit the set to patients which acquired the condition while being monitored (e.g. in which initial identification of the condition is >28 hours past admit time) and a time series of metric points is created using time in reference to the initial condition identification point. For example, starting with 18 hours before initial identification of Sepsis the primary sub-path percentages are sampled in 2 hour increments. In this way a set of metric time series is created that can be further analyzed. For example, it may be determined that a particular primary sub-path is the ranked as the highest sub-path for the first 12 hours of Sepsis within a specific patient group.

Within these time-series patterns of thresholds, trends, binaries, images and repeating occurrences to name a few can be derived, analyzed and displayed. For example it may be determined that a particular primary sub-path tends to increase from 6 hours since identification to 24 hours since identification and then fall off.

Metric analysis has a wide range of applicability. It can be used for real-time analysis of patient state, analysis of overall disease and recovery evolution in patient populations, and in support of condition script creation/refinement to name a few.

In terms of script refinement/creation vector analysis can provide both false-positive and false-negative analysis.

In one embodiment, false-positive analysis is accomplished by limiting the patient set to patients that have been identified to false positives. Further, within that group, sub-groups can be defined and focused on. For example, a researcher could choose to work on a sub-group of false positives that are identifying patients through a specific primary sub-path (e.g. SIRSandRespFailureMod). Once a patient group has been defined (or a single patient selected) vector analysis provides insight in to the initial occurrence (events that became components of the condition), paths, and primary sub-path.

Top Initial Occurrence Types can be identified and further analysis can be done on them. For example, range analysis can show a distribution of values that fell within the range required indicating whether a small adjustment in the qualification range may eliminate a number of path traversals. In one embodiment, this analysis is automated to combine range-analysis with "what if" scenarios to find range adjustments that eliminate false-positives without creating false negatives.

Top Primary Sub-Paths gives a high-level insight into how false-positives are reaching the condition providing direction into what adjustments will be most effective.

Hot paths can give more detailed insight into how the approach vectors are being reached. Traversals can further be analyzed to find hot links—specific relationships that may be defined to liberally in terms of time or qualification.

In one embodiment, false-negative analysis is accomplished by looking at partial diagnostic path traversal within a condition and reviewing failure reasons within a false-negative group of patients. Near paths can be determined by finding failure paths with the minimum distance values. Ranking can be done by distance or quantification of failure to name a few.

In one embodiment partial and complete traversals are viewed, sorted, filtered, grouped and ranked at the same time. In this way true positives and true negatives can also be engaged to strengthen the script by increasing the mean distance from diagnosis in true negatives or increasing the mean number of identification paths in true positives.

Further, in one embodiment, ignore lists can be maintained to focus on/strengthen aspects of scripts. Ignore lists can be of occurrences within the traversal, types within the traversal, initial occurrences, initial occurrence types, conditions, diagnostic paths, path signatures, traversal signatures, primary sub-paths, potential primary sub-paths and failure reasons to name a few. Ignore lists can be added, updated, deleted and stored.

In one embodiment the brain is identified as a system in the matrix (and distortions may be shown on a weather map or other visualization. Cells may be defined by EEG analysis, for example the detection of severe slowing (a perturbation) and then the cause (the perturbation force) of the severe slowing sought to solve the force binary. Other perturbations such as seizures, or frequent arousals. Outputs of cognitive testing may be converted to R values and/or presented in cells and treated as perturbations in the matrix. In this way persistent perturbation of brain function, for example after sepsis, comprise distortions in the matrix which may be tracked using visualizations such as persistent storm cells on a portion of the map relating to the brain.

As described earlier in one embodiment features of perturbations (slopes, magnitude, duration, and absolute values) are quantized in relation to phenotypic or other reference range of the features. In a similar way, features of relational perturbations (such as pathophysiologic divergence (decoherence) may be quantized in relation to phenotypic or other reference range of the features. The term "decoherence" may be used interchangeably with pathophysiologic divergence and with refers to the pattern and/or dynamic behavior or relational pattern and/or dynamic behavior of a density which is not expected. For example, the pattern or dynamic behavior of a biologic particle density may be described as decoherent or decoherent in relation to the matrix, when the pattern or dynamic behavior is exhibiting pathologic behavior. The pattern or dynamic behavior of a biologic particle density may be described as decoherent in relation to the phenotypic matrix, when the pattern or dynamic behavior is exhibiting pathologic behavior. The pattern or dynamic behavior of a biologic particle density may be described as decoherent or decoherent in relation to a distortion when the pattern or dynamic behavior is exhibiting behavior which is not the expected pattern or behavior given the pattern or behavior of the distortion.

The quanta of the features of perturbations or recoveries may be mapped on fixed or movable organelles each of which is responsive to changes in the feature which is mapped on the organelle. Organelles may be positioned in a predefined format (such as, in aggregate, defining a hexagon or another shape) within fixed or movable "perturbation cells" or "recovery cells" respectively. "Perturbation force cells" and "recovery force cells" with corresponding organelles responsive to these cells may be on a mapped on the system and/or organ region to which the perturbation corresponds. Regions which comprise relational regions (for example a combined inflammatory-hemostatic region) may be provided, which are comprised of cells which are "relational perturbation cells", the organelles of relational perturbation cells being responsive to relational features of the perturbations. Each organelle may change (a change may comprise for example, a change in color, density, texture, shape, blinking frequency, or another change) in response to changes in the feature which is mapped to that organelle.

This generates a quantized motion image of a distortion and recovery from the distortion and of the forces inducing the distortion and the recovery. By placing all of the cells and organelles in fixed relationships on a preformatted map with a known format, a large mass of complex relational quantized data is presented in relation to a phenotypic, normal, or baseline state so that distortions due to a one type of pathology exhibit predictable ranges of images on the preformatted map which are useful for facilitating the detection, identification, quantification, characterization, and tracking of that pathology type.

In addition the quantized motion image or fixed snapshots or short segments can be imaged and are analyzable by image based pattern and/or pixel recognition systems or other analysis systems.

As discussed, in one embodiment, perturbations, features or quanta derived from the perturbations and/or features may be converted into image components which may comprise; cells, organelles, shapes, bar codes, shape codes, shades, colors, shapes, numbers, and/or pixels, or other image component renderings derived from the perturbations, features, or quanta.

The image components may be aggregated in relation to the perturbations from which the features are derived and/or in relation to the physiologic system to which the perturbation or features relate and/or in relation their relation to treatment, to which the perturbation or features relate.

Image components may be aggregated in relation to whether they are perturbations, perturbation forces, recoveries, or recovery forces. They may also be derived as relational image components and/or aggregated as relational image components. They may be mapped onto relational systems, or maps for relational perturbations, perturbation forces, recoveries, or recovery forces, binaries quaternaries or other relational patterns.

Any of these image components may be placed into fixed and predetermined positions on the display to render images which would be substantially identical same if the perturbations and features are substantially identical thereby producing reliable image changes. These can then be sequenced over time segments and displayed as fixed or changing images or the predetermined format. Training sets of images can then be displayed to one or more image recognition system, as are known in the art, to train the image recognition system to recognize the clinical condition by imaging the displays.

Large archives of displays can be derived using reliable, definitive, gold standards to train the image recognition systems.

The converting the biologic particle densities and other physiologic data into fundamental features, generating image components responsive to the fundamental features and then generating predefined images mapping provides a data processing and mapping and displaying system which takes advantage of advances made in the field of image recognition by the conversion of these complex data sets into images of sufficient granularity and dynamic relational granularity to allow subtle image differences to be recognized in the training set and then applied in the recognition of the image under test.

The maps which display the image components derived from the perturbations, forces, perturbation features, and/or force features can be standardized, as with the development of an ASTM standard or ISO standard for use of the human or animal biologic particle maps worldwide.

A field of image recognition professionals, similar to the field of radiology may be developed, wherein the professionals are trained in the images and the pathophysiology of the diseases under test and are provided other images, such as the time series matrices of the data to over read the diagnostic output of the image recognition software and thereby protect outlier patients.

In one embodiment the image is divided into components or sections and each section, grouping of sections, and/or the entire image may be used to train an image recognition system. The sections section, grouping of sections, and the entire image may be presented to the recognition system in sequence or otherwise marked for their timing relationships.

The image recognition system can then generated probabilities for the diagnoses which at least partially matched by the image or image segment. The image recognition system or processor 200 may also generate a probability matrix or other probability construct and/or a group of time series or a matrix of time series of the probabilities generated.

In one embodiment the time series matrix of probabilities is objectified and processed in the same way as the time series matrix of biologic particle densities to generate perturbations of probabilities, features of perturbations, and image components of the probabilities, which can themselves be mapped to generate an training archive of probability images which are used to train an image recognition systems. This process may be recursive.

One embodiment comprises a medical device for monitoring dynamic patterns of biologic particle densities comprising a processor 200 programmed to detect and analyze perturbations of biologic particle densities, detect and analyze features of biologic particle densities perturbations and to convert the perturbation features into discreet perturbation feature quanta in relation to a phenotypic, baseline or expected range of the perturbation features.

One embodiment is programmed to generate a first set of images responsive to the perturbations, generate second set of images responsive to the perturbation feature quanta, aggregate the first set and the second set into a time-lapsable motion image to generate a motion image of visualization of combined of perturbations and perturbation feature quanta.

The device may be further programmed to detect and analyze forces which induced or caused said perturbations of biologic particle densities, detect and analyze features of biologic particle densities forces, convert the force features into discreet quanta in relation to a phenotypic, baseline or expected range of the force features and to generate a third set of images responsive to the forces and generate fourth set of images responsive to the force feature quanta.

In one embodiment the processor 200 is programmed to aggregate the third set and the fourth set into a time-lapsable motion image to generate a motion image of visualization of combined of the forces and the force feature quanta. The processor 200 may be future programmed to aggregate the first set and the second set with the third set and the fourth set into a time-lapsable motion image to generate a motion image of visualization of combined perturbations and perturbation feature quanta and forces and the force feature quanta. Quanta may be defined by colors, gradation of colors, integers and ascending and descending sequences of integers or other discrete gradation methods.

Figure 11:
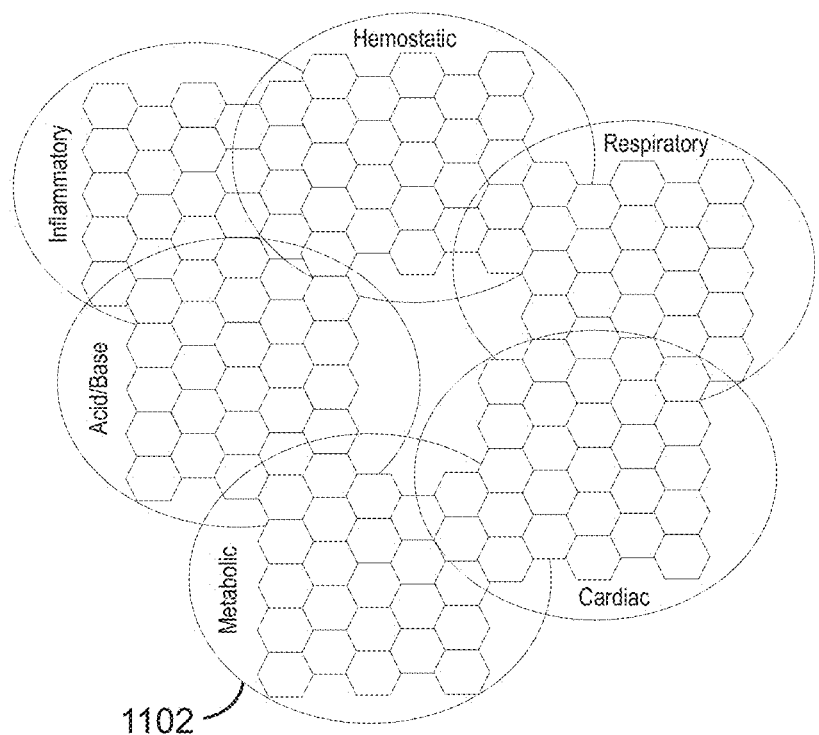
FIG. 11 depicts perturbations, perturbation forces, recovery and recovery forces and/or their features are rendered as hexagons placed within related clinical space systems.

In one embodiment perturbation, perturbation forces, recovery and recovery forces and/or their features are rendered as hexagons 1102 placed within related clinical space systems as shown in FIG. 11. In one embodiment, the hexagons have a fixed location. In one embodiment, the location is based on the severity of the quanta to which the hexagons are responsive. In one embodiment, the relative locations are responsive to severity and/or relationships within and among the associated perturbations and associated features. Alternatively other visual aspects of the hexagons are responsive to the related quanta such as the size, orientation, fill color or texture, border color or texture, transparency to name a few.

Figure 12:
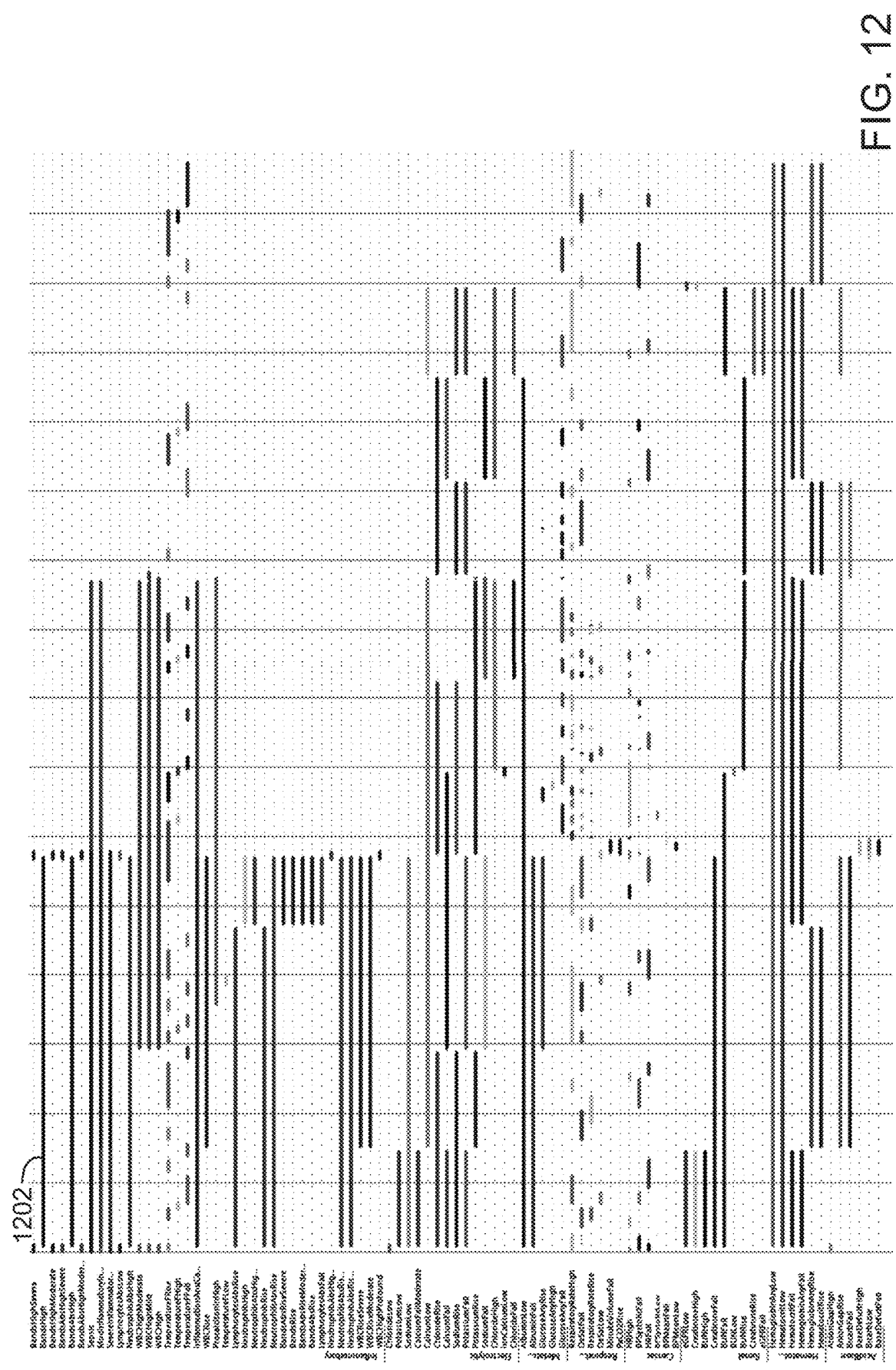
FIG. 12 depicts an image of a severe sepsis patient in which perturbations, perturbation forces, recoveries and recovery forces and/or their features rendered as bars across a two dimensional area in which the location and length of the bar are based on the start and end time of the associated perturbation or recovery and the vertical location is set by the type of the perturbation or recovery grouped by clinical space.
Figure 13:
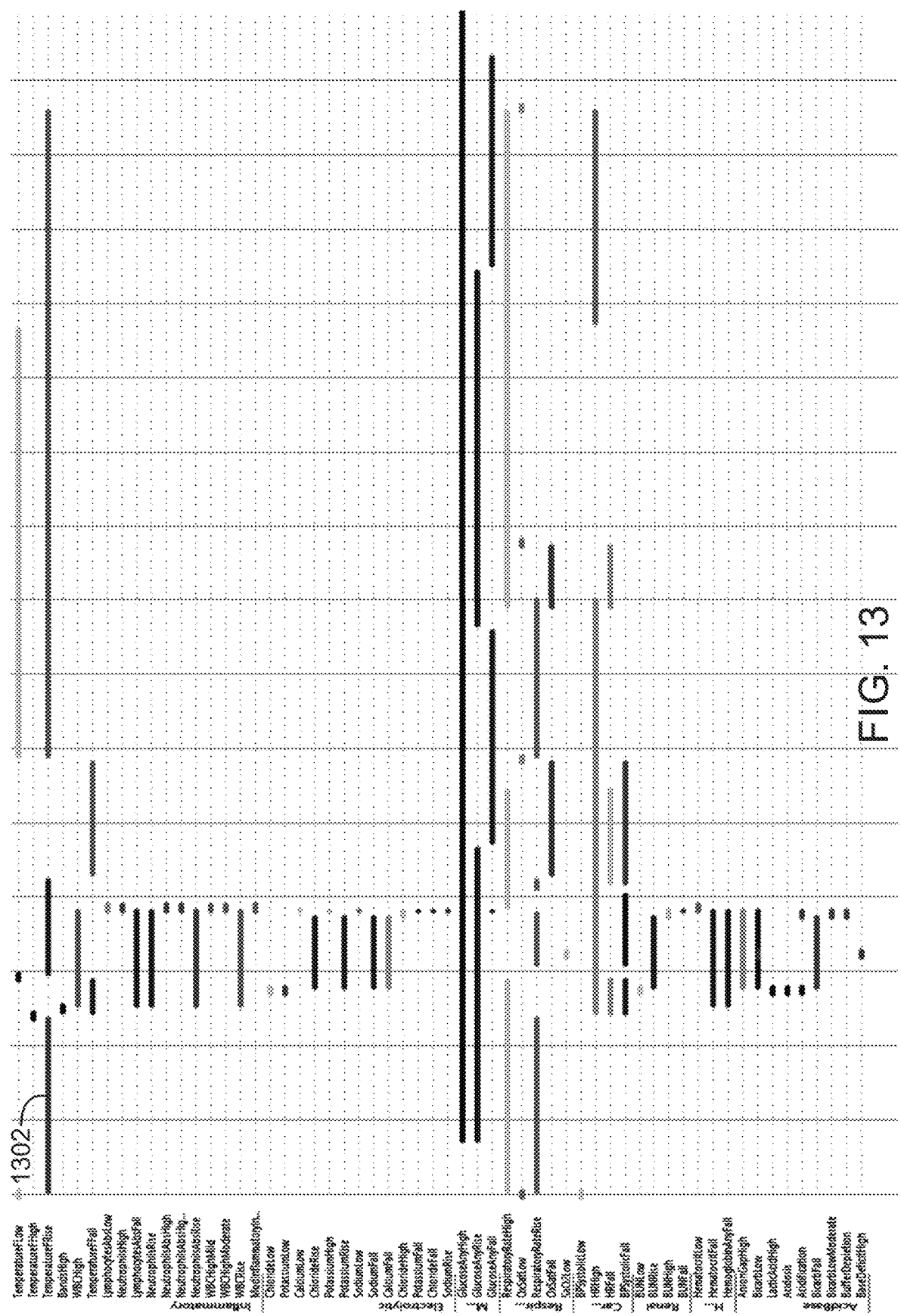
FIG. 13 depicts an image of a sepsis patient which recovered from sepsis in which perturbations, perturbation forces, recoveries and recovery forces and/or their features rendered as bars across a two dimensional area in which the location and length of the bar are based on the start and end time of the associated perturbation or recovery and the vertical location is set by the type of the perturbation or recovery grouped by clinical space.
Figure 14:
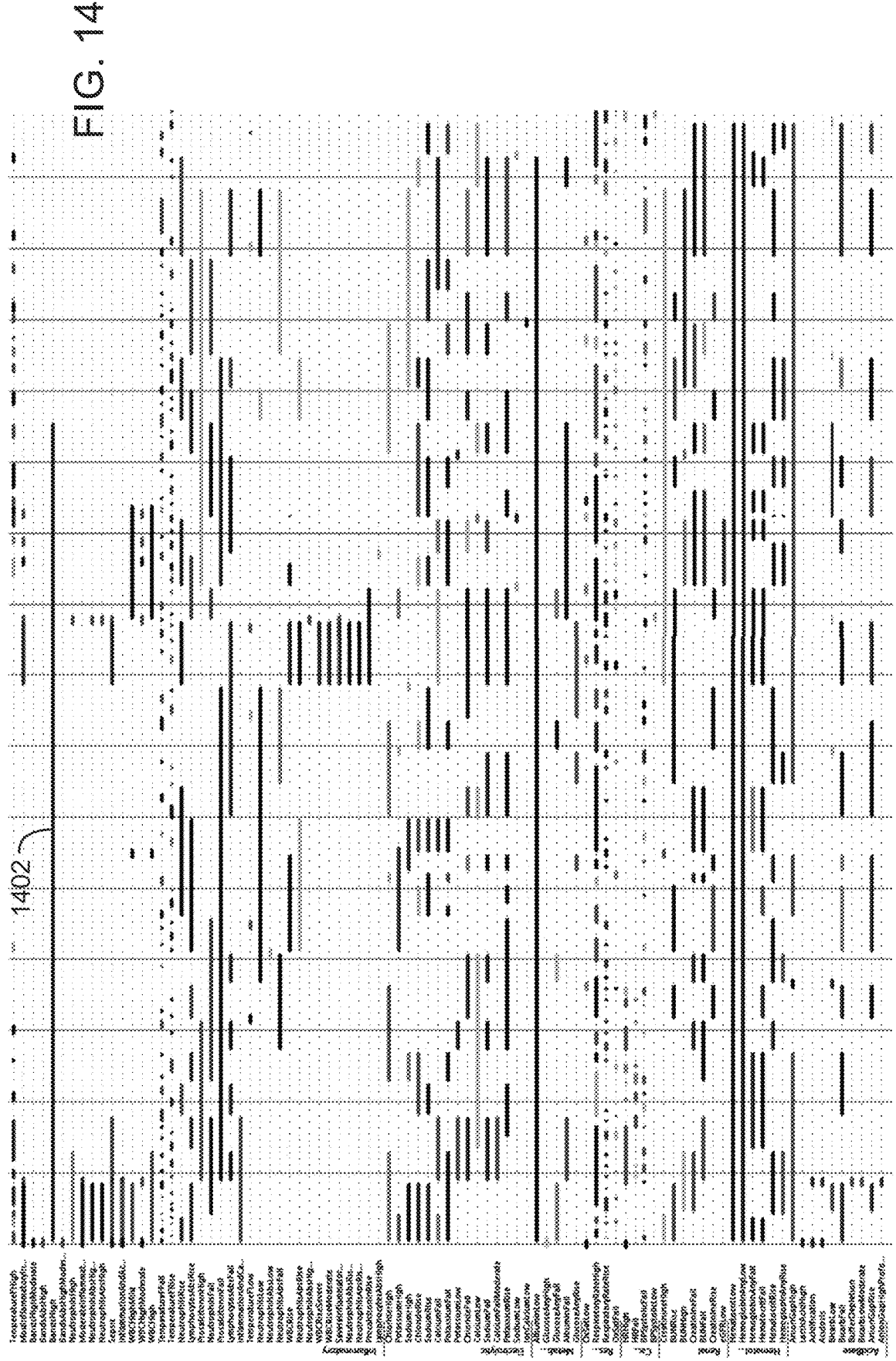
FIG. 14 depicts an image of a long-term severe sepsis patient in which perturbations, perturbation forces, recoveries and recovery forces and/or their features rendered as bars across a two dimensional area in which the location and length of the bar are based on the start and end time of the associated perturbation or recovery and the vertical location is set by the type of the perturbation or recovery grouped by clinical space.

In one embodiment, as shown in FIGS. 12 through 14, perturbations, perturbation forces, recoveries and recovery forces and/or their features are rendered as bars 1202 across a two dimensional area in which the location and length of the bar is based on the start and end time of the associated perturbation or recovery. The vertical location is set by the type of the perturbation or recovery and may be further grouped by clinical space as shown in FIGS. 12 through 14. Other visual aspects of the bars are responsive to the related quanta such as the size, fill color or texture, border color or texture, transparency to name a few.

FIG. 13 depicts an image of a sepsis patient which recovered from sepsis in which perturbations, perturbation forces, recoveries and recovery forces and/or their features rendered as bars 1302 across a two dimensional area in which the location and length of the bar are based on the start and end time of the associated perturbation or recovery and the vertical location is set by the type of the perturbation or recovery grouped by clinical space.

FIG. 14 depicts an image of a long-term severe sepsis patient in which perturbations, perturbation forces, recoveries and recovery forces and/or their features rendered as bars 1402 across a two dimensional area in which the location and length of the bar are based on the start and end time of the associated perturbation or recovery and the vertical location is set by the type of the perturbation or recovery grouped by clinical space.

The bars 1202, 1302, 1402 may be provided in a fixed location and be filled in or otherwise enhanced, modified or visible, only if the data needed to generate the bar was available to the processor 200. Although, predominately perturbations are displayed in the exemplary maps of FIGS. 12 through 14. Each feature or a wide range of relevant features may be mapped onto the map. In this example, a map may contain hundreds or thousands of potential bars 1202, 1302, 1402 which can be very thin lines and/or very thin linear patterns for the purpose of providing them on a single view.

Figure 15:
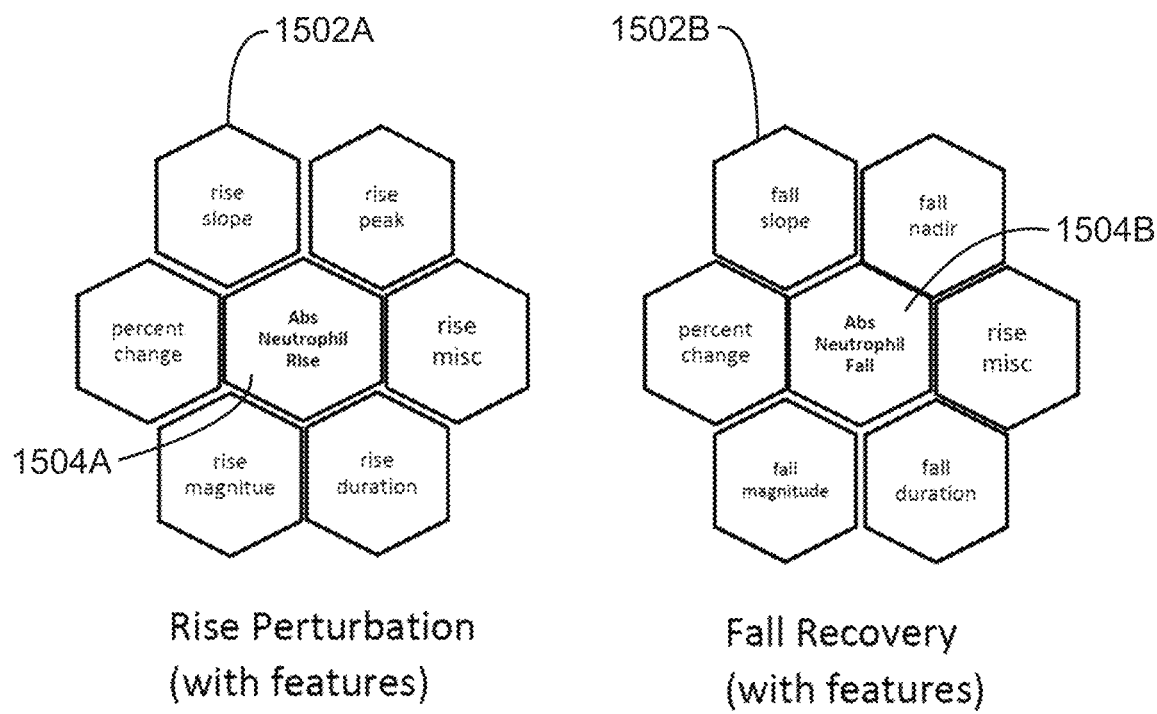
FIG. 15 depicts an AbsNeutrophil rise perturbation and an AbsNeutrophil fall recovery rendered as hexagon clusters that include both the fall and recovery along with their associated features.
Figure 16:
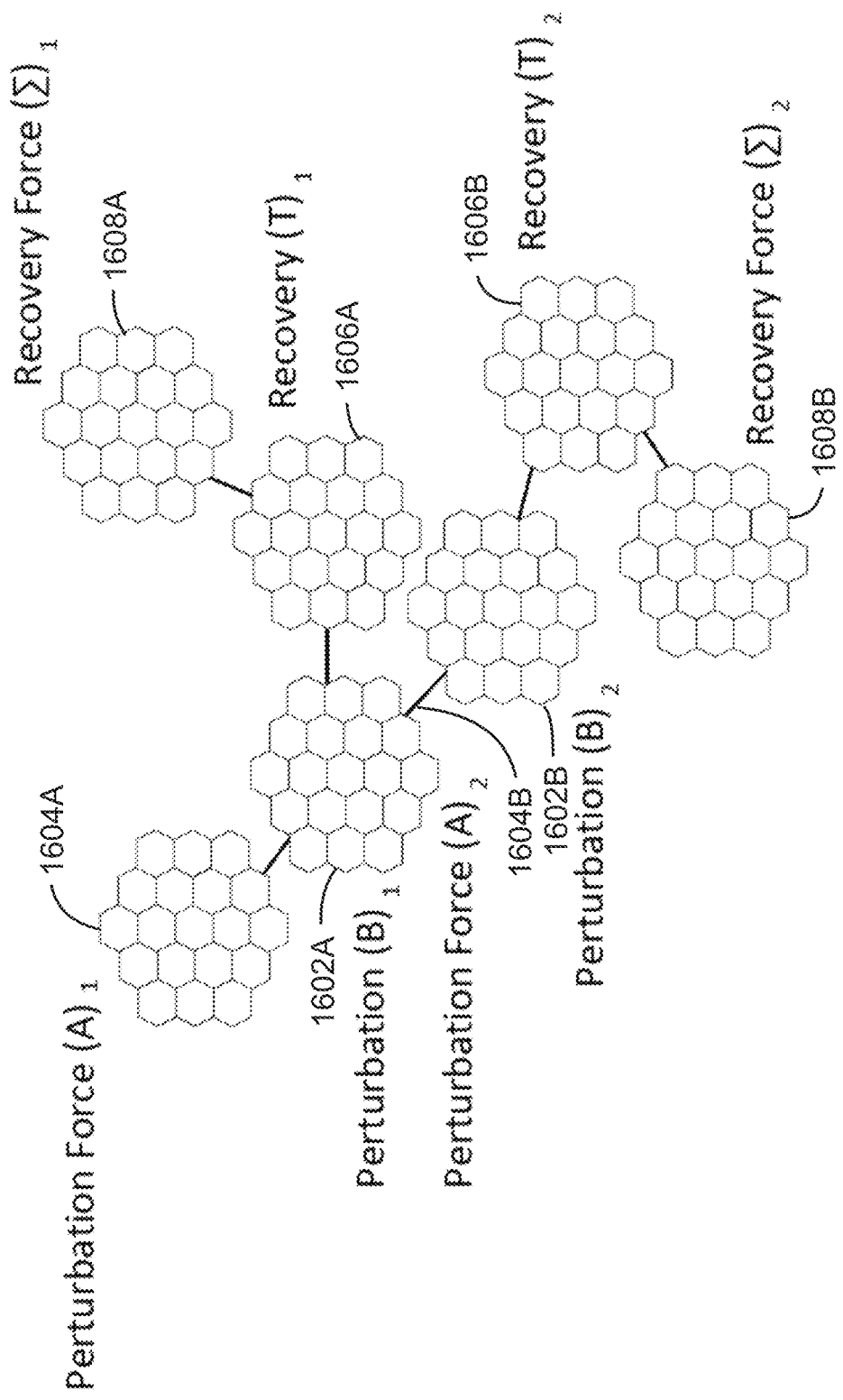
FIG. 16 depicts the two linked quaternaries wherein the perturbation of the first quaternary is the perturbation force of the second quaternary displayed as an image of perturbations, recoveries, perturbation forces and recoveries represented as clustered hexagons.

In one embodiment, as shown in FIG. 15, hexagons 1502A, 1502B are grouped such that the perturbation or recovery are placed in the center 1504A, 1504B of additional hexagons responsive to the features and related quanta of the perturbation or recovery at the center of the group. Any number of features can be visually aggregated in this way. In one embodiment, hexagons for the features are arranged spatially within the hexagon associated with the perturbation or recovery to which they are associated. Once hexagons are visually aggregated in this way, as shown in FIG. 15, these clusters of hexagons can be themselves aggregated according to relationships between perturbations, perturbation features, recoveries and/or recovery features. For example, as shown in FIG. 16, a pair of quaternaries (originally depicted in FIG. 6) can be displayed as an image of perturbations 1602A, 1602B, recoveries 1606A, 1606B, perturbation forces 1604A, 1604B, and recovery forces 1608A, 1608B using clustered hexagons as depicted in FIG. 15. FIG. 16 depicts a pair of related quaternaries showing that, in one embodiment, quaternaries provide a spatial link which can be extrapolated to a greater number of quaternaries including all identified.

Figure 17:
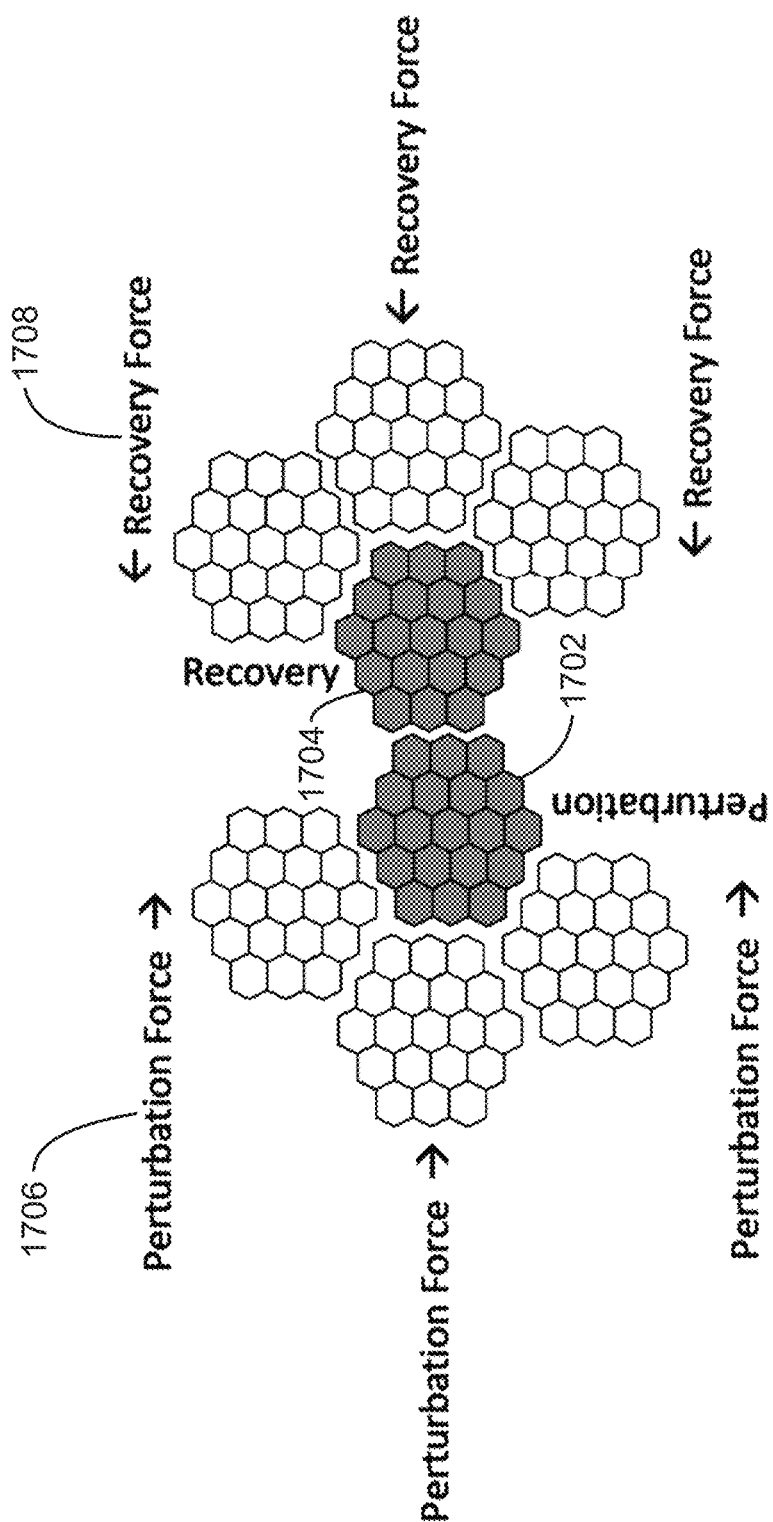
FIG. 17 depicts a perturbation/recovery pair visually decorated with the associated forces identified in which hexagon clusters for each perturbation, recovery and force are shown.

In one embodiment, as shown in FIG. 17, perturbation 1702/recovery 1704 pairs are visually decorated with the associated forces 1706 and 1708 identified. Hexagon clusters for each perturbation, recovery and force are fully expanded in the method depicted in and described by FIG. 15. In one embodiment these clusters are arranged spatially to display the direction of the forces identified.

Figure 18:
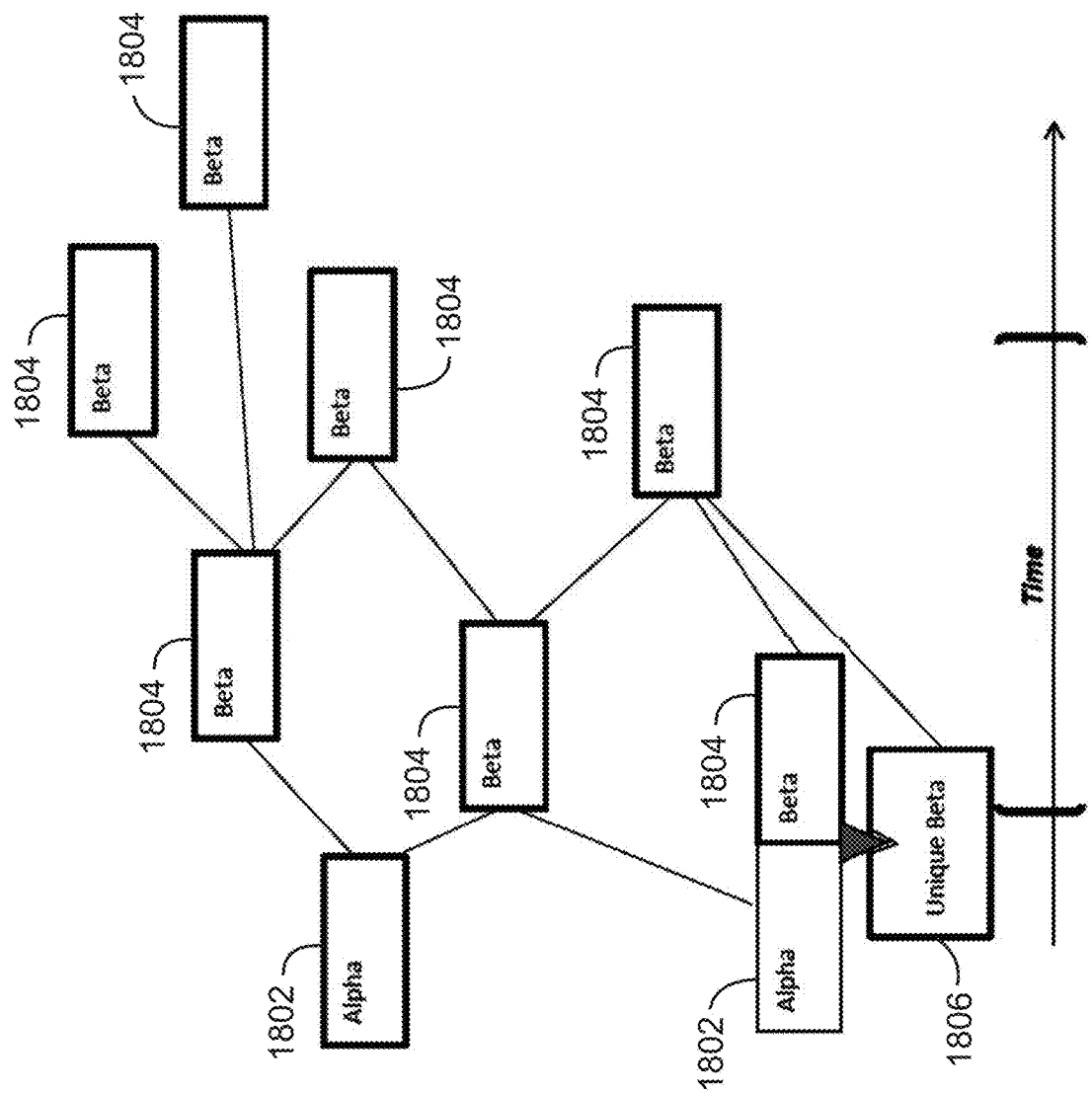
FIG. 18 depicts a schematic of a complex time dimensioned pathophysiologic cascade with relationally enabled links in which a unique binary object enables a connection to an otherwise non-connectable beta.
Figure 18:
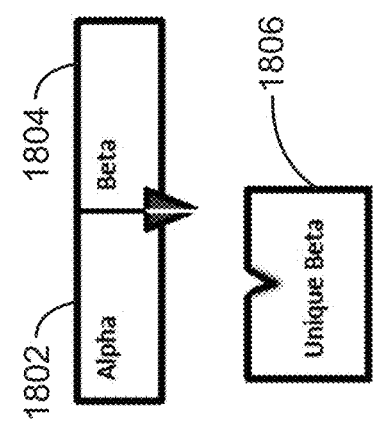

In one embodiment, a schematic of a complex time dimensioned pathophysiologic cascade with relationally enabled links is displayed as shown in FIG. 18. Using a combination of an alpha 1802 and beta 1804 the processor 200 may generate a unique binary object 1806, which enables relationally enabled connection to an otherwise non-connectable beta (which can also be another binary). Such combinations may also be defined to classify a rise or a fall to whether it represents a perturbation or recovery from a prior perturbation (which may have occurred before the data collection. For example, a fall in absolute neutrophils may be a perturbation (for example, when the neutrophils have been destroyed or sequestered in the battle against the microorganism) or a recovery (as an indication of a return of the absolute neutrophil density toward the normal range as the infection abates). If the processor 200 detects a rise in bands concomitant with the fall in absolute neutrophils it may generate a unique "decoherence binary" comprised of the rise in bands with the fall in absolute neutrophils. Upon the identification of this decoherence binary, the processor 200 classifies the fall in absolute neutrophils as a perturbation and not a recovery.

Figure 19:
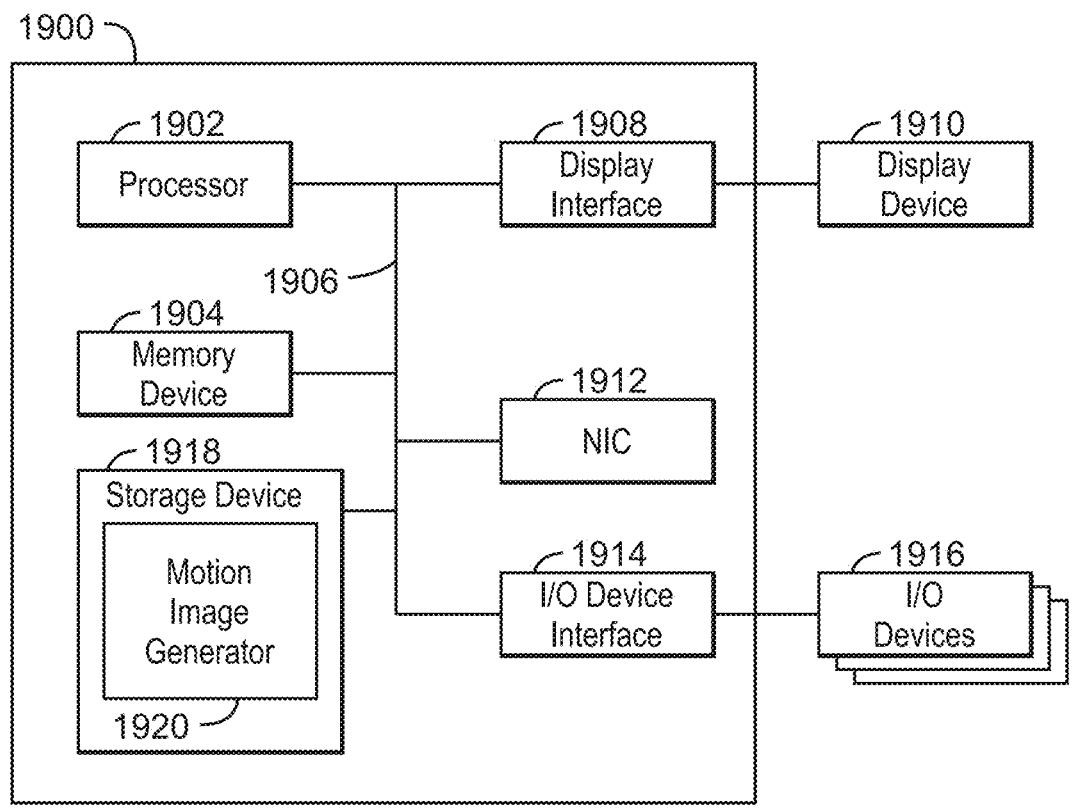
FIG. 19 is a block diagram of an example of a computing device that can generate motion images of a clinical condition.

FIG. 19 is a block diagram of an example of a computing device that can generate motion images of a clinical condition. The computing device 1900 may be, for example, a hospital monitor, mobile phone, laptop computer, desktop computer, or tablet computer, among others. The computing device 1900 may include a processor 1902 that is adapted to execute stored instructions, as well as a memory device 1904 that stores instructions that are executable by the processor 1902. The processor 1902 can be a single core processor, a multi-core processor, a computing cluster, or any number of other configurations. The memory device 1904 can include random access memory, read only memory, flash memory, or any other suitable memory systems. The instructions that are executed by the processor 1902 may be used to implement a method that can generate motion images of a clinical condition.

The processor 1902 may also be linked through the system interconnect 1906 (e.g., PCI®, PCI-Express®, HyperTransport®, NuBus, etc.) to a display interface 1908 adapted to connect the computing device 1900 to a display device 1910. The display device 1910 may include a display screen that is a built-in component of the computing device 1900. The display device 1910 may also include a computer monitor, television, or projector, among others, that is externally connected to the computing device 1900. In addition, a network interface controller (also referred to herein as a NIC) 1912 may be adapted to connect the computing device 1900 through the system interconnect 1906 to a network (not depicted). The network (not depicted) may be a cellular network, a radio network, a wide area network (WAN), a local area network (LAN), or the Internet, among others.

The processor 1902 may be connected through a system interconnect 1906 to an input/output (I/O) device interface 1914 adapted to connect the computing device 1900 to one or more I/O devices 1916. The I/O devices 1916 may include, for example, a keyboard and a pointing device, wherein the pointing device may include a touchpad or a touchscreen, among others. The I/O devices 1916 may be built-in components of the computing device 1900, or may be devices that are externally connected to the computing device 1900.

In some embodiments, the processor 1902 may also be linked through the system interconnect 1906 to a storage device 1918 that can include a hard drive, an optical drive, a USB flash drive, an array of drives, or any combinations thereof. In some embodiments, the storage device 1918 can include a motion image generator 1920. The motion image generator 1920 can receive data relating to biologic particles' densities associated with the clinical condition and define a plurality of perturbation types of the biologic particles' densities, wherein a first perturbation type comprises a rise and a second perturbation type comprises a fall. The motion image generator 1920 can also define a plurality of sets of feature types, wherein a first feature set comprises features of a rise and a second feature set comprises features of a fall and detect or determine a plurality of perturbations of the plurality of perturbation types. In some embodiments, the motion image generator 1920 can detect or determine a plurality of feature sets of the plurality of feature types, and generate a motion image of, or responsive to, the feature sets, which changes over time in response to changes in the features, the motion image being indicative of at least the severity of the clinical condition over time.

It is to be understood that the block diagram of FIG. 19 is not intended to indicate that the computing device 1900 is to include all of the components shown in FIG. 19. Rather, the computing device 1900 can include fewer or additional components not illustrated in FIG. 19 (e.g., additional memory components, embedded controllers, additional modules, additional network interfaces, etc.). Furthermore, any of the functionalities of the motion image generator 1920 may be partially, or entirely, implemented in hardware and/or in the processor 1902. For example, the functionality may be implemented with an application specific integrated circuit, logic implemented in an embedded controller, or in logic implemented in the processor 1902, among others.

Figure 20:
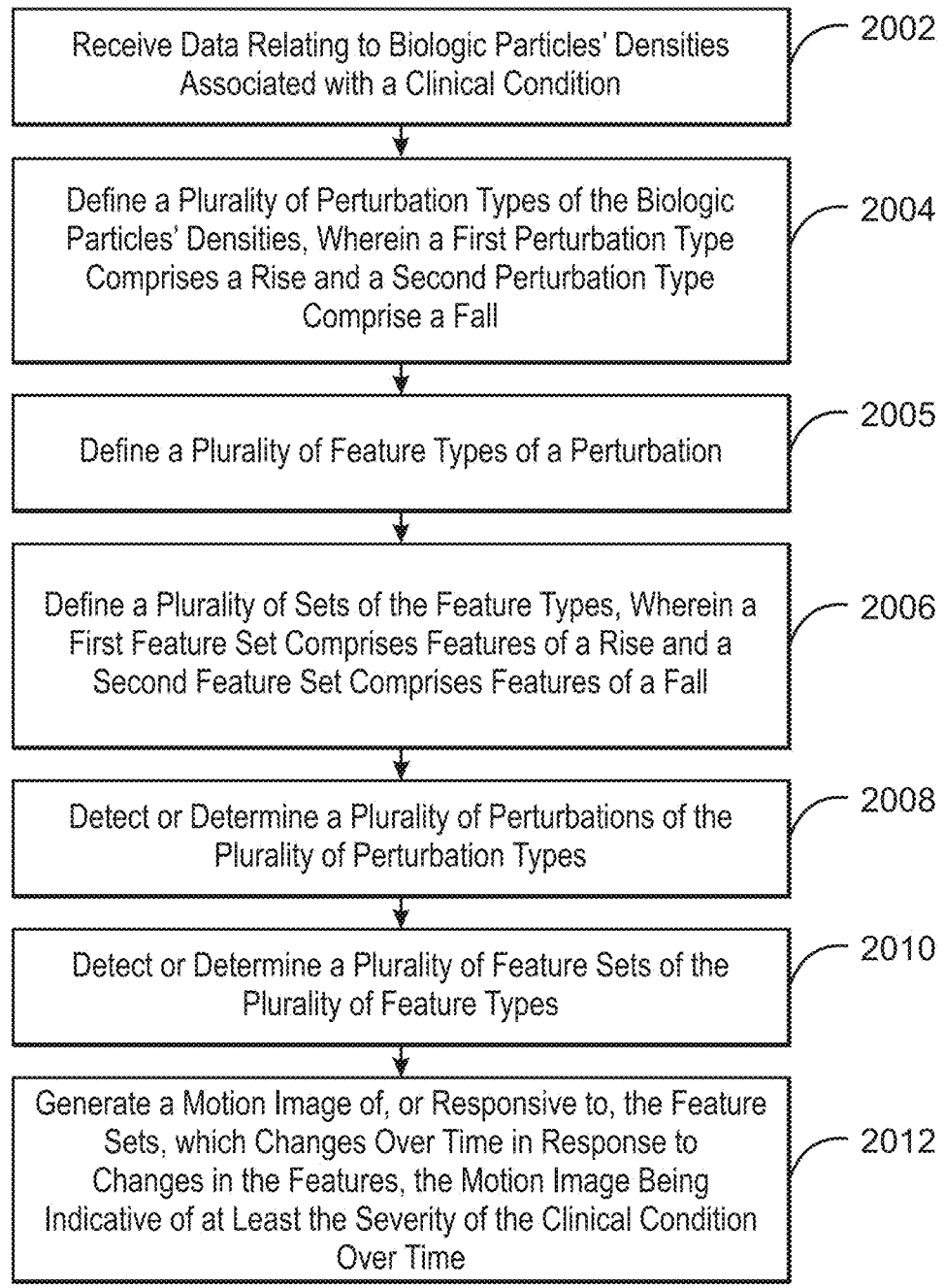
FIG. 20 is a process flow diagram of an example method for generating motion images of a clinical condition.

FIG. 20 is a process flow diagram of an example method for generating motion images of a clinical condition. The method 2000 can be implemented with a computing device, such as the computing device 1900 of FIG. 19.

At block 2002, the motion image generator 1920 can receive data relating to biologic particles' densities associated with the clinical condition. At block 2004, the motion image generator 1920 can define a plurality of perturbation types of the biologic particles' densities, wherein a first perturbation type comprises a rise and a second perturbation type comprises a fall. At block 2005, the motion image generator 1920 can define a plurality of feature types of a pertubation. At block 2006, the motion image generator 1920 can define a plurality of sets of feature types, wherein a first feature set comprises features of a rise and a second feature set comprises features of a fall. At block 2008, the motion image generator 1920 can detect or determine a plurality of perturbations of the plurality of perturbation types. At block 2010, the motion image generator 1920 can detect or determine a plurality of feature sets of the plurality of feature types. At block 2012, the motion image generator 1920 can generate a motion image of, or responsive to, the feature sets, which changes over time in response to changes in the features, the motion image being indicative of at least the severity of the clinical condition over time.

The process flow diagram of FIG. 20 is not intended to indicate that the operations of the method 2000 are to be executed in any particular order, or that all of the operations of the method 2000 are to be included in every case. Additionally, the method 2000 can include any suitable number of additional operations.

One of ordinary skill in the art will appreciate the technical effect described herein which enables generating motion images of a clinical condition. Some embodiments described herein have the effect of generating a motion image indicative of the severity of a clinical condition over time.

Conditional language used herein, such as, among others, "can," "may," "might," "could," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

While the above detailed description has shown, described, and pointed out novel features as applied to various embodiments, it will be understood that various omissions, substitutions, and changes in the form and details of the device or process illustrated may be made without departing from the spirit of the disclosure. As will be recognized, certain embodiments described herein may be embodied within a form that does not provide all of the features and benefits set forth herein, as some features may be used or practiced separately from others. The scope of some embodiments is indicated by the appended claims rather than by the foregoing description. All changes which come within the meaning and range of equivalency of the claims are to be embraced within their scope.

The term laboratory measurements, values, and densities may comprise calculated values or may comprise the actual measurements and values indicative of particle densities, particle characteristics, or other physical components or characteristics in, or of, the sample under test such as the blood. The analog or digital outputs of automated measurements derived from automated systems (such as automated hematology or chemistry instrumentation) may be received and converted to time series when multiple sequential samples are available. Such measurements may be derived from florescence, impedance volume, for example with direct current, radiofrequency conductivity with impedance aperture, laser light scattering, photon spectral absorption, antibody probes, PCR amplification, chemical reactions, or many other methods as are well known in the art. In many situations such measurements actually comprise the densities or characteristics of the biologic particles but have not yet been formally converted into the formal density or characteristic values which healthcare workers are accustomed to seeing, for example in an automated complete blood count. In one embodiment these signal may be used directly by the processor 200 to generate, perturbations, forces, and recoveries and features of perturbations, forces, and recoveries before converting them into the formal density or characteristic values which healthcare workers are accustomed to seeing.

With this approach, time series or timed groupings of these measurements or values may be generated. Perturbations, features of perturbations, forces, features of forces, and recoveries and features of recoveries may be identified in these signals and/or converted into objects. These may be used to derive image components, images, sequenced of images and/or mapped and presented to an image recognition system. These may be combined with the calculated or estimated density values to create a more comprehensive map. Such measurements render rawer outputs which may be plotted directly and although some represent density equivalents others contain features or relational patterns over time which may have been lost in the quantification processes associated with conversion of these analog or digital signals into to the formal density or characteristic values which healthcare workers are accustomed to seeing.

One visualization format is similar to a color radar weather map of the type commonly viewed by most Americans on the evening news during common rain, snow, or thunderstorms, as well as during hurricanes and tornadoes. This provides a dynamic visualization of a complex sepsis cascade, for example, as a "patient storm" with the visualized patient storm dynamically spreading across the geographic space which represents the various systems of the human body. The term patient storm refers to a patient pathophysiologic condition, failure, or complication, such as sepsis which characteristically progresses in a progressive and expansive manner potentially involving a progressive number of systems. The storm metaphor provides the cues that can greatly shorten the learning curve for the healthcare professional to allow them to readily see and perceive the characteristics of the dynamic nature of an expanding cascade of sepsis which has proven otherwise very difficult for them to learn and understand. In one embodiment these workers see the dynamic and relational patterns of complexity of sepsis in evolution as they would for a major storm spreading across North America. In one embodiment, the metaphorically presented patient storms, like weather storms, have patient storm components like patient storm cells, patient storm fronts, patient storm origins, patient storm expansions, patient storm movement, and patient storm contraction and/or recovery. Multiple patient storms of one or more types may also be visually presented in relation to each other. According to one embodiment, computational transparency is provided either automatically or upon a healthcare worker gesture (as with auditory, textual, touch, natural interface actions or mouse over to name a few) so that the healthcare worker can look inside a patient storm front or a patient storm cell for example to see which relational pathophysiologic perturbations which were identified or detected by the processor to generate patient storm components.

According to one embodiment patient storm cells may be derived from alpha events and the beta events of the image binaries, or the image binaries themselves. In the alternative, or in addition, the patient storm cell may be derived from the beta events, alpha events, sigma events and tau events of the perturbation and recovery force binaries or of the force binaries, coupled binaries, quaternaries, and/or cascades themselves. In this way the display may generate dynamic motion images of the relational patient storm cell as well as dynamic motion images of the relational forces which induced the patient storm cells.

Figure 21:
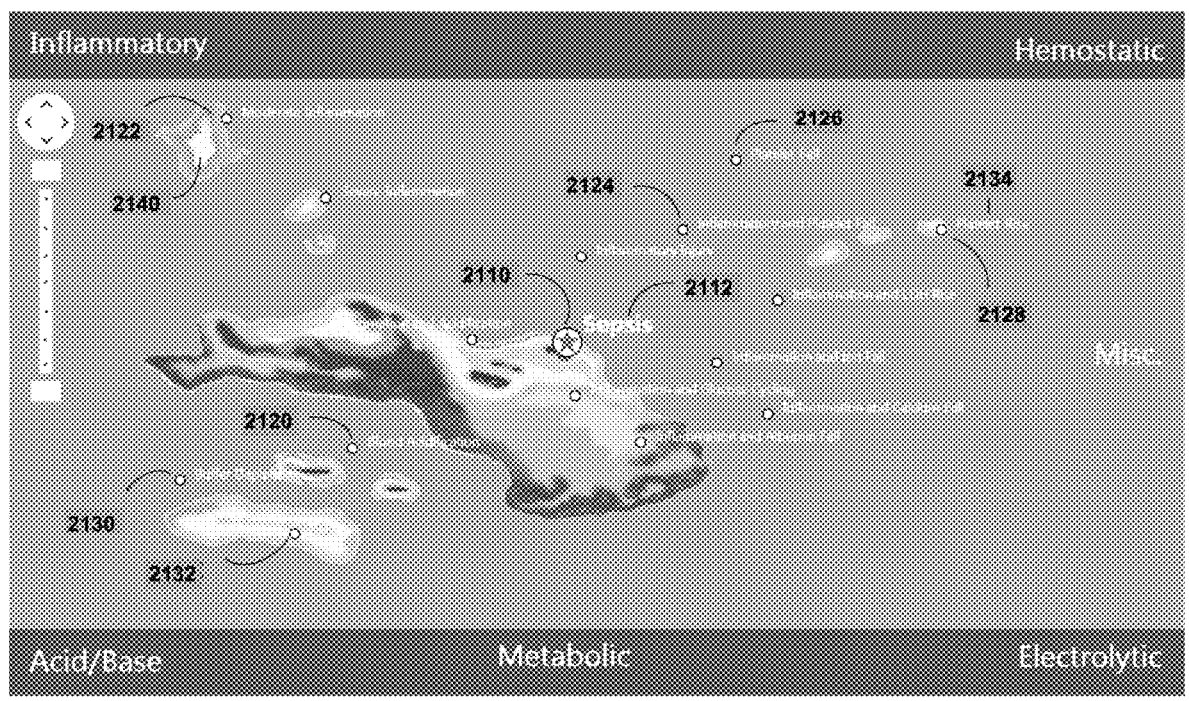
FIG. 21 is an illustration of an exemplary Condition-Centric map for Sepsis in accordance with the present disclosure.

In the present embodiment, FIG. 21 shows an example of a Patient storm Tracker and Visualization Processor (PSTVP) visualization which utilizes the weather metaphor to present the state of a patient specifically associated with a patient condition—in this case sepsis. FIG. 21 is a condition-centric map for sepsis.

The condition-centric map is made up of three layers—the background, the weather and overlays. The background is static across patients and provides a common "geography" over which perturbation flows. The second and third layers (weather and overlays) are both patient and time specific. Animation shows the change in the top two layers over time showing perturbation data emerging, moving, growing, changing color and being labeled with iconic overlays creating a moving picture of the dynamic evolution of the condition in time.

The background of the condition-centric map is condition-specific. In the present embodiment a map is created for each condition for which the PSTVP system is monitoring. In an alternative embodiment, a single map is used with multiple conditions. In the present embodiment, the central element, a circle with a star 2110, is labeled with the condition 2112 and represents the specific condition for which this map has been constructed. This iconic representation taps into the common metaphor of a capital city 2110. In an embodiment, the capital city is in the right-most position with the map extending out in a conical fashion from left to right. The central element 2110 may be responsive to the detection of the patterns. For example the central element 2110 may be initially missing or almost invisible, and then become visible or more visible or otherwise highlighted when sufficient pattern components have been identified to warrant display of the central element 2110. In one embodiment, the background is further made up of individual circles 2120 representing sub-conditions within the central condition 2110. For example, as shown in FIG. 21, Blood Acidification 2120 is shown as a sub-condition within the Acid/Base clinical space. These circles tap into the metaphor of cities within a weather map. Sub-conditions may, for example, be occurrences, relational occurrences, trends, relational trends, threshold violations, relational threshold violations, and a wide range of combinations of these as for example described in the aforementioned patient applications. In an example during a sepsis patient storm moderate inflammation 2122 may be combined with a fall in bicarbonate to form one sub-condition and with a fall in platelets to form another sub-condition 2124 (each which may be designated on the map as a circle or city). Cities, representing sub-conditions, are placed with respect to the clinical space areas. Further, placement within the clinical space area may also be chosen with respect to the relationship to other clinical spaces and/or sub-conditions.

In one embodiment, sub-conditions are represented by pattern scripts written in PDL as for example described in the aforementioned patient applications. A sub-condition may be a single pattern (e.g. Platelet Fall) or a pattern made up of several other patterns (e.g. Blood Acidification). A city may be related to another city within the map. For example, Blood Acidification 2120 is a classification that can be either Buffer Depletion 2130 or Acidosis 2132. This opportunity for relating cities creates an integrated relational network of patterns. In one embodiment, the relationship between cities is shown on the background. In one embodiment, the visibility of these relationships is toggled in response to a user gesture.

Cities, representing sub-conditions, are labeled 2134 (as seen in FIG. 21) and are part of the background of the map and therefore are fixed in position during presentation to the healthcare worker. The initial placement of the cities can be determined by several factors including statistical correlation to the condition, disease stage, disease progression, disease severity, and by relationship to region and/or other cities to name a few. However the value may be any of a number of correlativity metrics relating to probability assessment. In at least one discussion specificity is shown to provide an example of one correlativity metric.

The PSTVP provides a visual map editor with which an expert can construct a map.

The background as a whole—the central element 2110 and the cities 2126 are displayed along with their labels to provide a fixed geography over which perturbation flows. Familiarity with these positions on the map helps to provide a context which can be assimilated as a whole providing rapid cognition.

The next layer of for the condition-centric map is the weather layer. This layer displays perturbation flowing over the background to tap into the metaphor of weather flowing over a familiar geography. In the present embodiment, each city has a script associated with it. Within that script are one or more sub-scripts or statements representing possible occurrences within the sub-condition. From these scripts, both the scripts for the city, and all of the associated sub-scripts an associated patient storm cell is derived. For example, the city "Moderate Inflammation" 2122 (shown in FIG. 21) is defined with the following PDL:

identify ModInflammatoryIndicator as RiseInWBC or RiseInNeutrophils or LowWBC or FallInNeutrophils or HighWBC or HighNeutrophils or LowNeutrophils;

The city "Moderate Inflammation" 2122 is associated with this classification "ModInflammatoryIndicator." This means that ModInflammatoryIndicator has seven sub-scripts each containing a different pattern which the PSP system is monitoring in real time. If any occurrences are identified within those sub-scripts then perturbation will be presented on the map as a patient storm cell 2140.

The dynamic transition of infection to inflammatory augmentation to sepsis is very a complex dynamic process. To engage complexity one embodiment provides a multidimensional severity and progression indicator, called a patient storm cell 2140. The patient storm cell can be represented as a collection of colored hexagons placed within the weather layer of the weather map. In an alternative embodiment, other visual elements are used including grey-scale hexagons, textured hexagons, pixels, other fixed or variable geographic shapes, fractals, and/or circles to name a few. In one embodiment, a series of transformations are executed including geometric, texture and finishing transformations to name a few. The collection of hexagons is determined from a metric profile of the associated city. In the current embodiment, severity is used as the metric from which the profile is created. In an alternative embodiment, other metrics are used including occurrence count, statistical measures, and relational metrics to name a few. This may be used to generate an alternative weather map wherein the relative probability of a condition is substituted for severity (as described herein) to generate the weather movement expansion and severity. Similarly expense may be used to generate the weather with the relative expense associated with each cascade portion and cell is substituted for severity (as described herein) to generate the weather movement expansion and severity. The user may toggle between the severity map and the probability map and the expense map, or the maps be overlaid, for example as transparencies, or otherwise integrated with different colors, shapes, or icons, and shown together.

In the present embodiment severity is defined in terms of severity modes.

The severity modes comprise the severity of each of the different properties of each occurrence or relational occurrence as well as relational modes in which properties and/or occurrences are considered in context of other properties and/or occurrences. For example an occurrence may be a Rise in White Blood Cells (WBC rise), properties of the WBC rise may, for example, comprise a WBC rise slope, WBC rise magnitude, WBC rise percent change, and WBC rise duration, WBC rise minimum value, WBC rise maximum value, WBC rise in relation to the normal range, to name a few. Each of these properties may comprise a severity mode for the occurrence WBC rise.

An occurrence may have a high severity by one severity mode (one occurrence property) and a low severity by another severity mode (one occurrence property). This embodiment provides the ability to define severity variation with a high level of relational granularity across many severity modes applicable to each occurrence and therefore provides an output which more closely matches the true pathophysiologic complexity. This provides the ability to detect the subtle, insidious, and highly variable relational foci of progression and/or relational foci of progression which characterize the transition from simple infection to early sepsis, and then from early sepsis to more severe states. In an example a single severity mode, such as a WBC rise maximum value of 11 may be of low severity but if the rise was rapid so that the WBC slope was high (for example 0.8/hr), or if it was of high magnitude (for example 6.4), then each of these severity modes will trigger a higher severity in their pixels of the visualization to warn that, while the WBC is still normal, dynamic changes are in progress. Furthermore the use of a wide range of severity modes allows more robust protocolization. In the above example, the processor may not be programmed to take any action in response to a WBC of 11 but based on the combination of a high slope and high magnitude severity may be programmed to order a repeat WBC in 4 hours to determine if the WBC rise is continuing. As noted previously this is one aspect of the present embodiment provided to solve the problem of over-simplification of the complexity which is causing so many late detections and deaths. In one example a first gradation of severity used for each severity mode is defined as an integer between 0 and 15. The profile is an array of cells 860 made up of fifteen slots representing the count of severity values matching the integer values. For example, a profile {0,3,0,6,0,0,0,0,0,0, 0,0,0,0,0} indicates 3 instances of severity value 2 and 6 instances of severity value 4 and no other severity instances. In the present embodiment, for each patient each city has a severity profile for a given point in time within the patient stay. All of the scripts associated with a city feed into the severity profile, as shown in FIG. 21. For example, for the Moderate Inflammation city 2122 described above there are 7 patterns being monitored and each of those patterns may identify one or more instances of an occurrence of that pattern. For example, a patient may exhibit two instances of FallInWBC, an instance of LowWBC, and an instance of LowNeutrophils. In this case there are 3 patterns identified and 4 instances. For each of the instances the severity of the instance can be derived. For example, the two instances of FallInWBC may be a severity 2 instance followed by a severity 6 instance while the LowWBC may be a severity 4 and the LowNeutrophils may be a severity 6. In this case, given only the severity of the instances of the sub-scripts we would derive the profile {0,1,0,1,0,2,0,0,0,0,0,0,0,0,0}. Further, individual properties of the instances can further contribute to the severity profile. For example, the slope of the fall of the instances of the FallInWBC may be considered severity 7 and 3 respectively whereas the duration of the LowWBC may be considered severity 3 and the duration of the LowNeutrophils may be considered severity 4. In this case the severity profile would now be {0,1,2,2,0,2,1,0,0,0, 0,0,0,0,0}.

Example Embodiments

In some embodiments, a patient monitoring system for generating motion images of a clinical condition comprises a processor programmed to receive data relating to biologic particles' densities associated with the clinical condition and define a plurality of perturbation types of the biologic particles' densities, wherein a first perturbation type comprises a rise and a second perturbation type comprises a fall. The processor can also be programmed to define a plurality of feature types of a pertubation and define a plurality of sets of the feature types, wherein a first feature set comprises features of a rise and a second feature set comprises features of a fall and detect or determine a plurality of perturbations of the plurality of perturbation types. In some embodiments, the processor can be programmed to detect or determine a plurality of feature sets of the plurality of feature types, and generate a motion image of, or responsive to, the feature sets, which changes over time in response to changes in the features, the motion image being indicative of at least the severity of the clinical condition over time. In some examples, the processor is programmed to generate cells responsive to the plurality of perturbations and to generate an image comprising the cells.

In some embodiments, a single perturbation is mapped onto a single cell and said single cell is responsive to changes of said single perturbation. In one example, the first feature set comprises at least two feature types, and wherein a feature type comprises at least one of: a beginning value, an end value, a peak value, a slope, a duration, a momentum, a percent change, or a magnitude. In some examples, the first feature set comprises at least three feature types, and wherein a feature type comprises at least one of: a beginning value, an end value, a peak value, a slope, a duration, a momentum, a percent change, or a magnitude. In one embodiment, a second feature set comprises at least three feature types, and wherein a feature type comprises at least one of: a beginning value, an end value, a nadir value, a slope, a duration, a momentum, a percent change, or a magnitude. Additionally, at least a portion of cells can include a set of organelles and a single feature set of said single perturbation is mapped onto a single set of organelles and each said set of organelles is responsive to changes of said single feature set.

In some embodiments, an image is generated on a display, said display comprising a map of a plurality of clinical regions, and a plurality of cells that are mapped onto the plurality of clinical regions. In some examples, the cells comprise a cell area within the cell and a set of features that are mapped within the cell area. In one embodiment, cells can comprise a cell area within the cell and a set of organelles are mapped within the cell area, said feature set being mapped to the set of organelles. In some examples, a plurality of different cells are responsive to a corresponding plurality of different perturbations. In other examples, a plurality of different organelles are responsive to a corresponding plurality of different features. In some embodiments, each of a plurality of different organelles is mapped to said single cell.

In some embodiments, a map displays a plurality of clinical regions, and the image is displayed on the map, the image being responsive to a plurality of perturbations associated with said regions, and a plurality of features associated with said perturbations. In one example, a system comprises a visualization that comprises a map and a plurality of clinical regions within said map, and a motion image associated with the map, the motion image being responsive to a plurality of sets of features of perturbations. In some examples, each of a plurality of different cells is mapped to each of a corresponding plurality of different clinical regions and each of a plurality of different sets of features is mapped onto a corresponding plurality of different cells. In some embodiments, a visualization comprises a map and a plurality of clinical regions within said map, and a motion image associated with the map, the motion image being comprised of a plurality of cells, and wherein a cell comprises a set of organelles, and said set of organelles is responsive to a set of features of a perturbation.

In one embodiment, a set of organelles changes in color in response to changes of the features of a perturbation. In some examples, a processor is programmed to generate discrete cells, wherein each discrete cell is responsive to a specific perturbation. In one embodiment, an image is a time-lapsable motion image. In some examples, the motion image changes over time in response to detection of changes of the features of the perturbations. In one embodiment, the motion image changes over time in response to detection of changes of the perturbations. Additionally, in some examples, cells can be positioned in predetermined locations on a map. In one example, a motion image changes over time in response to at least one of a change in a size, a shape, a position, or a color of the cells. In some examples, an entire motion image of a clinical condition is provided in a single time-lapsable visualization.

In some embodiments, cells have a fixed location in the map over time. In one example, at least a portion of the cells contain organelles and the organelles are responsive to changes of features of the perturbation which are mapped to the specific cell.

In some embodiments, a patient monitoring system for generating motion images of at least one clinical condition comprises a processor programmed to receive data related to biologic particle densities and detect a plurality of perturbations of the biologic particle densities associated with the clinical condition. The processor can also be programmed to detect or determine features of the perturbations and generate cells responsive to the perturbations. Furthermore, the processor can be programmed to generate organelles within the cells responsive to said features, and generate at least one time-lapsable image comprising the cells, the image changing over time in response to at least one of, detection of changes in the features, detection of new features, or detection of new perturbations. In some examples, the processor is programmed to convert at least a portion of the features into quanta defined, at least in part by the condition. In one embodiment, a specific perturbation is mapped to a specific cell. In some examples, a specific feature of said specific perturbation is mapped to a specific organelle within the said specific cell. Each organelle of each cell can be responsive to a different feature of the same perturbation which is mapped on the cell. Additionally, in some examples, different organelles are responsive to different features of the same perturbation. Furthermore, at least a portion of the cells can comprise a plurality of organelles that are each responsive to a different feature of the perturbation that is mapped to the cell.

In some embodiments, a patient monitoring system for generating motion images of at least one clinical condition comprises a processor programmed to receive data relating to biologic particle densities and detect a plurality of perturbations of the biologic particle densities associated with the clinical condition. The processor can also be programmed to detect features of the perturbations and generate cells of images responsive to the perturbations. Furthermore, the processor can be programmed to generate regions within the cells responsive to said features, and map the cells onto a preformatted map. In addition, the processor can be programmed to generate an image comprising cells on the map. In some examples, the map is preformatted into regions, at least a portion of the regions corresponding to human physiological systems or organs. In one embodiment, at least a portion of the cells are preformatted to provide a plurality of regions inside the cells. The regions can comprise organelles having a fixed location in the cell.

In some embodiments, a first feature of a perturbation is mapped to a first organelle within a first cell and at least a second feature is mapped to a second organelle within said first cell. In some examples, a first organelle is responsive to changes of said first feature and said at least second organelle is responsive to changes of said second feature. In one example, a first organelle changes in color in response to changes of said first feature and said second organelle changes in color in response to changes of said second feature. Additionally, a processor can be programmed to convert at least a portion of the features into quanta, the quanta being indicative of the severity of the feature, the severity of the features being defined, at least in part, by the condition, so that at least a portion of the quanta are indicative of condition specific severity of the features.

In some embodiments, a patient monitoring system for generating motion images of at least one clinical condition comprises a processor programmed to receive data relating to biologic particles densities and detect perturbations of the biologic particle densities. The processor can also be programmed to detect or determine the features of at least a portion of the perturbations and define the severity of at least a portion of the features, the severity being determined at least in part by the condition. In addition, the processor can be programmed to generate a first image responsive to severities of the features and detect at least one force which may have caused or induced the perturbations. Furthermore, the processor can be programmed to generate a second image responsive to the force, and generate a motion image comprising at least the first and second image. In some examples, the processor is programmed to detect a set of features of each perturbation. Additionally, the processor can be programmed to generate a set of organelles associated with the first image, the set of organelles being responsive to a set of features of the perturbation. Furthermore, the processor can be programmed to detect or determine features of the force. In some examples, the processor is programmed to generate a set of organelles associated with the second image, the organelles being responsive to a set of features of the force.

In some embodiments, a patient monitoring system for generating dynamic visualizations of at least one clinical condition comprises a processor programmed to receive data related to biologic particles densities. The processor can also be programmed to detect a plurality of perturbations of the densities associated with the clinical condition and detect or determine features of the perturbations. In some embodiments, the processor can be programmed to convert at least the features into quanta, at least a portion of the quanta being indicative of the severity of the features and wherein said quanta are defined at least in part by the condition, so that the at least a portion of the severity of the quanta are condition specific. Furthermore, the processor can be programmed to generate time dimensional image components responsive to the quanta over time, and generate a motion image comprised of the time dimensional image components. In some examples, the image components comprise one or more colored pixels.

The Appendix includes one embodiment of a domain specific language script relating to detection and imaging of inflammation, acidosis, a parenteral antibiotic indicating disorder (PAID), pathophysiologic decoherence or divergence (PD), physiologic coherence (or convergence) CONV, systemic inflammatory response syndrome (SIRS) (which is more advanced than the conventional SIRS definition) and varying degrees of sepsis severity, and other conditions.

APPENDIX TO SPECIFICATION define stream Albumin as "Albumin"

profile severity when low value 3.7, 3.6, 3.5, 3.4, 3.2, 3.0, 2.8, 2.6, 2.4, 2.2, 2.1, 2.0, 1.9, 1.8, 1.7 when fall min 3.7, 3.6, 3.5, 3.4, 3.2, 3.0, 2.8, 2.6, 2.4, 2.2, 2.1, 2.0, 1.9, 1.8, 1.7 magnitude 0.4, 0.5, 0.6, 0.7, 0.8, 0.9, 1.0, 1.2, 1.4, 1.6, 1.8, 2, 2.2, 2.4, 2.6 qualify fall on magnitude locate in metabolic;

define stream AnionGap as "Anion Gap"

profile severity when high value 12, 12.5, 13, 13.5, 14, 14.5, 15, 15.5, 16, 17, 18, 19, 20, 21, 22 when rise max 12, 12.5, 13, 13.5, 14, 14.5, 15, 15.5, 16, 17, 18, 19, 20, 21, 22 magnitude 1, 2, 3, 3.5, 4, 4.5, 5, 5.5, 6, 6.5, 7, 7.5, 8, 8.5, 9 qualify rise on magnitude locate in acidbase;

define stream Bands as "Bands"

profile severity when high value start with 4 increase by 1 when rise max start with 4 increase by 1 magnitude start with 3 increase by 1 qualify rise on magnitude locate in inflammatory;

define stream BandsAbs as "Bands Abs"

profile severity when high value 1.2, 1.4, 1.6, 1.7, 1.8, 1.9, 2.0, 2.2, 2.4, 2.6, 2.8, 3.0, 3.2, 3.6, 4.0 when rise max 1.2, 1.4, 1.6, 1.7, 1.8, 1.9, 2.0, 2.2, 2.4, 2.6, 2.8, 3.0, 3.2, 3.6, 4.0 magnitude 0.1, 0.15, 0.18, 0.2, 0.25, 0.3, 0.35, 0.4, 0.5, 0.6, 0.8, 1.0, 1.5, 2.0, 2.5 qualify rise on magnitude locate in inflammatory;

define stream BaseDeficit as "Arterial Base Deficit"

profile severity when high value start with 1 increase by 0.3 when rise max start with 0.3 increase by 0.3 slopeindays start with 0.3 increase by 0.2 magnitude start with 0.3 increase by 0.2 percentchange start with 10 increase by 5 when fall slopeindays start with -0.3 decrease by 0.2 qualify rise on magnitude locate in acidbase;

define stream Bicarb as "Bicarbonate", "HCO3, Arterial", "TCO2, Arterial", "Carbon Dioxide"

profile severity when low value 24, 23.5, 23.2, 23, 22, 21, 20, 19, 18, 17, 16, 15, 14, 13, 12 when fall min 24, 23.5, 23.2, 23, 22, 21, 20, 19, 18, 17, 16, 15, 14, 13, 12 magnitude start with 1.5 increase by 0.5 qualify fall on magnitude locate in acidbase;

define stream BPSystolic as "BP Systolic", "ABPSys"

profile severity when low value start with 100 decrease by 5 when fall min start with 100 decrease by 5 magnitude start with 20 increase by 2 qualify fall on magnitude locate in cardiac;

define stream BPMean as "BP Mean", "ABPMean"

profile severity when low value start with 70 decrease by 2 when fall min start with 70 decrease by 2 magnitude start with 10 increase by 2 qualify fall on magnitude locate in cardiac;

define stream BUN as "BUN"

profile severity when high value 23, 24, 25, 26, 27, 28, 30, 32, 34, 36, 38, 40, 42, 44, 46 when rise slopeindays 1, 2, 3, 4, 5, 6, 7, 8, 9, 10, 11, 12, 13, 14, 15 magnitude 2, 4, 6, 8, 10, 12, 14, 16, 18, 20, 22, 24, 26, 28, 30 percentchange 2, 3, 4, 6, 8, 16, 20, 24, 28, 32, 36, 40, 44, 48, 52 when low value 1|10, 2|9, 3|8, 4|7, 5|6, 6|5, 7|4, 8|3, 9|2, 10|1, 11|0 when fall slopeindays -1, -2, -3, -4, -5, -6, -7, -8, -9, -10, -11, -12, -13, -14, -15 magnitude 2, 4, 6, 8, 10, 12, 14, 16, 18, 20, 22, 24, 26, 28, 30 percentchange 5, 8, 10, 14, 18, 22, 26, 30, 34, 38, 42, 46, 50, 54, 58 qualify rise on magnitude fall on magnitude locate in renal;

define stream Calcium as "Calcium"

profile severity when low value 8.6, 8.4, 8.2, 8, 7.8, 7.6, 7.4, 7.2, 7, 6.8, 6.4, 6, 5.5, 5, 4.5 when fall min 8.6, 8.4, 8.2, 8, 7.8, 7.6, 7.4, 7.2, 7, 6.8, 6.4, 6, 5.5, 5, 4.5 magnitude 0.4, 0.5, 0.6, 0.7, 0.8, 0.9, 1.0, 1.2, 1.4, 1.6, 1.8, 2.0, 2.2, 2.4, 2.6 qualify fall on magnitude locate in electrolytic;

define stream Chloride as "Chloride"

profile severity when high value 106, 107, 108, 109, 110, 111, 112, 113, 114, 115, 116, 117, 118, 119, 120 when rise slopeindays 1, 1.5, 2, 3, 3.5, 4, 5, 5.5, 6, 6.5, 7, 7.5, 8, 8.5, 9 magnitude 1, 2, 3, 4, 5, 6, 7, 8, 9, 10, 11, 12, 13, 14, 15 percentchange 10, 11, 12, 13, 14, 15, 16, 17, 18, 19, 20, 21, 22, 23, 24 when low value 100, 99, 98, 97, 96, 95, 94, 93, 92, 91, 90, 89, 88, 87, 86 when fall slopeindays -1, -1.5, -2, -3, -3.5, -4, -5, -5.5, -6, -6.5, -7, -7.5, -8, -8.5, -9 magnitude 1, 2, 3, 4, 5, 6, 7, 8, 9, 10, 11, 12, 13, 14, 15 percentchange 10, 11, 12, 13, 14, 15, 16, 17, 18, 19, 20, 21, 22, 23, 24 qualify rise on magnitude fall on magnitude locate in electrolytic;

define stream Creatinine as "Creatinine"

profile severity when high value 1, 1.05, 1.1, 1.15, 1.2, 1.25, 1.3, 1.35, 1.4, 1.45, 1.5, 1.55, 1.6, 1.7, 1.8 when rise slopeindays 0.01, 0.02, 0.03, 0.06, 0.08, 0.1, 0.12, 0.14, 0.16, 0.2, 0.25, 0.3, 0.4, 0.5, 0.6 magnitude 0.02, 0.04, 0.06, 0.1, 0.15, 0.2, 0.3, 0.35, 0.4, 0.45, 0.5, 0.55, 0.6, 0.7, 0.8 percentchange 2, 3, 4, 5, 6, 8, 10, 12, 14, 16, 20, 24, 28, 32, 36 when low value 0.6, 0.5, 0.4, 0.38, 0.36, 0.34, 0.32, 0.31, 0.3, 0.28, 0.26, 0.24, 0.22, 0.20, 0.18 when fall slopeindays -0.01, -0.02, -0.03, -0.06, -0.08, -0.1, -0.12, -0.14, -0.16, -0.2, -0.25, -0.3, -0.4, -0.5, -0.6 magnitude 0.02, 0.04, 0.06, 0.1, 0.15, 0.2, 0.3, 0.35, 0.4, 0.45, 0.5, 0.55, 0.6, 0.7, 0.8 percentchange 2, 3, 4, 5, 6, 8, 10, 12, 14, 16, 20, 24, 28, 32, 36 qualify rise on magnitude and percentchange fall on magnitude and percentchange locate in renal;

define stream eGFR as "eGFR"

profile severity when low value 7|59, 8|56, 9|52, 10|48, 11|44, 12|40, 13|34, 14|30, 15|26 when fall slopeindays -1, -2, -3, -4, -5, -6, -7, -8, -9, -10, -11, -12, -13, -14, -15 magnitude 1, 2, 3, 4, 5, 6, 7, 8, 9, 10, 11, 12, 13, 14, 15 percentchange 2, 4, 6, 8, 10, 12, 14, 16, 18, 20, 22, 24, 26, 28, 30 qualify fall on magnitude locate in renal;

define stream Fibrinogen as "Fibrinogen"

profile severity when low value start with 200 decrease by 7 when fall min start with 40 decrease by 3 slopeindays start with -20 decrease by 3 magnitude start with 40 increase by 3 percentchange start with 7 increase by 1 when rise slopeindays start with 20 increase by 3 qualify fall on magnitude locate in haemostatic;

define stream FIO2 as "FIO2"

profile severity when high value start with 24 increase by 6 when rise slopeindays start with 4 increase by 2 magnitude start with 4 increase by 2 percentchange start with 20 increase by 5 when fall slopeindays start with -4 decrease by 2 qualify rise on magnitude locate in respiratory;

define stream GlucoseAny as "Glucose", "Fingerstick Glucose"

profile severity when high value start with 200 increase by 20 when rise max start with 50 increase by 10 slopeindays start with 40 increase by 10 magnitude start with 50 increase by 10 percentchange start with 205 increase by 2 when low value start with 55 decrease by 2 when fall slopeindays start with -40 decrease by 10 qualify rise on magnitude locate in metabolic;

define stream Hematocrit as "Hematocrit"

profile severity when high value 43, 44, 45, 45.4, 45.8, 46.2, 46.6, 47, 47.4, 47.8, 48.2, 48.6, 49, 49.5, 50 when rise slopeindays 0.1, 0.2, 0.3, 0.4, 0.5, 0.6, 0.7, 0.8, 0.9, 1.0, 1.2, 1.4, 1.6, 1.8, 2.0 magnitude 0.2, 0.4, 0.6, 0.8, 1.0, 1.2, 1.4, 1.6, 1.8, 2.0, 2.4, 2.8, 3.2, 3.6, 4.0 percentchange 0.5, 0.75, 1.0, 1.6, 2.0, 2.4, 2.8, 3.2, 3.6, 4.0, 4.8, 5.6, 6.4, 7.2, 8.0 when low value 38, 37, 36, 35.5, 35, 34.5, 34, 33.5, 33, 32.5, 32, 31.5, 31, 30.5, 30 when fall slopeindays -0.1, -0.2, -0.3, -0.4, -0.5, -0.6, -0.7, -0.8, -0.9, -1.0, -1.2, -1.4, -1.6, -1.8, -2.0 magnitude 0.2, 0.4, 0.6, 0.8, 1.0, 1.2, 1.4, 1.6, 1.8, 2.0, 2.4, 2.8, 3.2, 3.6, 4.0 percentchange 0.5, 0.75, 1.0, 1.6, 2.0, 2.4, 2.8, 3.2, 3.6, 4.0, 4.8, 5.6, 6.4, 7.2, 8.0 qualify rise on magnitude fall on magnitude locate in Hematologic;

define stream HemoglobinAny as "Hemoglobin", "Arterial Hemoglobin", "Hgb"

profile severity when low value start with 11 decrease by 0.5 when fall min start with 0.5 decrease by 0.02 slopeindays start with -0.5 decrease by 0.05 magnitude start with 0.5 increase by 0.2 percentchange start with 8 increase by 1 when rise slopeindays start with 0.5 increase by 0.05 qualify fall on magnitude locate in hematologic;

define stream IonCalcium as "Ionized Calcium"

profile severity when low value 4.7, 4.6, 4.5, 4.4, 4.3, 4.2, 4.1, 4.0, 3.9, 3.8, 3.6, 3.4, 3.2, 3.0, 2.8 when fall min 4.7, 4.6, 4.5, 4.4, 4.3, 4.2, 4.1, 4.0, 3.9, 3.8, 3.6, 3.4, 3.2, 3.0, 2.8 magnitude start with 0.4 increase by 0.2 qualify fall on magnitude locate in electrolytic;

define stream Lactate as "Lactate"

profile severity when high value 1.8, 2.0, 2.2, 2.4, 2.6, 2.8, 3, 3.5, 4, 5, 6, 7, 8, 9, 10 when rise max 1.8, 2.0, 2.2, 2.4, 2.6, 2.8, 3, 3.5, 4, 5, 6, 7, 8, 9, 10 magnitude 0.2, 0.3, 0.4, 0.5, 0.6, 0.7, 1.0, 1.5, 2.0, 2.5, 3.0, 3.5, 4.0, 4.5, 5.0 qualify rise on magnitude locate in acidbase;

define stream LDH as "LDH"

profile severity when high value 140, 150, 160, 170, 180, 200, 220, 240, 260, 280, 300, 320, 340, 360, 380 when rise slopeindays 5, 6, 7, 8, 9, 10, 20, 30, 40, 50, 60, 70, 80, 90, 100 percentchange 7, 8, 9, 10, 20, 30, 40, 50, 60, 70, 80, 90, 100, 150, 200 when low value 80, 75, 70, 65, 60, 55, 50, 45, 40, 35, 30, 25, 20, 10, 0 when fall slopeindays -4, -5, -6, -7, -8, -9, -10, -15, -20, -25, -30, -35, -40, -45, -50 percentchange 5, 6, 7, 8, 9, 10, 15, 20, 30, 40, 50, 60, 70, 80, 90 qualify rise on percentchange fall on percentchange locate in misc;

define stream Lymphocytes as "Lymphocytes"

profile severity when high value 40, 41, 42, 43, 44, 45, 46, 47, 48, 49, 50, 51, 52, 53, 54 when rise slopeindays 2, 3, 4, 5, 6, 7, 8, 9, 10, 11, 12, 13, 14, 15, 16 magnitude 4, 6, 8, 10, 12, 14, 16, 18, 20, 22, 24, 26, 28, 30, 32 percentchange 4, 6, 8, 10, 12, 14, 16, 18, 20, 22, 24, 26, 28, 30, 32 qualify rise on magnitude locate in inflammatory;

define stream LymphocytesAbs as "Lymphocytes Abs"

profile severity when high value 3.8, 3.9, 4.0, 4.2, 4.4, 4.8, 5.5, 6, 6.5, 7, 7.5, 8, 9, 10, 11 when rise slopeindays 0.025, 0.05, 0.1, 0.15, 0.2, 0.25, 0.3, 0.4, 0.6, 0.8, 1.0, 1.2, 1.4, 1.6, 1.8 percentchange 7, 8, 9, 10, 20, 30, 40, 50, 60, 70, 80, 90, 100, 150, 200 when low value 1.1, 1.0, 0.9, 0.8, 0.75, 0.7, 0.65, 0.6, 0.55, 0.5, 0.45, 0.4, 0.3, 0.2, 0.1 when fall slopeindays -0.025, -0.05, -0.1, -0.15, -0.2, -0.25, -0.3, -0.4, -0.6, -0.8, -1.0, -1.2, -1.4, -1.6, -1.8 percentchange 2, 4, 6, 8, 10, 15, 20, 25, 30, 40, 50, 60, 70, 80, 90 qualify rise on percentchange fall on percentchange locate in inflammatory;

define stream MetamyelocyteNeut as "Metamyelocytes"

profile severity when high value 14|0.00001, 15|0.001 locate in inflammatory;

define stream MinuteVolume as "Minute Volume"

profile severity when high value start with 12 increase by 0.6 when rise slopeindays start with 2 increase by 0.5 magnitude start with 2 increase by 0.5 percentchange start with 20 increase by 5 when fall slopeindays start with -2 decrease by 0.5 qualify rise on magnitude locate in respiratory;

define stream Monocytes as "Monocytes"

profile severity when high value 10, 11, 12, 13, 14, 15, 16, 17, 18, 19, 20, 21, 22, 23, 24 when rise max 1, 2, 3, 4, 5, 6, 7, 8, 9, 10, 11, 12, 13, 14, 15 slopeinhours 0.2, 0.4, 0.6, 1.0, 1.4, 1.8, 2.2, 2.6, 3.0, 3.4, 3.8, 4.2, 4.6, 5.0, 5.4 percentchange 4, 5, 6, 7, 8, 9, 10, 20, 30, 40, 50, 60, 70, 80, 100 when low value 1|4, 4|3, 7|2, 10|1, 13|0 when fall

/* min 1, 2, 3, 4, 5, 6, 7, 8, 9, 10, 11, 12, 13, 14, 15 */ slopeinhours -0.2, -0.4, -0.6, -1.0, -1.4, -1.8, -2.2, -2.6, -3.0, -3.4, -3.8, -4.2, -4.6, -5.0, -5.4 percentchange 4, 5, 6, 7, 8, 9, 10, 20, 30, 40, 50, 60, 70, 80, 100 qualify rise on percentchange fall on percentchange locate in inflammatory;

define stream Neutrophils as "Neutrophils"

profile severity when high value 70, 72, 74, 76, 78, 80, 82, 84, 86, 88, 90, 92, 94, 96, 98 when rise slopeindays 4, 6, 8, 10, 12, 14, 16, 18, 20, 22, 24, 26, 28, 30, 32 magnitude 4, 6, 8, 10, 12, 14, 16, 18, 20, 24, 28, 32, 36, 40, 44 percentchange 4, 6, 8, 10, 14, 18, 24, 28, 32, 36, 40, 44, 48, 52, 56 when low value 51, 50, 49, 48, 47, 46, 44, 42, 40, 38, 34, 30, 26, 22, 18 when fall slopeindays -4, -6, -8, -10, -12, -14, -16, -18, -20, -22, -24, -26, -28, -30, -32 magnitude 4, 6, 8, 10, 12, 14, 16, 18, 20, 24, 28, 32, 36, 40, 44 percentchange 4, 6, 8, 10, 14, 18, 24, 28, 32, 36, 40, 44, 48, 52, 56 qualify rise on magnitude fall on magnitude locate in inflammatory;

define stream NeutrophilsAbs as "Neutrophils Abs"

profile severity when high value 8.5, 9, 9.5, 10, 10.5, 11, 12, 13, 14, 15, 16, 17, 18, 19, 21 when rise max 8.5, 9, 9.5, 10, 10.5, 11, 12, 13, 14, 15, 16, 17, 18, 19, 21 magnitude start with 1 increase by 1 when low value start with 2 decrease by 0.1 when fall min start with 3 decrease by 0.2 qualify rise on magnitude locate in inflammatory;

define stream NucleatedRBC as "Nucleated RBC"

profile severity when high value 14|0.00001, 15|0.001 locate in inflammatory;

define stream NucleatedRBCabs as "Nucleated RBC Abs"

profile severity when high value 14|0.00001, 15|0.001 locate in inflammatory;

define stream OxSat as "SpO2", "O2 SAT, Arterial", "SaO2"

profile severity when low value start with 93 decrease by 1 when fall min start with 2 decrease by 0.05 slopeindays start with -4 decrease by 2 magnitude start with 4 increase by 2 percentchange start with 4 increase by 1 when rise slopeindays start with 4 increase by 2 qualify

> fall on magnitude locate in respiratory;

define stream PHBlood as "pH, Arterial", "PH"

> profile severity
>> when low
>>> value start with 7.33 decrease by 0.02
>> when fall
>>> magnitude start with .0020 increase by 0.0015
> qualify
>> fall on magnitude locate in acidbase;

define stream PaCO2 as "Arterial PaCO2"

> profile severity
>> when low
>>> value start with 34 decrease by 1
>> when fall
>>> min start with 4 decrease by 0.5
>>> slopeindays start with -4 decrease by 0.5
>>> magnitude start with 4 increase by 0.5
>>> percentchange start with 12 increase by 2
>> when rise
>>> slopeindays start with 4 increase by 0.5
> qualify
>> fall on magnitude locate in respiratory;

define stream Platelets as "Platelets"

> profile severity
>> when low
>>> value 160, 150, 140, 130, 120, 110, 100, 90, 80, 70, 60, 50, 40, 30, when fall min 160, 150, 140, 130, 120, 110, 100, 90, 80, 70, 60, 50, 40, 30, 20 magnitude start with 40 increase by 12 qualify fall on magnitude locate in haemostatic;

define stream Potassium as "Potassium"

profile severity when high value 4.8, 4.9, 5.0, 5.1, 5.2, 5.3, 5.4, 5.5, 5.6, 5.7, 5.8, 5.9, 6.0, 6.1, 6.2 when rise slopeindays 0.02, 0.04, 0.06, 0.08, 0.10, 0.12, 0.14, 0.18, 0.22, 0.26, 0.30, 0.34, 0.38, 0.42, 0.46 magnitude 0.04, 0.08, 0.12, 0.16, 0.20, 0.24, 0.26, 0.30, 0.34, 0.38, 0.42, 0.46, 0.50, 0.54, 0.58 percentchange 1, 2, 3, 4, 5, 6, 7, 8, 9, 10, 11, 12, 13, 14, 15 when low value 3.7, 3.6, 3.5, 3.4, 3.3, 3.2, 3.1, 3.0, 2.9, 2.8, 2.7, 2.6, 2.5, 2.4, 2.3 when fall slopeindays -0.02, -0.04, -0.06, -0.08, -0.10, -0.12, -0.14, -0.18, -0.22, -0.26, -0.30, -0.34, -0.38, -0.42, -0.46 magnitude 0.04, 0.08, 0.12, 0.16, 0.20, 0.24, 0.26, 0.30, 0.34, 0.38, 0.42, 0.46, 0.50, 0.54, 0.58 percentchange 1, 2, 3, 4, 5, 6, 7, 8, 9, 10, 11, 12, 13, 14, 15 qualify rise on magnitude fall on magnitude locate in electrolytic;

define stream HR as "Pulse", "Heart Rate"

profile severity when high value start with 90 increase by 5 when rise slopeindays start with 15 increase by 2 magnitude start with 15 increase by 2 percentchange start with 20 increase by 5 when fall min start with 90 decrease by 5 magnitude start with 15 increase by 5 qualify rise on magnitude fall on magnitude locate in cardiac;

define stream Procalcitonin as "Procalcitonin"

profile severity when high value start with 0.15 increase by 0.05 when rise slopeindays start with 0.2 increase by 0.03 magnitude start with 0.2 increase by 0.05 percentchange start with 10 increase by 2 when fall slopeindays start with -0.2 decrease by 0.03 qualify rise on magnitude locate in inflammatory;

define stream RespiratoryRate as "Respiratory Rate"

profile severity when high value start with 18 increase by 1 when rise max start with 18 increase by 1 magnitude start with 4 increase by 1 qualify rise on magnitude locate in respiratory;

define stream SegsAbs as "Segs Abs"

profile severity when high value 6.5, 6.75, 7, 7.2, 7.4, 7.6, 8, 9, 10, 11, 13, 15, 17, 19, 21 when rise slopeindays 0.25, 0.5, 0.75, 1, 2, 3, 4, 5, 6, 8, 10, 12, 14, 16, 18 percentchange 4, 6, 8, 10, 20, 30, 40, 50, 60, 70, 80, 90, 100, 120, 140 when low value 2, 1.9, 1.7, 1.6, 1.5, 1.4, 1.3, 1.2, 1.1, 1, 0.8, 0.6, 0.5, 0.4, 0.3 when fall slopeindays -0.1, -0.15, -0.2, -0.3, -0.4, -0.5, -0.75, -1.0, -1.5, -2, -2.5, -3, -3.5, -4, -4.5 percentchange 4, 5, 6, 8, 10, 12, 15, 20, 30, 40, 50, 60, 70, 80, 90 qualify rise on percentchange fall on percentchange locate in inflammatory;

define stream Segs as "Segs"

profile severity when high value 61, 62, 63, 64, 66, 68, 70, 74, 78, 84, 88, 92, 94, 96, 98 when rise slopeindays 1, 2, 3, 4, 5, 6, 7, 8, 9, 10, 11, 12, 13, 14, 15 magnitude 2, 3, 4, 6, 8, 10, 12, 14, 16, 18, 20, 22, 24, 26, 30 percentchange 2, 3, 4, 5, 8, 12, 16, 20, 25, 30, 40, 50, 60, 70, 80 when low value 34, 33, 32, 31, 30, 28, 26, 24, 22, 20, 18, 14, 10, 8, 6 when fall slopeindays -1, -2, -3, -4, -5, -6, -7, -8, -9, -10, -11, -12, -13, -14, -15 magnitude 2, 3, 4, 6, 8, 10, 12, 14, 16, 18, 20, 22, 24, 26, 30 percentchange 2, 3, 4, 5, 8, 12, 16, 20, 25, 30, 40, 50, 60, 70, 80 qualify rise on magnitude fall on magnitude locate in inflammatory;

define stream Sodium as "Sodium"

profile severity when high value 143, 144, 145, 146, 147, 148, 149, 150, 151, 152, 153, 154, 155, 156, 157 when rise slopeindays 0.4, 0.6, 0.8, 1, 1.4, 1.8, 2.2, 2.6, 3, 3.4, 3.8, 4.2, 4.6, 5.0, 5.4 magnitude 1, 2, 2.4, 2.8, 3.2, 3.6, 4, 4.4, 4.8, 5.2, 5.6, 6, 6.4, 6.8, 7.2 percentchange 0.5, 0.8, 1, 1.4, 1.6, 1.8, 2, 2.4, 2.8, 3.2, 3.6, 4.0, 4.4, 4.8, 5.2 when low value 137, 136, 135, 134, 133, 132, 131, 130, 129, 128, 127, 126, 125, 124, 123 when fall slopeindays -0.4, -0.6, -0.8, -1, -1.4, -1.8, -2.2, -2.6, -3, -3.4, -3.8, -4.2, -4.6, -5.0, -5.4 magnitude 1, 2, 2.4, 2.8, 3.2, 3.6, 4, 4.4, 4.8, 5.2, 5.6, 6, 6.4, 6.8, 7.2 percentchange 0.5, 0.8, 1, 1.4, 1.6, 1.8, 2, 2.4, 2.8, 3.2, 3.6, 4.0, 4.4, 4.8, 5.2 qualify

> rise on magnitude fall on magnitude

> locate in electrolytic;

define stream TemperatureC as "Temperature C"

profile severity when high value 37.22, 37.33, 37.44, 37.56, 37.67, 37.78, 38.06, 38.33, 38.61, 38.89, 39.44, 40.00, 40.56, 41.11, 41.67 when rise max 37.22, 37.33, 37.44, 37.56, 37.67, 37.78, 38.06, 38.33, 38.61, 38.89, 39.44, 40.00, 40.56, 41.11, 41.67 magnitude 0.22, 0.28, 0.33, 0.39, 0.44, 0.50, 0.56, 0.78, 1.00, 1.22, 1.44, 1.67, 1.78, 1.89, 2.00 when low value start with 36.33 decrease by 0.056 when fall min start with 36.33 decrease by 0.056 magnitude 0.22, 0.28, 0.33, 0.39, 0.44, 0.50, 0.56, 0.78, 1.00, 1.22, 1.44, 1.67, 1.78, 1.89, 2.00 qualify rise on magnitude fall on magnitude locate in inflammatory;

define stream TemperatureF as "Temperature F"

profile severity when high value 99, 99.2, 99.4, 99.6, 99.8, 100, 100.5, 101, 101.5, 102, 103, 104, 105, 106, 107 when rise max 99, 99.2, 99.4, 99.6, 99.8, 100, 100.5, 101, 101.5, 102, 103, 104, 105, 106, 107 magnitude 0.4, 0.5, 0.6, 0.7, 0.8, 0.9, 1.0, 1.4, 1.8, 2.2, 2.6, 3.0, 3.2, 3.4, 3.6 when low value start with 97.4 decrease by 0.1 when fall min start with 97.4 decrease by 0.1 magnitude 0.4, 0.5, 0.6, 0.7, 0.8, 0.9, 1.0, 1.4, 1.8, 2.2, 2.6, 3.0, 3.2, 3.4, 3.6 qualify rise on magnitude fall on magnitude locate in inflammatory;

define stream WBC as "WBC"

profile severity when high value 12.5, 13, 13.5, 14, 15.5, 16, 17, 18, 19, 20, 21, 22, 23, 25, 27 when rise max 12.5, 13, 13.5, 14, 15.5, 16, 17, 18, 19, 20, 21, 22, 23, 25, 27 magnitude start with 2 increase by 1 when low value 4.2, 4.1, 4.0, 3.9, 3.8, 3.7, 3.5, 3.3, 3.1, 2.8, 2.6, 2.4, 2.0, 1.6, 1.2 when fall min 4.2, 4.1, 4.0, 3.9, 3.8, 3.7, 3.5, 3.3, 3.1, 2.8, 2.6, 2.4, 2.0, 1.6, 1.2 qualify rise on magnitude and max locate in inflammatory;

-- Streams without severity define stream AaDO2 as "AaDO2" locate in respiratory;

define stream ABP_Diastolic_NBP as "ABP Diastolic NBP" locate in hematologic;

define stream Alk_Phos as "Alk Phos" locate in metabolic;

define stream ALT_SGPT as "ALT(SGPT)" locate in hepatic;

define stream Amylase as "Amylase" locate in inflammatory;

define stream APTT as "APTT" locate in haemostatic;

define stream Arterial_Base_Excess as "Arterial Base Excess" locate in acidbase;

define stream Arterial_Glucose as "Glucose Art" locate in metabolic;

define stream Arterial_Hematocrit as "Hematocrit Art" locate in hematologic;

define stream Arterial_PaO2 as "Arterial PaO2" locate in respiratory;

define stream Arterial_Potassium as "Potassium Art" locate in electrolytic;

define stream Arterial_Sodium as "Sodium Art" locate in electrolytic;

define stream AST_SGOT as "AST(SGOT)" locate in inflammatory;

define stream Basophils as "Basophils" locate in metabolic;

define stream Bilirubin_Direct as "Bilirubin Direct" locate in hematologic;

define stream Bilirubin_Total as "Bilirubin Total" locate in electrolytic;

define stream BIPAP_IPAP as "BIPAP - IPAP" locate in respiratory;

define stream BIPAP_EPAP as "BIPAP - EPAP" locate in respiratory;

define stream BNP as "BNP" locate in cardiac;

define stream CaO2 as "CaO2" locate in respiratory;

define stream CK_MB as "CK-MB" locate in inflammatory;

define stream CK_Total as "CK Total" locate in renal;

define stream CVP as "CVP" locate in cardiac;

define stream D_Dimer as "D-Dimer" locate in haemostatic;

define stream Eosinophils as "Eosinophils" locate in inflammatory;

define stream Eosinophils_Abs as "Eosinophils Abs" locate in inflammatory;

define stream INR as "INR" locate in haemostatic;

define stream Lactic_Acid as "Lactic Acid" locate in acidbase;

define stream Lipase as "Lipase" locate in inflammatory;

define stream Lymph_Atypical_Abs as "Lymph Atypical Abs" locate in inflammatory;

define stream MCH as "MCH" locate in hematologic;

define stream MCHC as "MCHC" locate in hematologic;

define stream MCV as "MCV" locate in hematologic;

define stream MPV as "MPV" locate in hematologic;

define stream Magnesium as "Magnesium" locate in electrolytic;

define stream Metamyelocytes_Abs as "Metamyelocytes Abs" locate in inflammatory;

define stream Myelocyte_Abs as "Myelocyte Abs" locate in inflammatory;

define stream Monocytes_Abs as "Monocytes Abs" locate in inflammatory;

define stream Myelocyte as "Myelocyte" locate in inflammatory;

define stream O2_Flow as "O2 Flow" locate in respiratory;

define stream Osmolality as "Osmolality" locate in metabolic;

define stream PEEP as "PEEP" locate in respiratory;

define stream Phosphorus as "Phosphorus" locate in electrolytic;

define stream Pressure_Support as "Pressure Support" locate in respiratory;

define stream PT as "PT" locate in haemostatic;

define stream RBC as "RBC" locate in hematologic;

define stream RDW_CV as "RDW - CV" locate in hematologic;

define stream SaO2_Calculated as "SaO2 Calc" locate in respiratory;

define stream Spon_RR_Mech as "Spon RR (Mech.)" locate in respiratory;

define stream Spon_Vt_L_Mech as "Spon. Vt (L) (Mech.)" locate in respiratory;

define stream Total_Protein as "Total Protein" locate in respiratory;

define stream Troponin as "Troponin" locate in respiratory;

define stream Uric_Acid as "Uric Acid" locate in metabolic;

--Temp

Identify TempRiseOrHighMarginal as TemperatureFRiseMarginal or TemperatureFHighMarginal Locate in inflammatory;

Identify TempRiseOrHighMild as TemperatureFRiseMild or TemperatureFHighMild Locate in inflammatory;

Identify TempRiseOrHighModerate as TemperatureFRiseModerate or TemperatureFHighModerate Locate in inflammatory;

Identify TempRiseOrHighSevere as TemperatureFRiseSevere or TemperatureFHighSevere Locate in inflammatory;

Identify TempRiseOrHighProfound as TemperatureFRiseProfound or TemperatureFHighMild Locate in inflammatory;

Identify TempFallOrLowMarginal as TemperatureFFallMarginal or TemperatureFLowMarginal Locate in inflammatory;

Identify TempFallOrLowMild as TemperatureFFallMild or TemperatureFLowMild Locate in inflammatory;

Identify TempFallOrLowMod as TemperatureFFallModerate or TemperatureFLowModerate Locate in inflammatory;

Identify TempFallOrLowSevere as TemperatureFFallSevere or TemperatureFLowSevere Locate in inflammatory;

Identify TempFallOrLowProfound as TemperatureFFallProfound or TemperatureFLowProfound Locate in inflammatory;

Identify TempBiphasicMarginal as TemperatureFRiseMarginal and TemperatureFFall within 1d Locate in inflammatory;

Identify TempBiphasicMild as TemperatureFRiseMild and TemperatureFFall within 1d Locate in inflammatory;

Identify TempBiphasicMod as TemperatureFRiseModerate and TemperatureFFall within 1d Locate in inflammatory;

Identify TempBiphasicSevere as TemperatureFRiseSevere and TemperatureFFall within 1d Locate in inflammatory;

Identify TempBiphasicProfound as TemperatureFRiseProfound and TemperatureFFall within 1d Locate in inflammatory;

--Band / BandAbs Rise or High identify BandsRiseOrHighMarginal as BandsRiseMarginal or BandsHighMarginal locate in inflammatory;

identify BandsRiseOrHighMild as BandsRiseMild or BandsHighMild locate in inflammatory;

identify BandsRiseOrHighMod as BandsRiseModerate or BandsHighModerate locate in inflammatory;

identify BandsRiseOrHighSevere as BandsRiseSevere or BandsHighSevere locate in inflammatory;

identify BandsRiseOrHighProfound as BandsRiseProfound or BandsHighProfound locate in inflammatory;

identify BandsAbsRiseOrHighMarginal as BandsAbsRiseMarginal or BandsAbsHighMarginal locate in inflammatory;

identify BandsAbsRiseOrHighMild as BandsAbsRiseMild or BandsAbsHighMild locate in inflammatory;

identify BandsAbsRiseOrHighMod as BandsAbsRiseModerate or BandsAbsHighModerate locate in inflammatory;

identify BandsAbsRiseOrHighSevere as BandsAbsRiseSevere or BandsAbsHighSevere locate in inflammatory;

identify BandsAbsRiseOrHighProfound as BandsAbsRiseProfound or BandsAbsHighProfound locate in inflammatory;

---WBC Rise Or Fall identify WBCRiseOrHighMarginal as WBCRiseMarginal or WBCHighMarginal locate in inflammatory;

identify WBCRiseOrHighMild as WBCRiseMild or WBCHighMild locate in inflammatory;

identify WBCRiseOrHighMod as WBCRiseModerate or WBCHighModerate locate in inflammatory;

identify WBCRiseOrHighSevere as WBCRiseSevere or WBCHighSevere locate in inflammatory;

identify WBCRiseOrHighProfound as WBCRiseProfound or WBCHighProfound locate in inflammatory;

identify WBCLowOrFallMarginal as WBCFallMarginal or WBCLowMarginal locate in inflammatory;

identify WBCLowOrFallMild as WBCFallMild or WBCLowMild locate in inflammatory;

identify WBCLowOrFallMod as WBCFallModerate or WBCLowModerate locate in inflammatory;

identify WBCLowOrFallSevere as WBCFallSevere or WBCLowSevere locate in inflammatory;

identify WBCLowOrFallProfound as WBCFallProfound or WBCLowProfound locate in inflammatory;

---Neutrophils / Neutrophils Rise Or High identify NeutrophilsHighOrRiseMarginal as NeutrophilsRiseMarginal or NeutrophilsHighMarginal locate in inflammatory;

identify NeutrophilsHighOrRiseMild as NeutrophilsRiseMild or NeutrophilsHighMild locate in inflammatory;

identify NeutrophilsHighOrRiseMod as NeutrophilsRiseModerate or NeutrophilsHighModerate locate in inflammatory;

identify NeutrophilsHighOrRiseSevere as NeutrophilsRiseSevere or NeutrophilsHighSevere locate in inflammatory;

identify NeutrophilsHighOrRiseProfound as NeutrophilsRiseProfound or NeutrophilsHighProfound locate in inflammatory;

identify NeutrophilsAbsHighOrRiseMarginal as NeutrophilsAbsRiseMarginal or NeutrophilsAbsHighMarginal locate in inflammatory;

identify NeutrophilsAbsHighOrRiseMild as NeutrophilsAbsRiseMild or NeutrophilsAbsHighMild locate in inflammatory;

identify NeutrophilsAbsHighOrRiseMod as NeutrophilsAbsRiseModerate or NeutrophilsAbsHighModerate locate in inflammatory;

identify NeutrophilsAbsHighOrRiseSevere as NeutrophilsAbsRiseSevere or NeutrophilsAbsHighSevere locate in inflammatory;

identify NeutrophilsAbsHighOrRiseProfound as NeutrophilsAbsRiseProfound or NeutrophilsAbsHighProfound locate in inflammatory;

---Neutrophils / Neutrophils Low Or Fall identify NeutrophilsLowOrFallMarginal as NeutrophilsFallMarginal or NeutrophilsLowMarginal locate in inflammatory;

identify NeutrophilsLowOrFallMild as NeutrophilsFallMild or NeutrophilsLowMild locate in inflammatory;

identify NeutrophilsLowOrFallMod as NeutrophilsFallModerate or NeutrophilsLowModerate locate in inflammatory;

identify NeutrophilsLowOrFallSevere as NeutrophilsFallSevere or NeutrophilsLowSevere locate in inflammatory;

identify NeutrophilsLowOrFallProfound as NeutrophilsFallProfound or NeutrophilsLowProfound locate in inflammatory;

identify NeutrophilsAbsLowOrFallMarginal as NeutrophilsAbsFallMarginal or NeutrophilsAbsLowMarginal locate in inflammatory;

identify NeutrophilsAbsLowOrFallMild as NeutrophilsAbsFallMild or NeutrophilsAbsLowMild locate in inflammatory;

identify NeutrophilsAbsLowOrFallMod as NeutrophilsAbsFallModerate or NeutrophilsAbsLowModerate locate in inflammatory;

identify NeutrophilsAbsLowOrFallSevere as NeutrophilsAbsFallSevere or NeutrophilsAbsLowSevere locate in inflammatory;

identify NeutrophilsAbsLowOrFallProfound as NeutrophilsAbsFallProfound or NeutrophilsAbsLowProfound locate in inflammatory;

---LymphocytesAbs Low Or Fall identify LymphocytesAbsLowOrFallMarginal as LymphocytesAbsFallMarginal or LymphocytesAbsLowMarginal locate in inflammatory;

identify LymphocytesAbsLowOrFallMild as LymphocytesAbsFallMild or LymphocytesAbsLowMild locate in inflammatory;

identify LymphocytesAbsLowOrFallMod as LymphocytesAbsFallModerate or LymphocytesAbsLowModerate locate in inflammatory;

identify LymphocytesAbsLowOrFallSevere as LymphocytesAbsFallSevere or LymphocytesAbsLowSevere locate in inflammatory;

identify LymphocytesAbsLowOrFallProfound as LymphocytesAbsFallProfound or LymphocytesAbsLowProfound locate in inflammatory;

---Pathophysiologically Divergence or Decoherence (PD) of LymphocytesAbs in Relation to Bands Bands Abs indicative of Inflammation, Stress, or Lymphocyte depletion Identify PDLymphocytesAbsBandsMarginal as BandsRiseorHighMarginal and LymphocytesAbsFallMarginal within 1d Locate in inflammatory;

Identify PDLymphocytesAbsBandsMild as BandsRiseorHighMild and LymphocytesAbsFallMild within 1d Locate in inflammatory;

Identify PDLymphocytesAbsBandsMod as BandsRiseorHighMod and LymphocytesAbsFallModerate within 1d Locate in inflammatory;

Identify PDLymphocytesAbsBandsSevere as BandsRiseorHighSevere and LymphocytesAbsFallSevere within 1d Locate in inflammatory;

Identify PDLymphocytesAbsBandsProfound as BandsRiseorHighProfound and LymphocytesAbsFallProfound within 1d Locate in inflammatory;

identify PDLymphocytesAbsBandsAbsMarginal as BandsAbsRiseorHighMarginal and LymphocytesAbsFallMarginal within 1d Locate in inflammatory;

Identify PDLymphocytesAbsBandsAbsMild as BandsAbsRiseorHighMild and LymphocytesAbsFallMild within 1d Locate in inflammatory;

Identify PDLymphocytesAbsBandsAbsMod as BandsAbsRiseorHighMod and LymphocytesAbsFallModerate within 1d Locate in inflammatory;

Identify PDLymphocytesAbsBandsAbsSevere as BandsAbsRiseorHighSevere and LymphocytesAbsFallSevere within 1d Locate in inflammatory;

Identify PDLymphocytesAbsBandsAbsProfound as BandsAbsRiseorHighProfound and LymphocytesAbsFallProfound within 1d Locate in inflammatory;

---Pathophysiologically Divergence or Decoherence (PD) of LymphocytesAbs in Relation to Neutrophils/NeutrophilsAbs indicative of Inflammation, Stress, or Lymphocyte depletion identify PDLymphocytesAbsNeutrophilsAbsMarginal as NeutrophilsAbsHighorRiseMarginal and LymphocytesAbsFallMarginal within 1d Locate in inflammatory;

Identify PDLymphocytesAbsNeutrophilsAbsMild as NeutrophilsAbsHighorRiseMild and LymphocytesAbsFallMild within 1d Locate in inflammatory;

Identify PDLymphocytesAbsNeutrophilsAbsMod as NeutrophilsAbsHighorRiseMod and LymphocytesAbsFallModerate within 1d Locate in inflammatory;

Identify PDLymphocytesAbsNeutrophilsAbsSevere as NeutrophilsAbsHighorRiseSevere and LymphocytesAbsFallSevere within 1d Locate in inflammatory;

Identify PDLymphocytesAbsNeutrophilsAbsProfound as NeutrophilsAbsHighorRiseProfound and LymphocytesAbsFallProfound within 1d Locate in inflammatory;

identify PDLymphocytesAbsWBCMarginal as WBCRiseorHighMarginal and LymphocytesAbsFallMarginal within 1d Locate in inflammatory;

Identify PDLymphocytesAbsWBCMild as WBCRiseorHighMild and LymphocytesAbsFallMild within 1d Locate in inflammatory;

Identify PDLymphocyteAbssWBCMod as WBCRiseorHighMod and LymphocytesAbsFallModerate within 1d Locate in inflammatory;

Identify PDLymphocytesAbsWBCSevere as WBCRiseorHighSevere and LymphocytesAbsFallSevere within 1d Locate in inflammatory;

Identify PDLymphocytesAbsWBCProfound as WBCRiseorHighProfound and LymphocytesAbsFallProfound within 1d Locate in inflammatory;

---Pathophysiologically Divergence or Decoherence of WBC and Bands(PD) indicative of Neutrophil Failure (in relation to WBC)

Identify PDWBCBandsMarginal as BandsRiseorHighMarginal and WBCLowOrFallMarginal within 1d Locate in inflammatory;

Identify PDWBCBandsMild as BandsRiseorHighMild and WBCLowOrFallMild within 1d Locate in inflammatory;

Identify PDWBCBandsMod as BandsRiseorHighMod and WBCLowOrFallMod within 1d Locate in inflammatory;

Identify PDWBCBandsSevere as BandsRiseorHighSevere and WBCLowOrFallSevere within 1d Locate in inflammatory;

Identify PDWBCBandsProfound as BandsRiseorHighProfound and WBCLowOrFallProfound within 1d Locate in inflammatory;

Identify PDWBCBandsMod2 as BandsRiseorHighMod and WBCRiseOrHighMarginal within 1d Locate in inflammatory;

Identify PDWBCBandsSevere2 as BandsRiseorHighSevere and WBCRiseOrHighMild within 1d Locate in inflammatory;

Identify PDWBCBandsProfound2 as BandsRiseorHighProfound and WBCLowOrFallMod within 1d Locate in inflammatory;

---Pathophysiologically Divergence or Decoherence (PD) of Neutrophils and Bands indicative of Neutrophil Failure (in relation to mature Neutrophils)

Identify PDNeutrophilsBandsMarginal as BandsRiseorHighMarginal and NeutrophilsLowOrFallMarginal within 1d Locate in inflammatory;

Identify PDNeutrophilsBandsMild as BandsRiseorHighMild and NeutrophilsLowOrFallMild within 1d Locate in inflammatory;

Identify PDNeutrophilsBandsMod as BandsRiseorHighMod and NeutrophilsLowOrFallMod within 1d Locate in inflammatory;

Identify PDNeutrophilsBandsSevere as BandsRiseorHighSevere and NeutrophilsLowOrFallSevere within 1d Locate in inflammatory;

Identify PDNeutrophilsBandsProfound as BandsRiseorHighProfound and NeutrophilsLowOrFallProfound within 1d Locate in inflammatory;

Identify PDNeutrophilsBandsMod2 as BandsRiseorHighMod and NeutrophilsLowOrFallMarginal within 1d Locate in inflammatory;

Identify PDNeutrophilsBandsSevere2 as BandsRiseorHighSevere and NeutrophilsLowOrFallMild within 1d Locate in inflammatory;

Identify PDNeutrophilsBandsProfound2 as BandsRiseorHighProfound and NeutrophilsLowOrFallMod within 1d Locate in inflammatory;

Identify PDNeutrophilsAbsBandsMarginal as BandsAbsRiseorHighMarginal and NeutrophilsAbsLowOrFallMarginal within 1d Locate in inflammatory;

Identify PDNeutrophilsAbsBandsMild as BandsAbsRiseorHighMild and NeutrophilsAbsLowOrFallMild within 1d Locate in inflammatory;

Identify PDNeutrophilsAbsBandsMod as BandsAbsRiseorHighMod and NeutrophilsAbsLowOrFallMod within 1d Locate in inflammatory;

Identify PDNeutrophilsAbsBandsSevere as BandsAbsRiseorHighSevere and NeutrophilsAbsLowOrFallSevere within 1d Locate in inflammatory;

Identify PDNeutrophilsAbsBandsProfound as BandsAbsRiseorHighProfound and NeutrophilsAbsLowOrFallProfound within 1d Locate in inflammatory;

Identify PDNeutrophilsAbsBandsMod2 as BandsAbsRiseorHighMod and NeutrophilsAbsLowOrFallMarginal within 1d Locate in inflammatory;

Identify PDNeutrophilsAbsBandsSevere2 as BandsAbsRiseorHighSevere and NeutrophilsAbsLowOrFallMild within 1d Locate in inflammatory;

Identify PDNeutrophilsAbsBandsProfound2 as BandsAbsRiseorHighProfound and NeutrophilsAbsLowOrFallMod within 1d Locate in inflammatory;

---Neutrophil Failure (Combined)

Identify NeutrophilFailureMarginal as PDNeutrophilsBandsMarginal or PDNeutrophilsAbsBandsMarginal or PDWBCBandsMarginal or PDNeutrophilsAbsBandsMod2 or PDNeutrophilsBandsMod2 locate in inflammatory;

Identify NeutrophilFailureMild as PDNeutrophilsBandsMild or PDNeutrophilsAbsBandsMild or PDWBCBandsMild or PDNeutrophilsAbsBandsSevere2 or PDNeutrophilsBandsSevere2 locate in inflammatory;

Identify NeutrophilFailureMod as PDNeutrophilsBandsMod or PDNeutrophilsAbsBandsMod or PDWBCBandsMod or PDNeutrophilsAbsBandsProfound2 or PDNeutrophilsBandsProfound2 locate in inflammatory;

Identify NeutrophilFailureSevere as PDNeutrophilsBandsSevere or PDNeutrophilsAbsBandsSevere or PDWBCBandsSevere locate in inflammatory;

Identify NeutrophilFailureProfound as PDNeutrophilsBandsProfound or PDNeutrophilsAbsBandsProfound or PDWBCBandsProfound locate in inflammatory;

--- Bands OR Neutrophil Rise or High identify NeutrophilOrBandsHighOrRiseMarginal as BandsAbsRiseOrHighMarginal or NeutrophilsAbsHighOrRiseMarginal locate in inflammatory;

identify NeutrophilOrBandsHighOrRiseMild as BandsAbsRiseOrHighMild or NeutrophilsAbsHighOrRiseMild locate in inflammatory;

identify NeutrophilOrBandsHighOrRiseMod as BandsAbsRiseOrHighMild or NeutrophilsAbsHighOrRiseMod locate in inflammatory;

identify NeutrophilOrBandsHighOrRiseSevere as BandsAbsRiseOrHighMild or NeutrophilsAbsHighOrRiseSevere locate in inflammatory;

identify NeutrophilOrBandsHighOrRiseProfound as BandsAbsRiseOrHighMild or NeutrophilsAbsHighOrRiseProfound locate in inflammatory;

-- Bands AND Neutrophil Rise or High identify NeutrophilANDBandsHighOrRiseMarginal as BandsAbsRiseOrHighMarginal and NeutrophilsAbsHighOrRiseMarginal within 1d locate in inflammatory;

identify NeutrophilANDBandsHighOrRiseMild as BandsAbsRiseOrHighMild and NeutrophilsAbsHighOrRiseMild within 1d locate in inflammatory;

identify NeutrophilANDBandsHighOrRiseMod as BandsAbsRiseOrHighMild and NeutrophilsAbsHighOrRiseMod within 1d locate in inflammatory;

identify NeutrophilANDBandsHighOrRiseSevere as BandsAbsRiseOrHighMild and NeutrophilsAbsHighOrRiseSevere within 1d locate in inflammatory;

identify NeutrophilANDBandsHighOrRiseProfound as BandsAbsRiseOrHighMild and NeutrophilsAbsHighOrRiseProfound within 1d locate in inflammatory;

--- Temp And Neutrophil And Band Rise or High identify NeutrophilAndBandAndTempMarginal as TempRiseOrHighMarginal and NeutrophilANDBandsHighOrRiseMarginal within 1d locate in inflammatory;

identify NeutrophilAndBandAndTempMild as TempRiseOrHighMild and NeutrophilANDBandsHighOrRiseMild within 1d locate in inflammatory;

identify NeutrophilAndBandAndTempMod as TempRiseOrHighModerate and NeutrophilANDBandsHighOrRiseMod within 1d locate in inflammatory;

identify NeutrophilAndBandAndTempSevere as TempRiseOrHighSevere and NeutrophilANDBandsHighOrRiseSevere within 1d locate in inflammatory;

identify NeutrophilAndBandAndTempProfound as TempRiseOrHighProfound and NeutrophilANDBandsHighOrRiseProfound within 1d locate in inflammatory;

---Temp Or Neutrophil Or Band Rise or High identify NeutrophilOrBandOrTempMarginal as TempRiseOrHighMarginal or NeutrophilOrBandsHighOrRiseMarginal locate in inflammatory;

identify NeutrophilOrBandOrTempMild as TempRiseOrHighMild or NeutrophilOrBandsHighOrRiseMild locate in inflammatory;

identify NeutrophilOrBandOrTempMod as TempRiseOrHighModerate or NeutrophilOrBandsHighOrRiseMod locate in inflammatory;

identify NeutrophilOrBandOrTempSevere as TempRiseOrHighSevere or NeutrophilOrBandsHighOrRiseSevere locate in inflammatory;

identify NeutrophilOrBandOrTempProfound as TempRiseOrHighProfound or NeutrophilOrBandsHighOrRiseProfound locate in inflammatory;

---Biomarker Procalcitonin Rise Or High identify ProcalcitoninRiseOrHighMarginal as ProcalcitoninRiseMarginal or ProcalcitoninHighMarginal locate in inflammatory;

identify ProcalcitoninRiseOrHighMild as ProcalcitoninRiseMild or ProcalcitoninHighMild locate in inflammatory;

identify ProcalcitoninRiseOrHighMod as ProcalcitoninRiseModerate or ProcalcitoninHighModerate locate in inflammatory;

identify ProcalcitoninRiseOrHighSevere as ProcalcitoninRiseSevere or ProcalcitoninHighSevere locate in inflammatory;

identify ProcalcitoninRiseOrHighProfound as ProcalcitoninRiseProfound or ProcalcitoninHighProfound locate in inflammatory;

--Neutrophil Or Band Or Temp and Procalcitonin identify NeutrophilOrBandOrTempProcalcitonMarginal as NeutrophilOrBandOrTempMarginal and ProcalcitoninRiseOrHighMarginal within 2d locate in inflammatory;

identify NeutrophilOrBandOrTempProcalcitoninMild as NeutrophilOrBandOrTempMild and ProcalcitoninRiseOrHighMild within 2d locate in inflammatory;

identify NeutrophilOrBandOrTempProcalcitoninMod as NeutrophilOrBandOrTempMod and ProcalcitoninRiseOrHighMod within 2d locate in inflammatory;

identify NeutrophilOrBandOrTempProcalcitoninSevere as NeutrophilOrBandOrTempSevere and ProcalcitoninRiseOrHighSevere within 2d locate in inflammatory;

identify NeutrophilOrBandOrTempProcalcitonProfound as NeutrophilOrBandOrTempProfound and ProcalcitoninRiseOrHighProfound within 2d locate in inflammatory;

identify NeutrophilAndBandAndTempProcalcitonMarginal as NeutrophilAndBandAndTempMarginal and ProcalcitoninRiseOrHighMarginal within 2d locate in inflammatory;

identify NeutrophilAndBandAndTempProcalcitoninMild as NeutrophilAndBandAndTempMild and ProcalcitoninRiseOrHighMild within 2d locate in inflammatory;

identify NeutrophilAndBandAndTempProcalcitoninMod as NeutrophilAndBandAndTempMod and ProcalcitoninRiseOrHighMod within 2d locate in inflammatory;

identify NeutrophilAndBandAndTempProcalcitoninSevere as NeutrophilAndBandAndTempSevere and ProcalcitoninRiseOrHighSevere within 2d locate in inflammatory;

identify NeutrophilAndBandAndTempProcalcitonProfound as NeutrophilAndBandAndTempProfound and ProcalcitoninRiseOrHighProfound within 2d locate in inflammatory;

--Respiratory

Identify SaO2LowOrFallMarginal as OxSatLowMarginal or OxSatFallMarginal Locate in respiratory;

Identify SaO2LowOrFallMild as OxSatLowMild or OxSatFallMild Locate in respiratory;

Identify SaO2LowOrFallMod as OxSatLowModerate or OxSatFallModerate Locate in respiratory;

Identify SaO2LowOrFallSevere as OxSatLowSevere or OxSatFallSevere Locate in respiratory;

Identify SaO2LowOrFallProfound as OxSatLowProfound or OxSatFallProfound Locate in respiratory;

Identify RRHighOrRiseMarginal as RespiratoryRateHighMarginal or
RespiratoryRateRiseMarginal Locate in respiratory;

Identify RRHighOrRiseMild as RespiratoryRateHighMild or RespiratoryRateRiseMild Locate in respiratory;

Identify RRHighOrRiseMod as RespiratoryRateHighModerate or RespiratoryRateRiseModerate Locate in respiratory;

Identify RRHighOrRiseSevere as RespiratoryRateHighSevere or RespiratoryRateRiseSevere Locate in respiratory;

Identify RRHighOrRiseProfound as RespiratoryRateHighProfound or
RespiratoryRateRiseProfound Locate in respiratory;

Identify PDSPO2RRMarginal as RRHighOrRiseMarginal and SaO2LowOrFallMarginal within 1d Locate in respiratory;

Identify PDSPO2RRMild as RRHighOrRiseMild and SaO2LowOrFallMild within 1d Locate in respiratory;

Identify PDSPO2RRMod as RRHighOrRiseMod and SaO2LowOrFallMod within 1d Locate in respiratory;

Identify PDSPO2RRSevere as RRHighOrRiseSevere and SaO2LowOrFallSevere within 1d Locate in respiratory;

Identify PDSPO2RRProfound as RRHighOrRiseProfound and SaO2LowOrFallProfound within 1d Locate in respiratory;

--Acid Base

Identify BicarbFallOrLowMarginal as BicarbFallMarginal or BicarbLowMarginal locate in acidbase;

Identify BicarbFallOrLowMild as BicarbFallMild or BicarbLowMild locate in acidbase;

Identify BicarbFallOrLowMod as BicarbFallModerate or BicarbLowModerate locate in acidbase;

Identify BicarbFallOrLowSevere as BicarbFallSevere or BicarbLowSevere locate in acidbase;

Identify BicarbFallOrLowProfound as BicarbFallProfound or BicarbLowProfound locate in acidbase;

identify Acidosis as AnionGapRise or AnionGapHigh or PHBloodLow locate in acidbase;

identify AcidosisMarginal as AnionGapRiseMarginal or AnionGapHighMarginal or PHBloodLowMarginal locate in acidbase;

identify AcidosisMild as AnionGapRiseMild or AnionGapHighMild or PHBloodLowMild locate in acidbase;

identify AcidosisMod as AnionGapRiseModerate or AnionGapHighModerate or PHBloodLowModerate locate in acidbase;

identify AcidosisSevere as AnionGapRiseSevere or AnionGapHighSevere or PHBloodLowSevere locate in acidbase;

identify AcidosisProfound as AnionGapRiseProfound or AnionGapHighProfound or PHBloodLowProfound locate in acidbase;

Identify LactateRiseOrHighMarginal as LactateRiseMarginal or LactateHighMarginal locate in acidbase;

Identify LactateRiseOrHighMild as LactateRiseMild or LactateHighMild locate in acidbase;

Identify LactateRiseOrHighMod as LactateRiseModerate or LactateHighModerate locate in acidbase;

Identify LactateRiseOrHighSevere as LactateRiseSevere or LactateHighSevere locate in acidbase;

Identify LactateRiseOrHighProfound as LactateRiseProfound or LactateHighProfound locate in acidbase;

identify LacticAcidosisMarginal as AcidosisMarginal and LactateHighMarginal within 9h locate in acidbase;

identify LacticAcidosisMild as AcidosisMild and LactateHighMild within 9h locate in acidbase;

identify LacticAcidosisMod as AcidosisMod and LactateHighModerate within 9h locate in acidbase;

identify LacticAcidosisSevere as AcidosisSevere and LactateHighSevere within 9h locate in acidbase;

identify LacticAcidosisProfound as AcidosisProfound and LactateHighProfound within 9h locate in acidbase;

Identify AcidosisOrBicarbFallorLoworLactateMarginal as AcidosisMarginal or BicarbFallOrLowMarginal or LactateRiseOrHighMarginal or LacticAcidosisMarginal locate in acidbase;

Identify AcidosisOrBicarbFallorLoworLactateMild as AcidosisMild or BicarbFallOrLowMild or LactateRiseOrHighMild or LacticAcidosisMild locate in acidbase;

Identify AcidosisOrBicarbFallorLoworLactateMod as AcidosisMod or BicarbFallOrLowMod or LactateRiseOrHighMod or LacticAcidosisMod locate in acidbase;

Identify AcidosisOrBicarbFallorLoworLactateSevere as AcidosisSevere or BicarbFallOrLowSevere or LactateRiseOrHighSevere or LacticAcidosisSevere locate in acidbase;

Identify AcidosisOrBicarbFallorLoworLactateProfound as AcidosisProfound or BicarbFallOrLowProfound or LactateRiseOrHighProfound or LacticAcidosisProfound locate in acidbase;

---Fall or Low Calcium or Ionized Calcium

Identify FallorLowCalciumMarginal as CalciumFallMarginal or IonCalciumFallMarginal or CalciumLowMarginal or IonCalciumLowMarginal;

Identify FallorLowCalciumMild as CalciumFallMild or IonCalciumFallMild or CalciumLowMild or IonCalciumLowMild;

Identify FallorLowCalciumMod as CalciumFallModerate or IonCalciumFallModerate or CalciumLowModerate or IonCalciumLowMarginal;

Identify FallorLowCalciumSevere as CalciumFallSevere or IonCalciumFallSevere or CalciumLowMarginal or IonCalciumLowMarginal;

Identify FallorLowCalciumProfound as CalciumFallProfound or IonCalciumFallProfound or CalciumLowProfound or IonCalciumLowProfound;

--Haemostatic identify PlateletLowOrFallMarginal as PlateletsFallMarginal or PlateletsLowMarginal locate in haemostatic;

identify PlateletLowOrFallMild as PlateletsFallMild or PlateletsLowMild locate in haemostatic;

identify PlateletLowOrFallModerate as PlateletsFallModerate or PlateletsLowModerate locate in haemostatic;

identify PlateletLowOrFallSevere as PlateletsFallSevere or PlateletsLowSevere locate in haemostatic;

identify PlateletLowOrFallProfound as PlateletsFallProfound or PlateletsLowProfound locate in haemostatic;

---Pathophysiologic Divergence or Decoherence of Procalcitonin and Low temp identify PDProcalcitoninLowTempMarginal as ProcalcitoninRiseOrHighMarginal and TemperatureFLow within 1d locate in acidbase, inflammatory;

identify PDProcalcitoninLowTempMild as ProcalcitoninRiseOrHighMild and TemperatureFLow within 1d locate in acidbase, inflammatory;

identify PDProcalcitoninLowTempMod as ProcalcitoninRiseOrHighMod and TemperatureFLow within 1d locate in acidbase, inflammatory;

identify PDProcalcitoninLowTempSevere as ProcalcitoninRiseOrHighSevere and TemperatureFLow within 1d locate in acidbase, inflammatory;

identify PDProcalcitoninLowTempProfound as ProcalcitoninRiseOrHighProfound and TemperatureFLow within 1d locate in acidbase, inflammatory;

-- Pathophysiologic Divergence or Decoherence Inflammation, Temperature

Identify PDNeutrophilOrBandsTempMarginal as NeutrophilOrBandOrTempMarginal and TemperatureFLowMarginal within 1d Locate in inflammatory;

Identify PDNeutrophilOrBandsTempMild as NeutrophilOrBandOrTempMild and TemperatureFLowMild within 1d Locate in inflammatory;

Identify PDNeutrophilOrBandsTempMod as NeutrophilOrBandOrTempMod and TemperatureFLowModerate within 1d Locate in inflammatory;

Identify PDNeutrophilOrBandsTempSevere as NeutrophilOrBandOrTempSevere and TemperatureFLowSevere within 1d Locate in inflammatory;

Identify PDNeutrophilOrBandsTempProfound as NeutrophilOrBandOrTempProfound and TemperatureFLowProfound within 1d Locate in inflammatory;

Identify PDNeutrophilAndBandsTempMarginal as NeutrophilAndBandAndTempMarginal and TemperatureFLowMarginal within 1d Locate in inflammatory;

Identify PDNeutrophilAndBandsTempMild as NeutrophilAndBandAndTempMild and TemperatureFLowMild within 1d Locate in inflammatory;

Identify PDNeutrophilAndBandsTempMod as NeutrophilAndBandAndTempMod and TemperatureFLowModerate within 1d Locate in inflammatory;

Identify PDNeutrophilAndBandsTempSevere as NeutrophilAndBandAndTempSevere and TemperatureFLowSevere within 1d Locate in inflammatory;

Identify PDNeutrophilAndBandsTempProfound as NeutrophilAndBandAndTempProfound and TemperatureFLowProfound within 1d Locate in inflammatory;

---Inflammatory Augmentation

Identify InflammatoryAugmentationMild as

NeutrophilOrBandOrTempMild or

NeutrophilAndBandsHighOrRiseMild or

PDLymphocytesAbsBandsMild or

PDLymphocytesAbsNeutrophilsAbsMild or

NeutrophilOrBandOrTempProcalcitoninMild or

PDProcalcitoninLowTempMild locate in inflammatory;

Identify InflammatoryAugmentationMod as

NeutrophilOrBandOrTempMod or

NeutrophilAndBandsHighOrRiseMod or

PDLymphocytesAbsBandsMod or

PDLymphocytesAbsNeutrophilsAbsMod or

NeutrophilOrBandOrTempProcalcitoninMod or

PDProcalcitoninLowTempMod or

PDNeutrophilOrBandsTempMarginal or

PDNeutrophilAndBandsTempMarginal or

PDNeutrophilOrBandsTempMild or

PDNeutrophilAndBandsTempMild or

PDNeutrophilOrBandsTempMod or

PDNeutrophilAndBandsTempMod or

NeutrophilFailureMarginal or

NeutrophilFailureMild or

NeutrophilFailureMod locate in inflammatory;

Identify InflammatoryAugmentationMarginal as

NeutrophilOrBandOrTempMarginal or

NeutrophilAndBandsHighOrRiseMarginal or

PDLymphocytesAbsBandsMarginal or

PDLymphocytesAbsNeutrophilsAbsMarginal or

NeutrophilOrBandOrTempProcalcitonMarginal or

PDProcalcitoninLowTempMarginal

Locate in inflammatory;

Identify InflammatoryAugmentationSevere as

NeutrophilOrBandOrTempSevere or

NeutrophilAndBandsHighOrRiseSevere or

PDLymphocytesAbsBandsSevere or

PDLymphocytesAbsNeutrophilsAbsSevere or

NeutrophilOrBandOrTempProcalcitoninSevere or

PDProcalcitoninLowTempSevere or

PDNeutrophilOrBandsTempSevere or

PDNeutrophilAndBandsTempSevere or

NeutrophilFailureSevere locate in inflammatory;

Identify InflammatoryAugmentationProfound as

NeutrophilOrBandOrTempProfound or

NeutrophilAndBandsHighOrRiseProfound or

PDLymphocytesAbsBandsProfound or

PDLymphocytesAbsNeutrophilsAbsProfound or

NeutrophilOrBandOrTempProcalcitonProfound or

PDProcalcitoninLowTempMarginal or

PDNeutrophilOrBandsTempProfound or

PDNeutrophilAndBandsTempProfound or

NeutrophilFailureProfound locate in inflammatory;

--Inflammation and Haemostatic identify SeqInflammatoryAugmentationPlateletFallMild as InflammatoryAugmentationMild preceding PlateletsFallMild within 1d locate in inflammatory, haemostatic;

identify SeqInflammatoryAugmentationPlateletFallMod as InflammatoryAugmentationMod preceding PlateletsFallModerate within 1d locate in inflammatory, haemostatic;

identify SeqInflammatoryAugmentationPlateletFallSevere as InflammatoryAugmentationSevere preceding PlateletsFallSevere within 1d locate in inflammatory, haemostatic;

identify SeqInflammatoryAugmentationPlateletFallProfound as InflammatoryAugmentationProfound preceding PlateletsFallProfound within 1d locate in inflammatory, haemostatic;

identify InflammatoryAugmentationPlateletLowOrFallMarginal as InflammatoryAugmentationMarginal and PlateletsFallMarginal within 1d locate in inflammatory, haemostatic;

identify InflammatoryAugmentationPlateletLowOrFallMild as InflammatoryAugmentationMild and PlateletsFallMild within 1d locate in inflammatory, haemostatic;

identify InflammatoryAugmentationPlateletLowOrFallMod as InflammatoryAugmentationMod and PlateletsFallModerate within 1d locate in inflammatory, haemostatic;

identify InflammatoryAugmentationPlateletLowOrFallSevere as InflammatoryAugmentationSevere and PlateletsFallSevere within 1d locate in inflammatory, haemostatic;

identify InflammatoryAugmentationPlateletLowOrFallProfound as InflammatoryAugmentationProfound and PlateletsFallProfound within 1d locate in inflammatory, haemostatic;

--Inflammation and Acid Base identify SeqInflammationAndAcidosisMarginal as InflammatoryAugmentationMarginal preceding AcidosisMarginal within 1d locate in inflammatory, acidbase;

identify SeqInflammationAndAcidosisMild as InflammatoryAugmentationMild preceding AcidosisMild within 1d locate in inflammatory, acidbase;

identify SeqInflammationAndAcidosisModerate as InflammatoryAugmentationMod preceding AcidosisMod within 1d locate in inflammatory, acidbase;

identify SeqInflammationAndAcidosisSevere as InflammatoryAugmentationSevere preceding AcidosisSevere within 1d locate in inflammatory, acidbase;

identify SeqInflammationAndAcidosisProfound as InflammatoryAugmentationProfound preceding AcidosisProfound within 1d locate in inflammatory, acidbase;

identify InflammationAndAcidosisMarginal as InflammatoryAugmentationMarginal and AcidosisMarginal within 1d locate in inflammatory, acidbase;

identify InflammationAndAcidosisMild as InflammatoryAugmentationMild and AcidosisMild within 1d locate in inflammatory, acidbase;

identify InflammationAndAcidosisMod as InflammatoryAugmentationMod and AcidosisMod within 1d locate in inflammatory, acidbase;

identify InflammationAndAcidosisSevere as InflammatoryAugmentationSevere and AcidosisSevere within 1d locate in inflammatory, acidbase;

identify InflammationAndAcidosisProfound as InflammatoryAugmentationProfound and AcidosisProfound within 1d locate in inflammatory, acidbase;

--Inflammation and Metabolic

Identify InflammationAndAlbuminFallMarginal as InflammatoryAugmentationMarginal and AlbuminFallMarginal within 2d locate in inflammatory, metabolic;

Identify InflammationAndAlbuminFallMild as InflammatoryAugmentationMild and AlbuminFallMild within 2d locate in inflammatory, metabolic;

Identify InflammationAndAlbuminFallMod as InflammatoryAugmentationMod and AlbuminFallModerate within 2d locate in inflammatory, metabolic;

Identify InflammationAndAlbuminFallSevere as InflammatoryAugmentationSevere and AlbuminFallSevere within 2d locate in inflammatory, metabolic;

Identify InflammationAndAlbuminFallProfound as InflammatoryAugmentationProfound and AlbuminFallProfound within 2d locate in inflammatory, metabolic;

Identify SeqInflammationAndAlbuminFallMarginal as InflammatoryAugmentationMarginal preceding AlbuminFallMarginal within 2d locate in inflammatory, metabolic;

Identify SeqInflammationAndAlbuminFallMild as InflammatoryAugmentationMild preceding AlbuminFallMild within 2d locate in inflammatory, metabolic;

Identify SeqInflammationAndAlbuminFallMod as InflammatoryAugmentationMod preceding AlbuminFallModerate within 2d locate in inflammatory, metabolic;

Identify SeqInflammationAndAlbuminFallSevere as InflammatoryAugmentationSevere preceding AlbuminFallSevere within 2d locate in inflammatory, metabolic;

Identify SeqInflammationAndAlbuminFallProfound as InflammatoryAugmentationProfound preceding AlbuminFallProfound within 2d locate in inflammatory, metabolic;

--Haemostatic and Procalcitonin identify SeqProcalcitoninPlateletFallMarginal as ProcalcitoninRiseOrHighMarginal preceding PlateletsFallMarginal within 1d locate in inflammatory, haemostatic;

identify SeqInflammationPlateletFallMild as ProcalcitoninRiseOrHighMild preceding PlateletsFallMild within 1d locate in inflammatory, haemostatic;

identify SeqProcalcitoninPlateletFallMod as ProcalcitoninRiseOrHighMod preceding PlateletsFallModerate within 1d locate in inflammatory, haemostatic;

identify SeqProcalcitoninPlateletFallSevere as ProcalcitoninRiseOrHighSevere preceding PlateletsFallSevere within 1d locate in inflammatory, haemostatic;

identify SeqProcalcitoninPlateletFallProfound as ProcalcitoninRiseOrHighProfound preceding PlateletsFallProfound within 1d locate in inflammatory, haemostatic;

identify ProcalcitoninPlateletLowOrFallMarginal as ProcalcitoninRiseOrHighMarginal and PlateletsFallMarginal within 1d locate in inflammatory, haemostatic;

identify ProcalcitoninPlateletLowOrFallMild as ProcalcitoninRiseOrHighMild and PlateletsFallMild within 1d locate in inflammatory, haemostatic;

identify ProcalcitoninPlateletLowOrFallMod as ProcalcitoninRiseOrHighMod and PlateletsFallModerate within 1d locate in inflammatory, haemostatic;

identify ProcalcitoninPlateletLowOrFallSevere as ProcalcitoninRiseOrHighSevere and PlateletsFallSevere within 1d locate in inflammatory, haemostatic;

identify ProcalcitoninPlateletLowOrFallProfound as ProcalcitoninRiseOrHighProfound and PlateletsFallProfound within 1d locate in inflammatory, haemostatic;

--Acid Base and Procalcitonin identify SeqProcalcitoninAcidosisMarginal as ProcalcitoninRiseOrHighMarginal preceding AcidosisMarginal within 1d locate in acidbase, inflammatory;

identify SeqProcalcitoninAcidosisMild as ProcalcitoninRiseOrHighMild preceding AcidosisMarginal within 1d locate in acidbase, inflammatory;

identify SeqProcalcitoninAcidosisMod as ProcalcitoninRiseOrHighMod preceding AcidosisMod within 1d locate in acidbase, inflammatory;

identify SeqProcalcitoninAcidosisSevere as ProcalcitoninRiseOrHighSevere preceding AcidosisSevere within 1d locate in acidbase, inflammatory;

identify SeqProcalcitoninAcidosisProfound as ProcalcitoninRiseOrHighProfound preceding AcidosisProfound within 1d locate in acidbase, inflammatory;

identify ProcalcitoninAcidosisMarginal as ProcalcitoninRiseOrHighMarginal and AcidosisMarginal within 1d locate in acidbase, inflammatory;

identify ProcalcitoninAcidosisMild as ProcalcitoninRiseOrHighMild and AcidosisMild within 1d locate in acidbase, inflammatory;

identify ProcalcitoninAcidosisMod as ProcalcitoninRiseOrHighMod and AcidosisMod within 1d locate in acidbase, inflammatory;

identify ProcalcitoninAcidosisSevere as ProcalcitoninRiseOrHighSevere and AcidosisSevere within 1d locate in acidbase, inflammatory;

identify ProcalcitoninAcidosisProfound as ProcalcitoninRiseOrHighProfound and AcidosisProfound within 1d locate in acidbase, inflammatory;

identify SeqProcalcitoninLactateMarginal as ProcalcitoninRiseOrHighMarginal preceding LactateRiseOrHighMarginal within 1d locate in acidbase, inflammatory;

identify SeqProcalcitoninLactateMild as ProcalcitoninRiseOrHighMild preceding LactateRiseOrHighMarginal within 1d locate in acidbase, inflammatory;

identify SeqProcalcitoninLactateMod as ProcalcitoninRiseOrHighMod preceding LactateRiseOrHighMod within 1d locate in acidbase, inflammatory;

identify SeqProcalcitoninLactateSevere as ProcalcitoninRiseOrHighSevere preceding LactateRiseOrHighSevere within 1d locate in acidbase, inflammatory;

identify SeqProcalcitoninLactateProfound as ProcalcitoninRiseOrHighProfound preceding LactateRiseOrHighProfound within 1d locate in acidbase, inflammatory;

identify ProcalcitoninLactateMarginal as ProcalcitoninRiseOrHighMarginal and LactateRiseOrHighMarginal within 1d locate in acidbase, inflammatory;

identify ProcalcitoninLactateMild as ProcalcitoninRiseOrHighMild and LactateRiseOrHighMild within 1d locate in acidbase, inflammatory;

identify ProcalcitoninLactateMod as ProcalcitoninRiseOrHighMod and LactateRiseOrHighMod within 1d locate in acidbase, inflammatory;

identify ProcalcitoninLactateSevere as ProcalcitoninRiseOrHighSevere and LactateRiseOrHighSevere within 1d locate in acidbase, inflammatory;

identify ProcalcitoninLactateProfound as ProcalcitoninRiseOrHighProfound and LactateRiseOrHighProfound within 1d locate in acidbase, inflammatory;

identify ProcalcitoninBicarbFallMarginal as ProcalcitoninRiseOrHighMarginal and BicarbFallMarginal within 1d locate in acidbase, inflammatory;

identify ProcalcitoninBicarbFallMild as ProcalcitoninRiseOrHighMild and BicarbFallMild within 1d locate in acidbase, inflammatory;

identify ProcalcitoninBicarbFallMod as ProcalcitoninRiseOrHighMod and BicarbFallModerate within 1d locate in acidbase, inflammatory;

identify ProcalcitoninBicarbFallSevere as ProcalcitoninRiseOrHighSevere and BicarbFallSevere within 1d locate in acidbase, inflammatory;

identify ProcalcitoninBicarbFallProfound as ProcalcitoninRiseOrHighProfound and BicarbFallProfound within 1d locate in acidbase, inflammatory;

identify SeqProcalcitoninBicarbFallMarginal as ProcalcitoninRiseOrHighMarginal preceding BicarbFallMarginal within 1d locate in acidbase, inflammatory;

identify SeqProcalcitoninFallOrLowBicarbMild as ProcalcitoninRiseOrHighMild preceding BicarbFallMild within 1d locate in acidbase, inflammatory;

identify SeqProcalcitoninBicarbFallMod as ProcalcitoninRiseOrHighMod preceding BicarbFallModerate within 1d locate in acidbase, inflammatory;

identify SeqProcalcitoninBicarbFallSevere as ProcalcitoninRiseOrHighSevere preceding BicarbFallSevere within 1d locate in acidbase, inflammatory;

identify SeqProcalcitoninBicarbFallProfound as ProcalcitoninRiseOrHighProfound preceding BicarbFallProfound within 1d locate in acidbase, inflammatory;

identify ProcalcitoninFallOrLowBicarbMarginal as ProcalcitoninRiseOrHighMarginal and BicarbFallOrLowMarginal within 1d locate in acidbase, inflammatory;

identify ProcalcitoninFallOrLowBicarbMild as ProcalcitoninRiseOrHighMild and BicarbFallOrLowMild within 1d locate in acidbase, inflammatory;

identify ProcalcitoninFallOrLowBicarbMod as ProcalcitoninRiseOrHighMod and BicarbFallOrLowMod within 1d locate in acidbase, inflammatory;

identify ProcalcitoninFallOrLowBicarbSevere as ProcalcitoninRiseOrHighSevere and BicarbFallOrLowSevere within 1d locate in acidbase, inflammatory;

identify ProcalcitoninFallOrLowBicarbProfound as ProcalcitoninRiseOrHighProfound and BicarbFallOrLowProfound within 1d locate in acidbase, inflammatory;

--Cardiac

Identify HRHighOrRiseMarginal as HRHighMarginal or HRRiseMarginal Locate in cardiac;

Identify HRHighOrRiseMild as HRHighMild or HRRiseMild Locate in cardiac;

Identify HRHighOrRiseMod as HRHighModerate or HRRiseModerate Locate in cardiac;

Identify HRHighOrRiseSevere as HRHighSevere or HRRiseSevere Locate in cardiac;

Identify HRHighOrRiseProfound as HRHighProfound or HRRiseProfound Locate in cardiac;

Identify BpSystolicLowOrFallMarginal as BpSystolicLowMarginal or BpSystolicFallMarginal Locate in Cardiac;

Identify BpSystolicLowOrFallMild as BpSystolicLowMild or BpSystolicFallMild Locate in Cardiac;

Identify BpSystolicLowOrFallMod as BpSystolicLowModerate or BpSystolicFallModerate Locate in Cardiac;

Identify BpSystolicLowOrFallSevere as BpSystolicLowSevere or BpSystolicFallSevere Locate in Cardiac;

Identify BpSystolicLowOrFallProfound as BpSystolicLowProfound or BpSystolicFallProfound Locate in Cardiac;

Identify PDHRandBpSystolicMarginal as HRHighOrRiseMarginal and BpSystolicLowOrFallMarginal within 1d Locate in cardiac;

Identify PDHRandBpSystolicMild as HRHighOrRiseMild and BpSystolicLowOrFallMild within 1d Locate in cardiac;

Identify PDHRandBpSystolicMod as HRHighOrRiseMod and BpSystolicLowOrFallMod within 1d Locate in cardiac;

Identify PDHRandBpSystolicSevere as HRHighOrRiseSevere and BpSystolicLowOrFallSevere within 1d Locate in cardiac;

Identify PDHRandBpSystolicProfound as HRHighOrRiseProfound and BpSystolicLowOrFallProfound within 1d Locate in cardiac;

--Cardiac/Respiratory

Identify SPO2HRMild as HRHighOrRiseMarginal and SaO2LowOrFallMarginal within 1d Locate in respiratory;

Identify SPO2HRMild_duplicated as HRHighOrRiseMild and SaO2LowOrFallMild within 1d Locate in respiratory;

Identify SPO2HRMod as HRHighOrRiseMod and SaO2LowOrFallMod within 1d Locate in respiratory;

Identify SPO2HRSevere as HRHighOrRiseSevere and SaO2LowOrFallSevere within 1d Locate in respiratory;

Identify SPO2HRProfound as HRHighOrRiseProfound and SaO2LowOrFallProfound within 1d Locate in respiratory;

-- Temp/Cardiac/Respiratory/Inflammation CONV Convergence or Coherence

Identify CONVHighHRRRMarginal as HRHighMarginal and RespiratoryRateHighMarginal within 1d Locate in respiratory, cardiac;

Identify CONVHighHRRRMild as HRHighMild and RespiratoryRateHighMild within 1d Locate in respiratory, cardiac;

Identify CONVHighHRRRMod as HRHighModerate and RespiratoryRateHighModerate within 1d Locate in respiratory, cardiac;

Identify CONVHighHRRRSevere as HRHighSevere and RespiratoryRateHighSevere within 1d Locate in respiratory, cardiac;

Identify CONVHighHRRRProfound as HRHighProfound and RespiratoryRateHighProfound within 1d Locate in respiratory, cardiac;

Identify CONVHighHRtempRRMarginal as CONVHighHRRRMarginal and TemperatureFHighMarginal within 1d Locate in respiratory, cardiac, inflammatory;

Identify CONVHighHRtempRRMild as CONVHighHRRRMild and TemperatureFHighMild within 1d Locate in respiratory, cardiac, inflammatory;

Identify CONVHighHRtempRRMod as CONVHighHRRRMod and TemperatureFHighModerate and RespiratoryRateHighModerate within 1d Locate in respiratory, cardiac, inflammatory;

Identify CONVHighHRtempRRSevere as CONVHighHRRRSevere and TemperatureFHighSevere and RespiratoryRateHighSevere within 1d Locate in respiratory, cardiac, inflammatory;

Identify CONVHighHRtempRRProfound as CONVHighHRRRProfound and TemperatureFHighProfound and RespiratoryRateHighProfound within 1d Locate in respiratory, cardiac, inflammatory;

Identify CONVHighHRtempRRInflammationMarginal as CONVHighHRtempRRMarginal and InflammatoryAugmentationMarginal within 1d Locate in respiratory, cardiac, inflammatory;

Identify CONVHighHRtempRRInflammationMild as CONVHighHRtempRRMild and InflammatoryAugmentationMild within 1d Locate in respiratory, cardiac, inflammatory;

Identify CONVHighHRtempRRInflammationMod as CONVHighHRtempRRMod and InflammatoryAugmentationMod within 1d Locate in respiratory, cardiac, inflammatory;

Identify CONVHighHRtempRRInflammationSevere as CONVHighHRtempRRSevere and InflammatoryAugmentationSevere within 1d Locate in respiratory, cardiac, inflammatory;

Identify CONVHighHRtempRRInflammationProfound as CONVHighHRtempRRProfound and InflammatoryAugmentationProfound within 1d Locate in respiratory, cardiac, inflammatory;

Identify CONVHighHRtempRRInflammationCumMarginal as CONVHighHRtempRRMarginal and NeutrophilAndBandAndTempMarginal within 1d Locate in respiratory, cardiac, inflammatory;

Identify CONVHighHRtempRRInflammationCumMild as CONVHighHRtempRRMild and NeutrophilAndBandAndTempMild within 1d Locate in respiratory, cardiac, inflammatory;

Identify CONVHighHRtempRRInflammationCumMod as CONVHighHRtempRRMod and NeutrophilAndBandAndTempMod within 1d Locate in respiratory, cardiac, inflammatory;

Identify CONVHighHRtempRRInflammationCumSevere as CONVHighHRtempRRSevere and NeutrophilAndBandAndTempSevere within 1d Locate in respiratory, cardiac, inflammatory;

Identify CONVHighHRtempRRInflammationCumProfound as CONVHighHRtempRRProfound and NeutrophilAndBandAndTempProfound within 1d Locate in respiratory, cardiac, inflammatory;

Identify PDHHighHRRRBpLowOrFallSystolicMarginal as CONVHighHRRRMarginal and BpSystolicLowOrFallMarginal within 1d Locate in respiratory, cardiac;

Identify PDHHighHRRRBpLowOrFallSystolicMild as CONVHighHRRRMild and BpSystolicLowOrFallMild within 1d Locate in respiratory, cardiac;

Identify PDHHighHRRRBpLowOrFallSystolicModerate as CONVHighHRRRMod and BpSystolicLowOrFallMod within 1d Locate in respiratory, cardiac;

Identify PDHHighHRRRBpLowOrFallSystolicSevere as CONVHighHRRRSevere and BpSystolicLowOrFallSevere within 1d Locate in respiratory, cardiac;

Identify PDHHighHRRRBpLowOrFallSystolicProfound as CONVHighHRRRProfound and BpSystolicLowOrFallProfound within 1d Locate in respiratory, cardiac;

Identify PDHighHRtempRRInflammationlowBPMarginal as CONVHighHRtempRRInflammationMarginal and BpSystolicLowOrFallMarginal within 1d Locate in respiratory, cardiac,inflammatory;

Identify PDHighHRtempRRInflammationlowBPMild as CONVHighHRtempRRInflammationMild and BpSystolicLowOrFallMild within 1d Locate in respiratory, cardiac,inflammatory;

Identify PDHighHRtempRRInflammationlowBPMod as CONVHighHRtempRRInflammationMod and BpSystolicLowOrFallMod within 1d Locate in respiratory, cardiac,inflammatory;

Identify PDHighHRtempRRInflammationlowBPSevere as CONVHighHRtempRRInflammationSevere and BpSystolicLowOrFallSevere within 1d Locate in respiratory, cardiac,inflammatory;

Identify PDHighHRtempRRInflammationlowBPProfound as CONVHighHRtempRRInflammationProfound and BpSystolicLowOrFallProfound within 1d Locate in respiratory, cardiac,inflammatory;

---Pathophysiologic Divergence or Decoherence of Acidosis, SPO2

Identify PDAcidosisSaO2Marginal as AcidosisMarginal and SaO2LowOrFallMarginal within 1d Locate in respiratory, acidbase;

Identify PDAcidosisSaO2Mild as AcidosisMild and SaO2LowOrFallMild within 1d Locate in respiratory, acidbase;

Identify PDAcidosisSaO2Mod as AcidosisMod and SaO2LowOrFallMod within 1d Locate in respiratory, acidbase;

Identify PDAcidosisSaO2Severe as AcidosisSevere and SaO2LowOrFallSevere within 1d Locate in respiratory, acidbase;

Identify PDAcidosisSaO2Profound as AcidosisProfound and SaO2LowOrFallProfound within 1d Locate in respiratory, acidbase;

Identify PDLactateSaO2Marginal as LactateRiseOrHighMarginal and SaO2LowOrFallMarginal within 1d Locate in respiratory, acidbase;

Identify PDLactateSaO2Mild as LactateRiseOrHighMild and SaO2LowOrFallMild within 1d Locate in respiratory, acidbase;

Identify PDLactateSaO2Mod as LactateRiseOrHighMod and SaO2LowOrFallMod within 1d Locate in respiratory, acidbase;

Identify PDLactateSaO2Severe as LactateRiseOrHighSevere and SaO2LowOrFallSevere within 1d Locate in respiratory, acidbase;

Identify PDLactateSaO2Profound as LactateRiseOrHighProfound and SaO2LowOrFallProfound within 1d Locate in respiratory, acidbase;

Identify CONVAcidosisRRMarginal as AcidosisMarginal and RespiratoryRateHighMarginal within 1d Locate in respiratory, cardiac;

Identify CONVAcidosisRRMild as AcidosisMild and RespiratoryRateHighMild within 1d Locate in respiratory, cardiac;

Identify CONVAcidosisRRMod as AcidosisMod and RespiratoryRateHighModerate within 1d Locate in respiratory, cardiac;

Identify CONVAcidosisRRSevere as AcidosisSevere and RespiratoryRateHighSevere within 1d Locate in respiratory, cardiac;

Identify CONVAcidosisRRProfound as AcidosisProfound and RespiratoryRateHighProfound within 1d Locate in respiratory, cardiac;

Identify PDAcidosisOrLactateSaO2Marginal as PDAcidosisSaO2Marginal or PDLactateSaO2Marginal locate in respiratory, acidbase;

Identify PDAcidosisOrLactateSaO2Mild as PDAcidosisSaO2Mild or PDLactateSaO2Mild locate in respiratory, acidbase;

Identify PDAcidosisOrLactateSaO2Mod as PDAcidosisSaO2Mod or PDLactateSaO2Mod locate in respiratory, acidbase;

Identify PDAcidosisOrLactateSaO2Severe as PDAcidosisSaO2Severe or PDLactateSaO2Severe locate in respiratory, acidbase;

Identify PDAcidosisOrLactateSaO2Profound as PDAcidosisSaO2Profound or PDLactateSaO2Profound locate in respiratory, acidbase;

--- Pathophysiologic Divergence or Decoherence of Acidosis, BP

Identify PDAcidosisLowOrFallBP as AcidosisMarginal and BpSystolicLowOrFallMarginal within 1d Locate in acidbase, cardiac;

Identify PDAcidosisLowOrFallBP_Duplicated as AcidosisMild and BpSystolicLowOrFallMild within 1d Locate in acidbase, cardiac;

Identify PDAcidosisLowOrFallBP_Duplicated2 as AcidosisMod and BpSystolicLowOrFallMod within 1d Locate in acidbase, cardiac;

Identify PDAcidosisLowOrFallBP_Duplicated3 as AcidosisSevere and BpSystolicLowOrFallSevere within 1d Locate in acidbase, cardiac;

Identify PDAcidosisLowOrFallBP_Duplicated4 as AcidosisProfound and BpSystolicLowOrFallProfound within 1d Locate in acidbase, cardiac;

Identify PDAcidosisSPO2InflammationMarginal as PDAcidosisSaO2Marginal and InflammatoryAugmentationMarginal within 1d Locate in acidbase, respiratory, inflammatory;

Identify PDAcidosisSPO2InflammationMild as PDAcidosisSaO2Mild and InflammatoryAugmentationMild within 1d Locate in acidbase, respiratory, inflammatory;

Identify PDAcidosisSPO2InflammationMod as PDAcidosisSaO2Mod and InflammatoryAugmentationMod within 1d Locate in acidbase, respiratory, inflammatory;

Identify PDAcidosisSPO2InflammationSevere as PDAcidosisSaO2Severe and InflammatoryAugmentationSevere within 1d Locate in acidbase, respiratory, inflammatory;

Identify PDAcidosisSPO2InflammationProfound as PDAcidosisSaO2Profound and InflammatoryAugmentationProfound within 1d Locate in acidbase, respiratory, inflammatory;

Identify PDAcidosisSPO2InflammationCumMarginal as PDAcidosisSaO2Marginal and NeutrophilAndBandAndTempMarginal within 1d Locate in acidbase, respiratory, inflammatory;

Identify PDAcidosisSPO2InflammationCumMild as PDAcidosisSaO2Mild and NeutrophilAndBandAndTempMild within 1d Locate in acidbase, respiratory, inflammatory;

Identify PDAcidosisSPO2InflammationCumMod as PDAcidosisSaO2Mod and NeutrophilAndBandAndTempMod within 1d Locate in acidbase, respiratory, inflammatory;

Identify PDAcidosisSPO2InflammationCumSevere as PDAcidosisSaO2Severe and NeutrophilAndBandAndTempSevere within 1d Locate in acidbase, respiratory, inflammatory;

Identify PDAcidosisSPO2InflammationCumProfound as PDAcidosisSaO2Profound and NeutrophilAndBandAndTempProfound within 1d Locate in acidbase, respiratory, inflammatory;

Identify PDLactateSPO2InflammationMarginal as PDLactateSaO2Marginal and InflammatoryAugmentationMarginal within 1d Locate in acidbase, respiratory, inflammatory;

Identify PDLactateSPO2InflammationMild as PDLactateSaO2Mild and InflammatoryAugmentationMild within 1d Locate in acidbase, respiratory, inflammatory;

Identify PDLactateSPO2InflammationMod as PDLactateSaO2Mod and InflammatoryAugmentationMod within 1d Locate in acidbase, respiratory, inflammatory;

Identify PDLactateSPO2InflammationSevere as PDLactateSaO2Severe and InflammatoryAugmentationSevere within 1d Locate in acidbase, respiratory, inflammatory;

Identify PDLactateSPO2InflammationProfound as PDLactateSaO2Profound and InflammatoryAugmentationProfound within 1d Locate in acidbase, respiratory, inflammatory;

Identify PDLactateSPO2InflammationCumMarginal as PDLactateSaO2Marginal and NeutrophilAndBandAndTempMarginal within 1d Locate in acidbase, respiratory, inflammatory;

Identify PDLactateSPO2InflammationCumMild as PDLactateSaO2Mild and NeutrophilAndBandAndTempMild within 1d Locate in acidbase, respiratory, inflammatory;

Identify PDLactateSPO2InflammationCumMod as PDLactateSaO2Mod and NeutrophilAndBandAndTempMod within 1d Locate in acidbase, respiratory, inflammatory;

Identify PDLactateSPO2InflammationCumSevere as PDLactateSaO2Severe and NeutrophilAndBandAndTempSevere within 1d Locate in acidbase, respiratory, inflammatory;

Identify PDLactateSPO2InflammationCumProfound as PDLactateSaO2Profound and NeutrophilAndBandAndTempProfound within 1d Locate in acidbase, respiratory, inflammatory;

Identify HRHighorRRHighMarginal as HRHighMarginal or RespiratoryRateHighMarginal Locate in respiratory, cardiac;

Identify HRHighorRRHighMild as HRHighMild or RespiratoryRateHighMild Locate in respiratory, cardiac;

Identify HRHighorRRHighMod as HRHighModerate or RespiratoryRateHighModerate Locate in respiratory, cardiac;

Identify HRHighorRRHighSevere as HRHighSevere or RespiratoryRateHighSevere Locate in respiratory, cardiac;

Identify HRHighorRRHighProfound as HRHighProfound or RespiratoryRateHighProfound Locate in respiratory, cardiac;

---Renal Failure identify CreatinineRiseOrHighMarginal as CreatinineRiseMarginal or CreatinineHighMarginal locate in renal;

identify CreatinineRiseOrHighMild as CreatinineRiseMild or CreatinineHighMild locate in renal;

identify CreatinineRiseOrHighMod as CreatinineRiseModerate or CreatinineHighModerate locate in renal;

identify CreatinineRiseOrHighSevere as CreatinineRiseSevere or CreatinineHighSevere locate in renal;

identify CreatinineRiseOrHighProfound as CreatinineRiseProfound or CreatinineHighProfound locate in renal;

---SIRS

Identify SIRSMarginal as InflammatoryAugmentationMarginal and HRHighorRRHighMarginal within 1d locate in inflammatory;

Identify SIRSMild as InflammatoryAugmentationMild and HRHighorRRHighMild within 1d locate in inflammatory;

Identify SIRSMod as InflammatoryAugmentationMod and HRHighorRRHighMod within 1d locate in inflammatory;

Identify SIRSSevere as InflammatoryAugmentationSevere and HRHighorRRHighSevere within 1d locate in inflammatory;

Identify SIRSProfound as InflammatoryAugmentationProfound and HRHighorRRHighProfound within 1d locate in inflammatory;

--- InflammatoryAugmentation and increase or high Acid

Identify InflammatoryAugmentationandAcidMarginal as InflammatoryAugmentationMarginal and AcidosisOrBicarbFallorLoworLactateMarginal within 1d locate in inflammatory, acidbase;

Identify InflammatoryAugmentationandAcidMild as SIRSMild and InflammatoryAugmentationMild within 1d locate in inflammatory, acidbase;

Identify InflammatoryAugmentationandAcidMod as SIRSMod and InflammatoryAugmentationMod within 1d locate in inflammatory, acidbase;

Identify InflammatoryAugmentationandAcidSevere as SIRSSevere and InflammatoryAugmentationSevere within 1d locate in inflammatory, acidbase;

Identify InflammatoryAugmentationandAcidProfound as SIRSProfound and InflammatoryAugmentationProfound within 1d locate in inflammatory, acidbase;

--- InflammatoryAugmentation and low or fall Platelets

Identify InflammatoryAugmentationandPlateletsLoworFallMarginal as InflammatoryAugmentationMarginal and PlateletLowOrFallMarginal within 1d locate in inflammatory, acidbase;

Identify InflammatoryAugmentationandPlateletsLoworFallMild as InflammatoryAugmentationMild and PlateletLowOrFallMild within 1d locate in inflammatory, acidbase;

Identify InflammatoryAugmentationandPlateletsLoworFallMod as InflammatoryAugmentationMod and PlateletLowOrFallModerate within 1d locate in inflammatory, acidbase;

Identify InflammatoryAugmentationandPlateletsLoworFallSevere as InflammatoryAugmentationSevere and PlateletLowOrFallSevere within 1d locate in inflammatory, acidbase;

Identify InflammatoryAugmentationandPlateletsLoworFallProfound as InflammatoryAugmentationProfound and PlateletLowOrFallSevere within 1d locate in inflammatory, acidbase;

--- InflammatoryAugmentation and low or fall Calcium

Identify InflammatoryAugmentationandCalciumMarginal as InflammatoryAugmentationMarginal and FallorLowCalciumMarginal within 1d locate in inflammatory, acidbase;

Identify InflammatoryAugmentationandCalciumMild as InflammatoryAugmentationMild and FallorLowCalciumMild within 1d locate in inflammatory, acidbase;

Identify InflammatoryAugmentationandCalciumMod as InflammatoryAugmentationMod and FallorLowCalciumMod within 1d locate in inflammatory, acidbase;

Identify InflammatoryAugmentationandCalciumSevere as InflammatoryAugmentationSevere and FallorLowCalciumSevere within 1d locate in inflammatory, acidbase;

Identify InflammatoryAugmentationandCalciumProfound as InflammatoryAugmentationProfound and FallorLowCalciumProfound within 1d locate in inflammatory, acidbase;

--- InflammatoryAugmentation and High or Rise Creatinine

Identify InflammatoryAugmentationandCreatinineMarginal as InflammatoryAugmentationMarginal and CreatinineRiseOrHighMarginal within 1d locate in inflammatory, Renal;

Identify InflammatoryAugmentationandCreatinineFailureMild as InflammatoryAugmentationMild and CreatinineRiseOrHighMild within 1d locate in inflammatory, Renal;

Identify InflammatoryAugmentationandCreatinineMod as InflammatoryAugmentationMod and CreatinineRiseOrHighMod within 1d locate in inflammatory, Renal;

Identify InflammatoryAugmentationandCreatinineSevere as InflammatoryAugmentationSevere and CreatinineRiseOrHighSevere within 1d locate in inflammatory, Renal;

Identify InflammatoryAugmentationandCreatinineProfound as InflammatoryAugmentationProfound and CreatinineRiseOrHighProfound within 1d locate in inflammatory, Renal;

--- InflammatoryAugmentation and Fall or Low Albumin

Identify InflammatoryAugmentationandAlbuminMarginal as InflammatoryAugmentationMarginal and AlbuminFallMarginal within 1d locate in inflammatory, Renal;

Identify InflammatoryAugmentationandAlbuminFailureMild as InflammatoryAugmentationMild and AlbuminFallMild within 1d locate in inflammatory, Renal;

Identify InflammatoryAugmentationandAlbuminMod as InflammatoryAugmentationMod and AlbuminFallModerate within 1d locate in inflammatory, Renal;

Identify InflammatoryAugmentationandAlbuminSevere as InflammatoryAugmentationSevere and AlbuminFallSevere within 1d locate in inflammatory, Renal;

Identify InflammatoryAugmentationandAlbuminProfound as
InflammatoryAugmentationProfound and AlbuminFallProfound within 1d locate in
inflammatory, Renal;

---SIRS and Acid

Identify SIRSandAcidMarginal as SIRSMarginal and
AcidosisOrBicarbFallorLoworLactateMarginal within 1d locate in inflammatory, acidbase;

Identify SIRSandAcidMild as SIRSMild and AcidosisOrBicarbFallorLoworLactateMild within
1d locate in inflammatory, acidbase;

Identify SIRSandAcidMod as SIRSMod and AcidosisOrBicarbFallorLoworLactateMod within
1d locate in inflammatory, acidbase;

Identify SIRSandAcidSevere as SIRSSevere and AcidosisOrBicarbFallorLoworLactateSevere
within 1d locate in inflammatory, acidbase;

Identify SIRSandAcidProfound as SIRSProfound and
AcidosisOrBicarbFallorLoworLactateProfound within 1d locate in inflammatory, acidbase;

--- SIRS and low or fall Platelets

Identify SIRSandPlateletsLoworFallMarginal as SIRSMarginal and PlateletLowOrFallMarginal
within 1d locate in inflammatory, acidbase;

Identify SIRSandPlateletsLoworFallMild as SIRSMild and PlateletLowOrFallMild within 1d
locate in inflammatory, acidbase;

Identify SIRSandPlateletsLoworFallMod as SIRSMod and PlateletLowOrFallModerate within
1d locate in inflammatory, acidbase;

Identify SIRSandPlateletsLoworFallSevere as SIRSSevere and PlateletLowOrFallSevere within
1d locate in inflammatory, acidbase;

Identify SIRSandPlateletsLoworFallProfound as SIRSProfound and PlateletLowOrFallProfound
within 1d locate in inflammatory, acidbase;

--- SIRS and low or fall Calcium

Identify SIRSandAcidMarginal_Duplicated as SIRSMarginal and FallorLowCalciumMarginal
within 1d locate in inflammatory, acidbase;

Identify SIRSandAcidMild_Duplicated as SIRSMild and FallorLowCalciumMild within 1d
locate in inflammatory, acidbase;

Identify SIRSandAcidMod_Duplicated as SIRSMod and FallorLowCalciumMod within 1d locate in inflammatory, acidbase;

Identify SIRSandAcidSevere_Duplicated as SIRSSevere and FallorLowCalciumSevere within 1d locate in inflammatory, acidbase;

Identify SIRSandAcidProfound_Duplicated as SIRSProfound and FallorLowCalciumProfound within 1d locate in inflammatory, acidbase;

--- SIRS and High or Rise Creatinine

Identify SIRSandCreatinineMarginal as SIRSMarginal and CreatinineRiseOrHighMarginal within 1d locate in inflammatory, Renal;

Identify SIRSandCreatinineMild as SIRSMild and CreatinineRiseOrHighMild within 1d locate in inflammatory, Renal;

Identify SIRSandCreatinineMod as SIRSMod and CreatinineRiseOrHighMod within 1d locate in inflammatory, Renal;

Identify SIRSandCreatinineSevere as SIRSSevere and CreatinineRiseOrHighSevere within 1d locate in inflammatory, Renal;

Identify SIRSandCreatinineProfound as SIRSProfound and CreatinineRiseOrHighProfound within 1d locate in inflammatory, Renal;

--- SIRS and Fall or Low Albumin

Identify SIRSandAlbuminMarginal as SIRSMarginal and AlbuminFallMarginal within 1d locate in inflammatory, Renal;

Identify SIRSandAlbuminFailureMild as SIRSMild and AlbuminFallMild within 1d locate in inflammatory, Renal;

Identify SIRSandAlbuminMod as SIRSMod and AlbuminFallModerate within 1d locate in inflammatory, Renal;

Identify SIRSandAlbuminSevere as SIRSSevere and AlbuminFallSevere within 1d locate in inflammatory, Renal;

Identify SIRSandAlbuminProfound as SIRSProfound and AlbuminFallProfound within 1d locate in inflammatory, Renal;

-- SIRS

Identify SIRSandPDAcidosisOrLactateSaO2Marginal as SIRSMarginal and PDAcidosisOrLactateSaO2Marginal within 1d locate in inflammatory, Respiratory;

Identify SIRSandPDAcidosisOrLactateSaO2Mild as SIRSMild and PDAcidosisOrLactateSaO2Mild within 1d locate in inflammatory, Respiratory;

Identify SIRSandPDAcidosisOrLactateSaO2Mod as SIRSMod and PDAcidosisOrLactateSaO2Mod within 1d locate in inflammatory, Respiratory;

Identify SIRSandPDAcidosisOrLactateSaO2Severe as SIRSSevere and PDAcidosisOrLactateSaO2Severe within 1d locate in inflammatory, Respiratory;

Identify SIRSandPDAcidosisOrLactateSaO2Profound as SIRSProfound and PDAcidosisOrLactateSaO2Profound within 1d locate in inflammatory, Respiratory;

Identify SIRSandPDSPO2RRMarginal as SIRSMarginal and PDSPO2RRMarginal within 1d locate in inflammatory, Respiratory;

Identify SIRSandPDSPO2RRMild as SIRSMild and PDSPO2RRMild within 1d locate in inflammatory, Respiratory;

Identify SIRSandPDSPO2RRMod as SIRSMod and PDSPO2RRMod within 1d locate in inflammatory, Respiratory;

Identify SIRSandPDSPO2RRSevere as SIRSSevere and PDSPO2RRSevere within 1d locate in inflammatory, Respiratory;

Identify SIRSandPDSPO2RRProfound as SIRSProfound and PDSPO2RRProfound within 1d locate in inflammatory, Respiratory;

--Identify SIRS and Respiratory Failure

Identify SIRSandRespFailureMarginal as SIRSandPDAcidosisOrLactateSaO2Marginal or SIRSandPDSPO2RRMarginal locate in inflammatory, Respiratory;

Identify SIRSandRespFailureMild as SIRSandPDAcidosisOrLactateSaO2Mild or SIRSandPDSPO2RRMild locate in inflammatory, Respiratory;

Identify SIRSandRespFailureMod as SIRSandPDAcidosisOrLactateSaO2Mod or SIRSandPDSPO2RRMod locate in inflammatory, Respiratory;

Identify SIRSandRespFailureSevere as SIRSandPDAcidosisOrLactateSaO2Severe or SIRSandPDSPO2RRSevere locate in inflammatory, Respiratory;

Identify SIRSandRespFailureProfound as SIRSandPDAcidosisOrLactateSaO2Profound or SIRSandPDSPO2RRProfound locate in inflammatory, Respiratory;

---PAID parenteral antibiotic indicating disorder

Identify Sepsis as

SIRSMarginal or
SIRSMild locate in inflammatory indicate PAID;

Identify SepsisModerate as
SIRSMod or

InflammatoryAugmentationMod or
InflammatoryAugmentationandPlateletsLoworFallMild or
InflammatoryAugmentationandCalciumMod or
SIRSandAlbuminMod or
SIRSandCreatinineMild
locate in inflammatory
indicate PAID;

Identify SepsisSevere as
SIRSSevere or

InflammatoryAugmentationSevere or
SIRSandRespFailureMild or
InflammatoryAugmentationandAcidMod or
SIRSandCreatinineMod or
InflammatoryAugmentationandPlateletsLoworFallMod or
NeutrophilFailureMod or
SIRSandAcidMod
locate in inflammatory
indicate PAID, Sepsis;

Identify SepsisProfound as
SIRSSevere or

InflammatoryAugmentationProfound or
SIRSandRespFailureMod or
InflammatoryAugmentationandAcidSevere or
SIRSandCreatinineSevere or InflammatoryAugmentationandPlateletsLoworFallSevere or NeutrophilFailureSevere or SIRSandAcidMod locate in inflammatory indicate PAID, Sepsis;

Identify SepsisPromptResuscitationRequired as

SIRSandRespFailureSevere or

InflammatoryAugmentationandAcidProfound or

SIRSandAcidSevere locate in inflammatory indicate PAID, Sepsis;

What is claimed is:

1. A patient monitoring system for generating real-time images of changes in severity of sepsis comprising:
    a real-time patient monitor having a display, a memory comprising instructions, and a processor, communicatively coupled to the memory and the display, that executes or facilitates execution of the instructions, such that the processor is programmed to:
        receive, for each of at least five different clinical tests, at least two sequential clinical test values of that test;
        detect at least one perturbation of the sequential values of each test, each perturbation being one of a rise of the values of that test or a fall of the values of that test;
        for each perturbation, determine at least two features, wherein each feature is a value of the perturbation corresponding to a feature type, wherein the feature type comprises at least one of: a beginning value, an end value, a peak value, a nadir value, a slope, a duration, a percent change, a magnitude, or a product of the magnitude multiplied by the slope;
        generate a feature image component for each determined feature, the feature image component having a visual aspect responsive to the corresponding determined feature;
        generate a perturbation image component for each detected perturbation, wherein each perturbation image component comprises a time dimensioned horizontal bar responsive to the features of the detected perturbation; and
        graphically present on the display an image comprising the horizontal bars and the feature image components on a time dimensioned map, the image changing in real-time in response to changes in the features, the image being indicative of a change in the severity of sepsis over time.

2. The patient monitoring system of claim 1, wherein the processor is further programmed to aggregate the horizontal bars, the aggregated bars in combination defining a vertical dimension which increases with an increasing number of vertically overlapping bars at any given time and decreases with a decreasing number of overlapping bars, the vertical dimension being responsive of the number of detected perturbations which are present at the same time.

3. The patient monitoring system of claim 2, wherein the processor is further programmed to aggregate the horizontal bars so that an increase in the vertical dimension is responsive to an increase in the severity of sepsis over time and a decrease in the vertical dimension is responsive to a decrease in the severity of sepsis over time.

4. The patient monitoring system of claim 3, wherein the visual aspect is color and the color is configured so that both the color and the vertical dimension of the aggregated bars are responsive to an increase in severity of sepsis over time or a decrease in severity of sepsis over time.

5. The patient monitoring system of claim 1, wherein the visual aspect is at least one of size, orientation, fill color or texture, border color or texture, or transparency.

6. The patient monitoring system of claim 1 wherein each horizontal bar grows across the map over time as the duration of the detected perturbation increases.

7. The patient monitoring system of claim 1 wherein each horizontal bar defines an area within that bar.

8. The patient monitoring system of claim 7, wherein the feature image components are displayed in or adjacent the area within the bar.

9. The patient monitoring system of claim 7, wherein the processor is further programmed to aggregate the feature image components in or adjacent the area within the bar and to graphically present on the display a time-lapsable image by displaying each bar and the aggregated feature image components adjacent or within each bar for a plurality of additional times.

10. The patient monitoring system of claim 1, wherein the processor is further programmed to generate a bar responsive to the features of a detected perturbation by aggregating the feature image components of the detected perturbation.

11. The patient monitoring system of claim 1, wherein the map comprises a plurality of clinical regions, and wherein each bar is displayed within a clinical region.

12. The patient monitoring system of claim 1, wherein the processor is further programed to:
    detect at least one relational perturbation comprised of at least two pathophysiologically linked perturbations occurring in timed relationship with each other, and
    generate a relational perturbation image component for the detected relational perturbation, wherein each perturbation image component comprises a time dimensioned horizontal bar responsive to the features of the detected relational perturbation.

13. The patient monitoring system of claim 12 wherein the time dimensioned horizontal bar grows across the map over time as the duration of the detected relational perturbation increases.

14. The patient monitoring system of claim 1, wherein the processor is further programmed to:
    graphically present on display a plurality of defined regions, wherein each region corresponds to a clinical system,
    graphically present each bar on the map within the defined region associated within the clinical system to which the detected perturbation relates and within the time corresponding to the beginning value, the duration, and the end value of the detected perturbation.

15. The patient monitoring system of claim 14, wherein the processor is further programmed to aggregate the bars within a defined region, the aggregated bars in combination defining a vertical dimension within the defined region which increases with an increasing number of vertically overlapping bars at any given time and decreases with a decreasing number of vertically overlapping bars at any given time, the vertical dimension being responsive to a change of the severity of sepsis induced change of the clinical system to which the region corresponds.

* * * * *